(12) United States Patent
Yun et al.

(10) Patent No.: US 9,570,265 B1
(45) Date of Patent: *Feb. 14, 2017

(54) X-RAY FLUORESCENCE SYSTEM WITH HIGH FLUX AND HIGH FLUX DENSITY

(71) Applicants: Wenbing Yun, Walnut Creek, CA (US); Sylvia Jia Yun Lewis, San Francisco, CA (US); Janos Kirz, Berkeley, CA (US)

(72) Inventors: Wenbing Yun, Walnut Creek, CA (US); Sylvia Jia Yun Lewis, San Francisco, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,855

(22) Filed: Sep. 19, 2016

Related U.S. Application Data

(63) Continuation-in-part of application No. 14/544,191, filed on Dec. 5, 2014, now Pat. No. 9,449,781, and a
(Continued)

(51) Int. Cl.
*G01N 23/223* (2006.01)
*H01J 35/14* (2006.01)
(Continued)

(52) U.S. Cl.
CPC ............ *H01J 35/14* (2013.01); *G01N 23/223* (2013.01); *H01J 35/08* (2013.01); *H01J 35/18* (2013.01)

(58) Field of Classification Search
CPC G01N 23/223; G01N 23/063; G01N 23/2076; G21K 1/06; G21K 2201/061; G21K 2201/062; G21K 2201/064; G21K 1/067; H01J 2235/081; H01J 2235/086; H01J 35/08; H01J 35/14; H01J 2235/087; C07H 13/06; C07H 13/12; C07H 15/10; C07H 5/06

See application file for complete search history.

(56) References Cited

U.S. PATENT DOCUMENTS 3,795,832 A 3/1974 Holland
4,227,112 A 10/1980 Waugh
(Continued)

FOREIGN PATENT DOCUMENTS

EP 0432568 A2 6/1991
EP 0751533 A1 1/1997
(Continued)

OTHER PUBLICATIONS

N. Langhoff & A. Simionovici, "X-ray Sources", Ch. 2 of "Handbook of Practical X-Ray Fluorescence Analysis", B. Beckhoff et al., eds. (Springer, Berlin Heidelberg New York, 2006), pp. 33-82.
(Continued)

*Primary Examiner* — David Porta
*Assistant Examiner* — John Corbett
(74) *Attorney, Agent, or Firm* — Franklin Schellenberg

(57) ABSTRACT

We present a micro-x-ray fluorescence (XRF) system having a high-brightness x-ray illumination system with high x-ray flux and high flux density. The higher brightness is achieved in part by using x-ray target designs that comprise a number of microstructures of x-ray generating materials fabricated in close thermal contact with a substrate having high thermal conductivity. This allows for bombardment of the targets with higher electron density or higher energy electrons, which leads to greater x-ray flux. The high brightness/high flux x-ray source may then be coupled to an x-ray optical system, which can collect and focus the high flux x-rays to spots that can be as small as one micron, leading to high flux density at the fluorescent sample. Such systems may be
(Continued)

useful for a variety of applications, including mineralogy, trace element detection, structure and composition analysis, metrology, as well as forensic science and diagnostic systems.

20 Claims, 32 Drawing Sheets

Related U.S. Application Data continuation-in-part of application No. 14/636,994, filed on Mar. 3, 2015, now Pat. No. 9,448,190.

(60) Provisional application No. 61/912,478, filed on Dec. 5, 2013, provisional application No. 61/912,486, filed on Dec. 5, 2013, provisional application No. 61/946,475, filed on Feb. 28, 2014, provisional application No. 62/008,856, filed on Jun. 6, 2014, provisional application No. 62/008,856, filed on Jun. 6, 2014, provisional application No. 62/086,132, filed on Dec. 1, 2014, provisional application No. 62/117,062, filed on Feb. 17, 2015.

(51) Int. Cl.
*H01J 35/18* (2006.01)
*H01J 35/08* (2006.01)

(56) References Cited

U.S. PATENT DOCUMENTS

| | | |
|---|---|---|
| 4,266,138 A | 5/1981 | Nelson, Jr. |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis |
| 5,008,918 A | 4/1991 | Lee |
| 5,148,462 A | 9/1992 | Spitsyn et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,729,583 A | 3/1998 | Tang |
| 5,768,339 A | 6/1998 | O'Hara |
| 5,772,903 A | 6/1998 | Hirsch |
| 5,825,848 A | 10/1998 | Virshup |
| 5,832,052 A | 11/1998 | Hirose et al. |
| 5,857,008 A | 1/1999 | Reinhold |
| 5,878,110 A | 3/1999 | Yamamoto et al. |
| 5,912,940 A | 6/1999 | O'Hara |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,359,964 B1 | 3/2002 | Kogan |
| 6,377,660 B1 | 4/2002 | Ukita |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki |
| 6,560,313 B1 | 5/2003 | Harding |
| 6,560,315 B1 | 5/2003 | Price |
| 6,707,883 B1 | 3/2004 | Tiearney, Jr. et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,885,503 B2 | 4/2005 | Yun |
| 6,914,723 B2 | 7/2005 | Yun |
| 6,917,472 B1 | 7/2005 | Yun |
| 6,947,522 B2 | 9/2005 | Wilson et al. |
| 6,975,703 B2 | 12/2005 | Wilson |
| 7,003,077 B2 | 2/2006 | Jen |
| 7,023,955 B2 | 4/2006 | Chen |
| 7,057,187 B1 | 6/2006 | Yun et al. |
| 7,079,625 B2 | 7/2006 | Lenz |
| 7,095,822 B1 | 8/2006 | Yun |
| 7,119,953 B2 | 10/2006 | Yun |
| 7,130,375 B1 | 10/2006 | Yun et al. |
| 7,170,969 B1 | 1/2007 | Yun et al. |
| 7,180,981 B2 | 2/2007 | Wang |
| 7,183,547 B2 | 2/2007 | Yun |
| 7,215,736 B1 | 5/2007 | Wang |
| 7,215,741 B2 | 5/2007 | Ukita |
| 7,218,700 B2 | 5/2007 | Huber et al. |
| 7,218,703 B2 | 5/2007 | Yada |
| 7,221,731 B2 | 5/2007 | Yada |
| 7,245,696 B2 | 7/2007 | Yun |
| 7,268,945 B2 | 9/2007 | Yun |
| 7,286,640 B2 | 10/2007 | Yun |
| 7,297,959 B2 | 11/2007 | Yun |
| 7,330,533 B2 | 2/2008 | Sampayon |
| 7,346,148 B2 | 3/2008 | Ukita |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert |
| 7,388,942 B2 | 6/2008 | Wang |
| 7,394,890 B1 | 7/2008 | Wang |
| 7,400,704 B1 | 7/2008 | Yun et al. |
| 7,406,151 B1 | 7/2008 | Yun et al. |
| 7,412,024 B1 | 8/2008 | Yun |
| 7,412,030 B1 | 8/2008 | O'Hara |
| 7,412,131 B2 | 8/2008 | Lee |
| 7,414,787 B2 | 8/2008 | Yun |
| 7,443,953 B1 | 10/2008 | Yun et al. |
| 7,499,521 B2 | 3/2009 | Wang |
| 7,522,707 B2 | 4/2009 | Steinlage et al. |
| 7,529,343 B2 | 5/2009 | Safai et al. |
| 7,551,719 B2 | 6/2009 | Yokhin et al. |
| 7,561,662 B2 | 7/2009 | Wang |
| 7,583,789 B1 | 9/2009 | MacDonad |
| 7,601,399 B2 | 10/2009 | Bamola |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Wu et al. |
| 7,800,072 B2 | 9/2010 | Yun |
| 7,813,475 B1 | 10/2010 | Wu et al. |
| 7,864,426 B2 | 1/2011 | Yun et al. |
| 7,864,922 B2 | 1/2011 | Kawabe |
| 7,873,146 B2 | 1/2011 | Okunuki |
| 7,876,883 B2 | 1/2011 | O'Hara |
| 7,914,693 B2 | 3/2011 | Jeong et al. |
| 7,920,676 B2 | 4/2011 | Yun et al. |
| 7,929,667 B1 | 4/2011 | Zhuang |
| 7,974,379 B1 | 7/2011 | Case |
| 7,991,120 B2 | 8/2011 | Okunuki |
| 8,036,341 B2 | 10/2011 | Lee |
| 8,068,579 B1 | 11/2011 | Yun et al. |
| 8,094,784 B2 | 1/2012 | Morton |
| 8,208,603 B2 | 6/2012 | Sato |
| 8,243,884 B2 | 8/2012 | Rödhammer et al. |
| 8,306,184 B2 | 11/2012 | Chang |
| 8,353,628 B1 | 1/2013 | Yun et al. |
| 8,360,640 B2 | 1/2013 | Reinhold |
| 8,406,378 B2 | 3/2013 | Wang |
| 8,416,920 B2 | 4/2013 | Okumura et al. |
| 8,422,633 B2 | 4/2013 | Lantz |
| 8,509,386 B2 | 8/2013 | Lee |

(56) References Cited

U.S. PATENT DOCUMENTS

| | | |
|---|---|---|
| 8,526,575 B1 | 9/2013 | Lyon |
| 8,553,843 B2 | 10/2013 | Drory |
| 8,559,597 B2 | 10/2013 | Chen et al. |
| 8,602,648 B1 | 12/2013 | Jacobsen |
| 8,699,667 B2 | 4/2014 | Steinlage et al. |
| 8,735,844 B1 | 5/2014 | Khaykovich et al. |
| 8,737,565 B1 | 5/2014 | Lyon |
| 8,744,048 B2 | 6/2014 | Lee et al. |
| 8,831,175 B2 | 9/2014 | Silver et al. |
| 8,831,179 B2 | 9/2014 | Adler |
| 8,995,622 B2 | 3/2015 | Adler |
| 9,016,943 B2 | 4/2015 | Jacobsen |
| 9,129,715 B2 | 9/2015 | Adler et al. |
| 9,448,190 B2 * | 9/2016 | Yun ................... G01N 23/2076 |
| 9,449,781 B2 * | 9/2016 | Yun ........................ H01J 35/08 |
| 2004/0120463 A1 | 6/2004 | Wilson et al. |
| 2005/0074094 A1 | 4/2005 | Jen |
| 2005/0123097 A1 | 6/2005 | Wang |
| 2005/0282300 A1 | 12/2005 | Yun et al. |
| 2007/0071174 A1 | 3/2007 | Hebert |
| 2007/0108387 A1 | 5/2007 | Yun et al. |
| 2007/0110217 A1 | 5/2007 | Ukita |
| 2007/0248215 A1 | 10/2007 | Ohshima |
| 2008/0089484 A1 | 4/2008 | Reinhold |
| 2008/0094694 A1 | 4/2008 | Yun et al. |
| 2008/0159707 A1 | 7/2008 | Lee |
| 2008/0170662 A1 | 7/2008 | Reinhold |
| 2008/0170668 A1 | 7/2008 | Kruit et al. |
| 2008/0181363 A1 | 7/2008 | Fenter |
| 2009/0154640 A1 | 6/2009 | Baumann et al. |
| 2009/0316860 A1 | 12/2009 | Okunuki et al. |
| 2010/0040202 A1 | 2/2010 | Lee |
| 2010/0141151 A1 | 6/2010 | Reinhold |
| 2010/0272239 A1 | 10/2010 | Lantz |
| 2010/0284513 A1 | 11/2010 | Kawabe |
| 2011/0026680 A1 * | 2/2011 | Sato ........................ H01J 35/06 378/119 |
| 2011/0135066 A1 | 6/2011 | Behling |
| 2012/0163547 A1 | 6/2012 | Lee et al. |
| 2012/0269323 A1 | 10/2012 | Adler |
| 2012/0269324 A1 | 10/2012 | Adler |
| 2012/0269325 A1 | 10/2012 | Adler |
| 2012/0269326 A1 | 10/2012 | Adler |
| 2013/0195246 A1 | 8/2013 | Tamura |
| 2013/0259207 A1 | 10/2013 | Omote |
| 2013/0308754 A1 | 11/2013 | Yamazaki |
| 2014/0037052 A1 | 2/2014 | Adler |
| 2014/0064445 A1 | 3/2014 | Adler |
| 2014/0072104 A1 | 3/2014 | Jacobsen |
| 2014/0105363 A1 | 4/2014 | Chen et al. |
| 2014/0177800 A1 | 6/2014 | Sato et al. |
| 2014/0185778 A1 | 7/2014 | Lee et al. |
| 2014/0211919 A1 | 7/2014 | Ogura |
| 2014/0369469 A1 | 12/2014 | Ogura et al. |
| 2015/0030127 A1 | 1/2015 | Aoki |
| 2015/0043713 A1 | 2/2015 | Chen |
| 2015/0247811 A1 * | 9/2015 | Yun ...................... G01N 23/223 378/45 |
| 2016/0268094 A1 * | 9/2016 | Yun ...................... H01J 35/106 |

FOREIGN PATENT DOCUMENTS

| | | |
|---|---|---|
| EP | 1028451 A1 | 8/2000 |
| JP | 2000-306533 A | 11/2000 |
| JP | 2007-265981 A | 10/2007 |
| JP | 2007-311185 A | 11/2007 |
| JP | 2013-160637 A | 8/2013 |
| WO | 95/06952 A1 | 3/1995 |
| WO | 98/11592 A1 | 3/1998 |
| WO | 02/39792 A1 | 5/2002 |
| WO | 03/081631 A1 | 10/2003 |
| WO | 2005/109969 A2 | 11/2005 |
| WO | 2006/096052 A2 | 9/2006 |
| WO | 2009/098027 A1 | 8/2009 |
| WO | 2013/118593 A1 | 8/2013 |
| WO | 2013/168468 A1 | 11/2013 |

OTHER PUBLICATIONS

Jens Als-Nielsen & Des McMorrow "X-rays and their interaction with matter", and "Sources", Ch.1 & 2 of "Elements of Modern X-ray Physics, Second Edition" (John Wiley & Sons Ltd, Chichester, West Sussex, UK, 2011), pp. 1-67.

P.J. Potts, "Electron Probe Microanalysis", Ch. 10 of "A Handbook of Silicate Rock Analysis" (Springer Science + Business Media, New York, 1987), pp. 326-382 (equation quoted from p. 336).

Heinz-Dieter Nuhn, "From storage rings to free electron lasers for hard x-rays", J. Phys.: Condens. Matter vol. 16 (2004), pp. S3413-S34121.

Shigehiko Yamamoto, "Fundamental physics of vacuum electron sources", Reports on Progress in Physics vol. 69, (2006), pp. 181-232.

Aamir Ihsan, Sung Hwan Heo & Sung Oh Cho, "A microfocus X-ray tube based on a microstructured X-ray target", Nuclear Instruments and Methods in Physics Research B vol. 267 (2009), pp. 3566-3573.

X.D. Wang et al., "Precise patterning of diamond films for MEMS application" Journal of Materials Processing Technology vol. 127 (2002) pp. 230-233.

Jicheng Zhang et al., "Fabrication of Diamond Microstructures by Using Dry and Wet Etching Methods", Plasma Science and Technology vol. 15(6) (Jun. 2013), pp. 552-554.

B.L. Henke, E.M. Gullikson, and J.C. Davis, in "X-ray interactions: photoabsorption, scattering, transmission, and reflection at E=50-30000 eV, Z=1-92", Atomic Data and Nuclear Data Tables vol. 54 (No. 2) (Jul. 1993), pp. 181-342.

Genta Sato et al., "Two-dimensional gratings-based phase-contrast imaging using a conventional x-ray tube", Opt. Lett. 36(18) (2011), pp. 3551-3553.

N. Morimoto et al., "Development of multiline embedded X-ray targets for X-ray phase contrast imaging", in XTOP 2012 Book of Abstracts, (Ioffe Physical-Technical Institute of the Russian Academy of Sciences, St. Petersburg, Russia, 2012), pp. 74-75.

Takayoshi Shimura et al., "Hard x-ray phase contrast imaging using a tabletop Talbot-Lau Interferometer with multiline embedded x-ray targets", Opt. Lett. vol. 38(2) (2013) pp. 157-159.

Paul Kirkpatrick & A.V. Baez, "Formation of Optical Images by X-Rays" J. Opt. Soc. Am. vol. 38 (Sep. 1948), pp. 766-774.

Hans Wolter, "Spiegelsysteme streifenden Einfalls als abbildende Optiken für Röntgenstrahlen" [Grazing-Incidence Reflector Systems as Imaging Optics for X-rays] Annalen der Physik vol. 445, Issue 1-2 (1952), pp. 94-114.

Janos Kirz, "Phase zone plates for x rays and the extreme uv" J. Opt. Soc. Am. vol. 64 (Mar. 1974) pp. 301-309.

Troy W. Barbee Jr. "Multilayers for x-ray optics" Opt. Eng. vol. 25 (Aug. 1986) pp. 898-915.

Malcolm R. Howells, "Mirrors for Synchrotron-Radiation Beamlines", Publication LBL-34750 (Larrence Berkeley Laboratory, Berkeley, CA, Sep. 1993).

David X. Balaic & Keith A. Nugent, "X-ray optics of tapered capillaries" Appl. Opt. vol. 34 (Nov. 1995), pp. 7263-7272.

Muradin A. Kumakhov, "X-ray Capillary Optics. History of Development and Present Status" in Kumakhov Optics and Application, Proc. SPIE vol. 4155 (2000), pp. 2-12.

Carolyn A. MacDonald & Walter M. Gibson, "An Introduction to X-ray and Neutron Optics", Ch. 19 of "Handbook of Optics vol. III, 2nd Ed." (McGraw Hill, New York, 2001).

B. Lengeler, C. Schroer, J. Tümmler, B. Benner, A. Snigirev & I. Snigireva, "Refractive X-ray Optics", Ch. 20 of "Handbook of Optics vol. III, 2nd Ed." (McGraw Hill, New York, 2001).

Malcolm R. Howells, "Gratings and Monochromators in the VUV and Soft X-ray Spectral Region" Ch. 21 of "Handbook of Optics vol. III, 2nd Ed." (McGraw Hill, New York, 2001).

(56) References Cited

OTHER PUBLICATIONS

Peter Siddons, "Crystal Monochromators and Bent Crystals" Ch. 22 of "Handbook of Optics vol. III, 2nd Ed." (McGraw Hill, New York, 2001).
Alan Michette, "Zone and Phase Plates, Bragg-Fresnel Optics" Ch. 23 of "Handbook of Optics vol. III, 2nd Ed." (McGraw Hill, New York, 2001).
Eberhard Spiller, "Multilayers" Ch. 24 of "Handbook of Optics vol. III, 2nd Ed." (McGraw Hill, New York, 2001).
M. Yanagihara et al., "X-Ray Optics", Ch. 3 of "X-ray Spectrometry: Recent Technological Advances", K. Tsuji et al. eds. (John Wiley & Sons, Ltd. Chichester, West Sussex, UK, 2004), pp. 63-131.
Li et al., "Source-optic-crystal optimisation for compact monochromatic imaging", Proc. SPIE 5537 (2004), pp. 105-114.
A. Erko et al., "X-ray Optics", Ch. 3 of "Handbook of Practical X-Ray Fluorescence Analysis", B. Beckhoff et al., eds. (Springer, Berlin, Germany, 2006), pp. 85-198.
Barry Lai, "X-Ray Microfocusing Optics", Slide Presentation from Argonne Nat'l Lab, Cheiron Summer School 2007, available at: < http://cheiron2007.spring8.or.jp/pdf/Lai.pdf >.
Xianghui Zeng et al., "Ellipsoidal and parabolic glass capillaries as condensers for x-ray microscopes", Appl. Opt. vol. 47 (May 2008), pp. 2376-2381.
"Optics and Detectors", Section 4 of X-Ray Data Booklet, 3rd Ed., A.C. Thompson ed. (Lawrence Berkeley Nat'l Lab, Berkeley, CA, 2009). Available at < http://xdb.lbl.gov/ >.
T. Matsushita, "Mirrors and Multilayers", Slide Presentation from Photon Factory, Tsukuba, Japan (Cheiron School 2009, SPring-8, Japan, Nov. 2009) available at: < http://cheiron2009.spring8.or.jp/images/PDF/Lecture/Mirror_and_Multilayer_T_Matsushita.pdf >.
X. Zeng et. al., "Glass Monocapillary X-ray Optics and Their Applications in X-Ray Microscopy", in X-ray Optics and Microanalysis: Proceedings of the 20th International Congress, AIP Conf. Proc. vol. 1221, (2010), pp. 41-47.
Roger Falcone et al., "New directions in X-ray microscopy", Contemporary Physics vol. 52, No. 4 (Jul.-Aug. 2010), pp. 293-318.
Yoshio Suzuki et al., "Hard X-ray Imaging Microscopy using X-ray Guide Tube as Beam Condenser for Field Illumination" J. Phys.: Conf. Ser. vol. 463 (2013), 012028.
Stefan Vogt, "X-ray Fluorescence Microscopy: A Tool for Biology, Life Science and Nanomedicine." Presentation on May 16, 2012 at James Madison Univ., Harrisonburg, VA (31 slides). Available at: http://commons.lib.jmu.edu/photon/2012/presentations/9/ Accessed Jan. 30, 2016.
Serguei Kuznetsov, "X-Ray Optics Calculator" Institute of Microelectronics Technology and High Purity Materials, Russian Academy of Sciences (IMT RAS), Chernogolovka, Russia (6 pages submitted). Available at: http://purple.ipmt-hpm.ac.ru/xcalc/xcalc_mysql/ref_index.php, Accessed Feb. 8, 2016.
X-ray-Optics.de Website http://www.x-ray-optics.de/ Accessed Feb. 13, 2016.
C. J. Sparks Jr. "X-ray Fluorescence Microprobe for Chemical Analysis" in Synchrotron Radiation Research, H. Winick & S. Doniach, eds. (Plenum Press, New York, NY 1980) pp. 459-512.
P. Pianetta et al., "Application of synchrotron radiation to TXRF analysis of metal contamination on silicon wafer surfaces", Thin Solid Films vol. 373(1-2), 2000, pp. 222-226.
Z.W. Chen, F. Wei & D. Gibson, "Advance in detection of low sulfur content by wavelength dispersive XRF", Proceedings of the Annual ISA Analysis Division Symposium (2002), Available at: < https://xos.com/wp-content/uploads/ISA%20Paper.pdf >.
A. Bjeoumikhov et al. "A modular system for XRF and XRD applications consisting of a microfocus X-ray source and different capillary optics" X-ray Spectrometry vol. 33 (2004) pp. 312-316.
P. Wobrauschek el al. "Micro XRF of light elements using a polycapillary lens and an ultra-thin window Silicon Drift Detector inside a vacuum chamber", International Centre for Diffraction Data 2005, Advances in X-ray Analysis, vol. 48, 2005, pp. 229-235).
A. Ide-Ektessabi & M. Rabionet "The role of trace metallic elements in neurodegenerative disorders: quantitative analysis using XRF and XANES spectroscopy." Anal Sci. vol. 21(7) (Jul. 2005), pp. 885-892.
R. Ortega, G. Devès & A. Carmona, "Bio-metals imaging and speciation in cells using proton and synchrotron radiation X-ray microspectroscopy" J. Royal Society Interface vol. 6 suppl. 5 (Oct. 6, 2009) pp. 6S649-6S658.
Koen Janssens et al. "Recent trends in quantitative aspects of microscopic X-ray fluorescence analysis." TrAC Trends in Analytical Chemistry 29.6 (Jun. 2010): 464-478.
Peter Wobrauschek, Christina Streli & Eva Selin Lindgren, "Energy Dispersive, X-Ray Fluorescence Analysis", Encyclopedia of Analytical Chemistry, R.A. Meyers, Ed. (Wiley 2010).
Zhenyu Qin et al., "Trace metal imaging with high spatial resolution: Applications in biomedicine", Metallomics vol. 3 (Jan. 2011), pp. 28-37.
Jeffrey M. Davis et al., "Bridging the Micro-to-Macro Gap: A New Application for Micro X-Ray Fluorescence", Microsc Microanal. vol. 17(3) (Jun. 2011) pp. 410-417.
Daryl L. Howard et al., "High-Definition X-ray Fluorescence Elemental Mapping of Paintings" Anal. Chem., 2012, vol. 84 (7), pp. 3278-3286.
Ramón Fernández-Ruiz, "TXRF Spectrometry as a Powerful Tool for the Study of Metallic Traces in Biological Systems", Development in Analytical Chemistry vol. 1 (2014) pp. 1-14.
L. Strüder et al., "X-Ray Detectors", Ch. 4 of "X-ray Spectrometry: Recent Technological Advances", K. Tsuji et al. eds. (John Wiley & Sons, Ltd. Chichester, West Sussex, UK, 2004), pp. 63-131.
Lothar Strüder, "Silicon Drift Detectors for X-ray Imaging", Presentation at Detector Workshop on Synchrotron Radiation Instrumentation, 54 slides (Argonne Nat'l Lab, Argonne,IL Dec. 8, 2005) Available at: < http://www.aps.anl.gov/News/Conferences/2005/Synchrotron_Radiation_Instrumentation/Presentations/Strueder.pdf >.
A. Scholze et al., "X-ray Detectors and XRF Detection Channels", Ch. 4 of "Handbook of Practical X-Ray Fluorescence Analysis", B. Beckhoff et al., eds. (Springer, Berlin Heidelberg, Germany, 2006), pp. 85-198.

* cited by examiner

X-RAY FLUORESCENCE SYSTEM WITH HIGH FLUX AND HIGH FLUX DENSITY

CROSS-REFERENCE TO RELATED APPLICATIONS

This Patent Application is a Continuation-in-Part of U.S. patent application Ser. No. 14/544,191, filed Dec. 5, 2014 and soon to issue as U.S. Pat. No. 9,449,781, which is hereby incorporated by reference in its entirety, and which in turn claims the benefit of U.S. Provisional Patent Application No. 61/912,478, filed on Dec. 5, 2013, 61/912,486, filed on Dec. 5, 2013, 61/946,475, filed on Feb. 28, 2014, and 62/008,856, filed on Jun. 6, 2014, all of which are incorporated herein by reference in their entirety. The present Application is also a Continuation-in-Part of U.S. patent application Ser. No. 14/636,994, filed Mar. 3, 2015 and soon to issue as U.S. Pat. No. 9,448,190, which is hereby incorporated by reference in its entirety, and which in turn claims the benefit of U.S. Provisional Patent Application No. 62/008,856, filed Jun. 6, 2014; 62/086,132, filed Dec. 1, 2014, and 62/117,062, filed Feb. 17, 2015, all of which are incorporated herein by reference in their entirety.

FIELD OF THE INVENTION

The embodiments of the invention disclosed herein relate to micro-x-ray fluorescence (XRF) systems having a high-brightness x-ray illumination system, and in particular, to a fluorescence system with an x-ray illuminator having high x-ray flux and high flux density. Such systems may be useful for a variety of applications, including mineralogy, trace element detection, structure and composition analysis, metrology, as well as forensic science and diagnostic systems.

BACKGROUND OF THE INVENTION

Introduction

X-rays are a very useful form of radiation to see into materials because most materials are quite transparent to x-rays: the complex refractive index at x-ray energies for most substances is very close to 1. Designing reflective and refractive optical elements analogous to those that are well known in the visible portion of the electromagnetic spectrum (where refractive indices are typically 1.4 or higher) cannot be used at x-ray wavelengths. Designing and constructing illuminators for applications of x-rays can therefore be particularly challenging.

For scientific studies of materials, where high brightness may be needed to obtain adequate signal-to-noise ratios over a range of x-ray energies, conventional x-ray sources using electron bombardment are simply not adequate.

For scientific studies of materials that need high brightness x-rays, and in particular the atomic structure and composition analysis that can be achieved by analyzing x-ray diffraction or fluorescence, high brightness synchrotrons or free-electron lasers have been used with great success. However, these facilities are large, often occupying acres of land, and expensive to operate, and obtaining beamtime can take months of waiting.

Laboratory systems that can be used for these applications, and in particular micro-x-ray fluorescence for materials analysis, would therefore be highly desired. The main problem for producing such a system is the lack of a suitable system with an x-ray source and efficient optics for achieving a tightly focused, high flux and high flux density x-rays.
X-Ray Fluorescence.

To better understand the utility of a high flux/high flux density x-ray illuminator, it helps to understand the requirements of the applications for which it will be used, and in particular, the requirements of x-ray fluorescence. When materials are exposed to high energy particles, such as x-rays and gamma rays, tightly held electrons from the inner electron shells of the atom can be ejected. To fill the vacancy so created, electrons in higher electron shells transition into the lower orbital, releasing energy difference between the electron shells in the form of an emitted photon. The energy level structure is distinct for each type of atom, and therefore the energy of the emitted photons is characteristic of the atoms present in the material. The term fluorescence is applied to phenomena in which the absorption of radiation of a specific energy results in the emission of lower energy radiation.

X-ray fluorescence is illustrated in FIG. 1, which shows a representation of the electrons around an atom with electrons in the K, L and M shells, and in which an incident high energy x-ray has ejected an electron from the inner K shell. When an electron from next higher shell (the L shell) transitions to fill the vacancy, the characteristic $K_{\alpha 1}$ x-ray photon for the material is emitted. When an electron from 2nd next higher shell (the M shell) transitions to fill the vacancy, the characteristic $K_{\beta 1}$ x-ray photon for the material is emitted. For most atoms, an empirical relationship called Moseley's Law relates the atomic number Z and the energy of the $K_{\alpha 1}$ fluorescence:

$$E_{K\alpha}[keV] \approx 1.017 \times 10^{-2}(Z-1)^2 \qquad [\text{Eqn.1}]$$

In this manner, detection of the energy emitted indicates the presence of particular elements Z, and the strength of the fluorescence can be related to the relative concentrations of the atomic material.

FIG. 2 illustrates a simple conventional prior art x-ray fluorescence system P200. The system P200 comprises an x-ray source P80 comprising a high voltage supply P10, an electron emitter P11 that emits electrons P111 that bombard a target P100, generating x-rays P888. The x-rays P888 typically pass through a window P40 and irradiate a sample of material P240 held in a sample holder P244. Such a sample holder may be a simple tray, or comprise a complex mount, having controls for translation in x, y and z directions, and may also include x, y, and/or z-axis rotation mechanisms. A portion of the x-ray fluorescence P2888 emitted by the sample of material P240 is detected by a specially designed detector P290, which may be an electron drift detector that can discriminate between the energies of the x-ray photons detected, or may comprise a combination of a spectrometer and a detector, that generates an electronic signal representing the number of counts for the fluorescent x-rays at various energies. Once converted to electronic signals, various electronic components P292 may provide additional processing, and the data may be sent over a connector to an analysis system P295 for further analysis, which may also comprise a display P298.

Such systems are often employed in a lab environment, in which a sample of material is brought to the lab and mounted in the machine for analysis. With the reduction in size of modern electronics, XRF systems that are handheld have been developed. Such a system is illustrated in FIGS. 3A and 3B.

The handheld system H200 of FIGS. 3A and 3B also comprises a source H80 of x-rays H888 that are directed towards an object for analysis, in this example, a toy duck H240 being tested for the presence of toxic chemicals such as lead in its paint and materials. The x-ray fluorescence H2888 from the object H240 is detected by a specially designed detector H290 that generates an electronic signal representing the number of counts for the fluorescent x-rays at various energies. Once converted to electronic signals, various electronic components H292, optional digital signal processing components H293 and a central processing unit (CPU) H295 may provide additional processing and analysis of the signals, and presented on an integrated display H298 for the user or stored in integrated memory devices H299 for downloading and further analysis at a later time.

Microfocus XRF Systems.

Both of the prior art systems described so far simply illuminate a object with x-rays and detect the fluorescence that is emitted from the illuminated area. However, for many applications, the atomic compositions of microscopic or even nanoscopic grains of material may be of interest. Therefore, additional prior art systems use a microfocus source of x-rays that can then be focused to a microscopic spot on the object, allowing probing of objects on a microscopic scale.

FIG. 4 illustrates the elements of a typical microfocus XRF system M200. The source M80 comprises a vacuum environment (typically $10^{-6}$ torr or better) commonly maintained by a sealed vacuum chamber M20 or active pumping, and manufactured with sealed electrical leads M21 and M22 that pass from the negative and positive terminals of a high voltage source M10 outside the tube to the various elements inside the vacuum chamber M20. The source M80 will typically comprise mounts M30 that secure the vacuum chamber M20 in a housing M50, and the housing M50 may additionally comprise shielding material, such as lead, to prevent x-rays from being radiated by the source M80 in unwanted directions.

Inside the chamber M20, an electron emitter M11 connected through the lead M21 to the high voltage source M10 serves as a cathode and generates a beam of electrons M111, often by running a current through a filament. A target M100 comprising a target substrate M110 and regions M700 of x-ray generating material is electrically connected to the opposite high voltage lead M22 and target support M32 to be at ground or relative positive voltage, thus serving as an anode. The electrons M111 accelerate towards the target M100 and collide with it at high energy, with the energy of the electrons determined by the magnitude of the accelerating voltage. The collision of the electrons M111 into the target M100 induces several effects, including the emission of x-rays 888, some of which are transmitted through a window M40 that is transparent to x-rays.

To create the microfocus x-ray spot on the target, an electron control mechanism M70 such as an electrostatic lens system or other system of electron optics that is controlled and coordinated with the electron dose and voltage provided by the electron emitter M11 by a controller M10-1 through a lead M27. The electron beam M111 may therefore be focused, and scanned onto the target M100.

Once the x-rays 888 exit the source M80, a portion of the x-rays are collected by a set of x-ray optics M840 that focus a portion 887 of the x-rays onto the object 240 to be examined. X-rays that are not collected and focused may be blocked by a beam stop M850. Once the focused portion of the x-rays 887 converge onto the object 240, x-ray fluorescence photons 2888 will propagate away from the object 240 onto a detector M290. As in the other prior art systems, the detector M290 converts the detected counts to electronic signals, which may be further processed by signal processing electronics M292 and passed to an analysis system M295.

X-ray fluorescence is a technique that can be applied to biomedical imaging, materials science, geological, and semiconductor applications and enable up to parts-per-billion sensitivity to map multiple trace elements. It provides several key advantages over charged-particle based techniques such as electron-based imaging (e.g. minimal sample preparation, near absence of a limiting bremsstrahlung background, and significantly reduced radiation damage) [see C. J. Sparks, "X-ray fluorescence microprobe for chemical analysis." in Synchrotron Radiation Research (Springer Verlag-US, 1980), pp. 459-512] and complementary and unique capabilities compared to laser-ablation inductively-coupled-plasma mass spectrometry (LA-ICPMS) (e.g. better absolute detection limits, non-destructive, and sensitivity to non-metals) [see S. Vogt. "X-ray fluorescence microscopy: a tool for biology, life science and nanomedicine", presentation posted online at: commons.lib.jmu.edu/photon/2012/presentations/9/].

XRF analysis offers many inherent advantages for elemental analysis due to the unique interaction of x-rays with matter and the characteristic (signature) x-ray energies (lines) of each and every element in the periodic table with $Z>3$. The technique is nearly nondestructive, simultaneously detects multiple elements, and achieves high signal-to-background ratio, which leads to high sensitivity (low absolute and relative detection limit). In principle, x-ray fluorescence can theoretically realize single atom detection, similar to single molecule detection using light fluorescence techniques, as each atom can yield multiple characteristic fluorescence x-rays with continuous core shell ionization and de-excitation processes.

MicroXRF, in which x-rays are focused to areas with diameters of microns or tens of microns to achieve high-resolution imaging, has long been achieved using x-ray focusing optics and a synchrotron as the x-ray source. However, synchrotrons are large facilities, often taking up acres of land, and beam time is not available for routine analysis. Laboratory systems have been designed using similar x-ray optics, but typically cannot achieve the brightness or x-ray flux possible with synchrotron systems.

There are inherent advantages of XRF for trace level analysis at micron-scale resolution (microXRF) over other techniques for detecting atomic species, such as the dedicated electron microprobe analyzer (EMPA) and scanning electron microscope (SEM) with an x-ray analyzer. These advantages of x-ray induced XRF include:

(1) near absence of the broad bremsstrahlung x-ray background encountered in charged particle based techniques that limits sensitivity to several hundred parts per million;
(2) significantly lower radiation damage;
(3) a need for only minimal specimen preparation, leading to fewer artifacts and lower loss of volatile components; and
(4) a convenient specimen environment (typically operating in ambient condition), with significantly increased ease of use.

The perceived disadvantage of laboratory microXRF is that the excitation spot is too large (typically around 30 microns). For many applications, analysis of material compositions and structure on the micron or sub-micron scale is desired. The spot size is limited due to the low throughput at smaller spot sizes, caused by a combination of low flux at the object under examination and low solid angle of collection for the x-ray fluorescence.

MicroXRF has complementary and unique capabilities when compared with alternative techniques for mapping elemental distributions such as laser ablation chemical analysis techniques including laser-ablation inductively-coupled-plasma mass spectroscopy technique (LA-ICPMS), which is widely adopted for mapping elemental distribution with a spatial resolution typically in the range of 50-100 micrometers. There are several outstanding reviews comparing XRF with this technique [see Z. Y. Qin et al. "Trace metal imaging with high spatial resolution: Applications in biomedicine." Metallomics vol. 3 (2011), pp. 28-37; and R. Ortega et al. "Bio-metals imaging and speciation in cells using proton and synchrotron radiation xray microspectrometry." Journal of the Royal Society Interface vol. 6 (2005) pp. S649-S658.]. Though LA-ICPMS generally offers lower (better) relative detection limit for metals with Z>30 and a unique ability to detect isotopes, it is destructive of the specimen (via ablation), has an inferior absolute detection limit, and suffers from polyatomic interference of many elements with Z<30 for complex matrix materials, like biological specimens. To detect 1000 ions of a given element, a minimum of 108 atoms of the element are required as the input. Furthermore, the detection sensitivity (both absolute and relative) is highly compromised for non-metals (such as sulfur (S), phosphorous (P), and selenium (Se)) and especially halogens (such as fluorine (F), chlorine (Cl), or bromine (Br)) due to their low ionization cross-sections and polyatomic interference.

Due to the demand from the biomedical and materials science communities, a large number of scanning microXRF microprobes have been developed for use in synchrotron radiation facilities around the world with unprecedented capabilities, including parts per billion relative detection limit, 1000 atoms absolute detection limit, sub-50 nm resolution, and fly-scan techniques with sub-3 ms data collection per data point and up to a million pixels in less than three hours [see, for example, D. L. Howard et al. "High-Definition X-ray Fluorescence Elemental Mapping of Paintings" Analytical Chemistry vol. 84 (2012), pp. 3278-3826]. Those capabilities are achieved with several recent technological developments in high brightness synchrotron x-ray sources, high performance x-ray focusing optics, and efficient energy resolving x-ray detectors with high count rates.

Several of these synchrotron developments have also been adapted to smaller laboratory systems in the past decade, and XRF instruments have been deployed in a variety of applications, e.g. screening lead in toys and electronics [see K. Janssens et al., "Recent trends in quantitative aspects of microscopic X-ray fluorescence analysis." TrAC Trends in Analytical Chemistry vol. 29.6 (2010), pp. 464-478], inspection of sulfur in fuel [see Z. W. Chen et al. "Advance in detection of low sulfur content by wavelength dispersive XRF", Proceedings of the ISA (2002)], and mineral mapping in mining samples [see J. M. Davis et al., "Bridging the micro-to-macro gap: a new application for micro x-ray fluorescence." Microscopy and Microanalysis vol. 17 (2011), pp. 410-417].

For this reason, a number of laboratory microXRF systems have also been recently developed and commercialized by the companies Bruker Corp. of Billerica, Mass., Horiba of Kyoto, Japan, and Rigaku Corp. of Tokyo, Japan.

However, the sensitivity and spatial resolution of these laboratory systems has remained limited. Very significant enhancements are required to realize a laboratory XRF with high performance for in-line applications, biological applications, or rapid mapping required for a large number of applications.

General XRF Operation.

For the XRF system as illustrated in FIG. 4, the signal and resolution are governed by the physics of the x-ray optics. The higher the x-ray flux at the object, the larger the fluorescence signal will be. The useable flux of x-rays at the object is given by $$F_0 \propto B_s s \eta (NA)^2 \quad \text{[Eqn. 2]}$$

where $B_S$ is the brightness of the source, s represents the area of the x-ray source, $\eta$ represents the efficiency of the optical system in collecting and refocusing x-ray photons, and NA represents the numerical aperture of the x-ray optics. Therefore, from Eqn. 2, systems with a large source size s and large numerical aperture NA along with high brightness $B_S$ are desired for high flux and therefore a good signal-to-noise ratio for the x-ray fluorescence excited by the incident x-rays.

However, the brightness $B_S$ is in turn related to the source size by $$B_s \propto 1/\sqrt{s} \quad \text{[Eqn. 3]}$$

This means that smaller sources lead to higher brightness. The effective source size can be limited by the angular width $\Delta\theta$ of the x-ray optic at a point on the optic surface, such as the critical angle of a reflective optic or the Darwin width if a crystal or multilayer optic is used, and will also be related to other geometric properties of the system by $$s \leq \Delta\theta L_O \quad \text{[Eqn. 4]}$$

where $L_O$ is the distance from the source to the x-ray optics. When the x-ray source size is larger than $\Delta\theta \cdot L_O$, x-rays generated from a fraction of the source area may be collected by the x-ray optics while x-rays generated by the remaining fraction of the source may not be collected by the x-ray optic. Therefore, a smaller source is generally preferred to obtain high x-ray source brightness and possibly greater flux for a given x-ray optic and distance $L_O$. However, trying to drive too much electron energy into too small a spot on the x-ray target can lead to material damage, limiting the brightness achievable.

X-ray fluorescence is often used to examine the atomic composition of materials, and for many applications, knowing the composition of various ores and complex minerals on the scale of a micron or smaller may be very useful. To achieve this, the x-rays need to be focused to a spot as small as, or smaller than, 1 micron. However, the optical system needed focus tightly and achieve high flux density at the object can be difficult to achieve.

A limitation for such an optical system arises from the poor reflectivity of most materials at most angles of incidence. Because most materials only weakly interact with x-rays, the refractive index of a material at x-ray wavelengths may be represented by:

$$n = 1 - \delta + i\beta \quad \text{[Eqn. 5]}$$

where $\delta$ represents the dispersion and $\beta$ represents the absorption. For most materials at x-ray wavelengths, the perturbations $\delta$ and $\beta$ are on the order of $\pm 10^{-4}$ or smaller, and refraction and absorption are very weak. This makes the fabrication of practical refractive lenses, analogous to optical lenses, very difficult.

However, at grazing angles, total external reflection can occur, and optics that can focus or collimate at higher efficiency for at least a portion of the x-rays can be designed. This is illustrated in FIG. 5 and FIG. 6. For an x-ray of incident at an angle θ onto a surface of a material with atomic number Z, as shown in FIG. 5, the reflectivity is nearly 100% for near-grazing angles (e.g. θ≈0°), and falls off for angles larger than a material-dependent critical angle $\theta_c$, as illustrated in FIG. 6. The value of $\theta_c$ is given by:

$$\theta_c \approx \sqrt{2\delta} \qquad \text{[Eqn. 6]}$$

which can be approximated by $$\theta_c = \sqrt{2\delta} = \frac{\lambda}{2\pi}\sqrt{4\pi\kappa\rho r_0} \qquad \text{[Eqn. 7]}$$

where λ is the x-ray wavelength in nm, ρ is the density of the material in g/cm³, κ is a constant to convert density to the correct units, and $r_0 = 2.82 \times 10^{-6}$ nm, the "classic electron radius" [this derivation may be found in Chapter 3, section 3.1 on "Refraction and Phase Shift in Scattering", in Jens Als-Nielsen and Des McMorrow, *Elements of Modern X-ray Physics* (John Wiley & Sons, 2011)].

Using $$\lambda[nm] = 1.2398/E[keV] \qquad \text{[Eqn. 8]}$$

this becomes $$\theta_c \approx 1.2398\sqrt{\frac{\kappa r_0}{\pi}}\frac{\sqrt{\rho[g/cm^3]}}{E[keV]} = \frac{K\sqrt{\rho[g/cm^3]}}{E[keV]} \qquad \text{[Eqn. 9]}$$

An empirical fit of $\theta_c$ for 34 elements gives an average value of K=18.9, but a better fit is achieved using K=19.7 for E<4 keV, K=19.0 for 4 keV≤E<10 keV, and K=18.4 for E≥10 keV. A Table of $\theta_c$ for several materials calculated using the website purple.ipmt-hpm.ac.ru/xcalc/xcalc_mysql/ref_index.php is shown in Table I. Even for the range of conditions here, total external reflection only occurs for grazing incidence, with angles mostly smaller than 1°, limiting the acceptance angle for most configurations.

Aside from the practical limitations on the amount of x-rays that can be collected and focused by the optical system, the major practical limitation in x-ray source brightness is limitation of the electron density and electron power incident on the x-ray target to prevent target melting or evaporation. Various target designs that incorporate cooling systems, such as water cooling channels or thermoelectric (Peltier) coolers, or using

TABLE I

Critical angle for several materials and several x-ray energies.

| | δ | $\theta_c$ (mrad) | $\theta_c$ (degrees) |
|---|---|---|---|
| Carbon C (Diamond): ρ = 3.5 g/cm³ | | | |
| 2.835 keV | 9.22E−05 | 13.577 | 0.778 |
| 8.048 keV | 1.13E−05 | 4.749 | 0.272 |
| 17.480 keV | 2.38E−06 | 2.184 | 0.125 |
| 30.000 keV | 8.09E−07 | 1.272 | 0.073 |
| 50.000 keV | 2.91E−07 | 0.763 | 0.044 |

TABLE I-continued

Critical angle for several materials and several x-ray energies.

| | δ | $\theta_c$ (mrad) | $\theta_c$ (degrees) |
|---|---|---|---|
| Silicon: ρ = 2.32 g/cm³ | | | |
| 2.835 keV | 6.04E−05 | 10.990 | 0.630 |
| 8.048 keV | 7.58E−06 | 3.892 | 0.223 |
| 17.480 keV | 1.59E−06 | 1.781 | 0.102 |
| 30.000 keV | 5.36E−07 | 1.036 | 0.059 |
| 50.000 keV | 1.93E−07 | 0.621 | 0.036 |
| Silica (SiO₂): ρ = 2.65 g/cm³ | | | |
| 2.835 keV | 5.78E−05 | 10.752 | 0.616 |
| 8.048 keV | 7.13E−06 | 3.775 | 0.216 |
| 17.480 keV | 1.50E−06 | 1.731 | 0.099 |
| 30.000 keV | 5.07E−07 | 1.007 | 0.058 |
| 50.000 keV | 1.82E−07 | 0.604 | 0.035 |
| Copper (Cu): ρ = 8.96 g/cm³ | | | |
| 2.835 keV | 2.11E−04 | 20.555 | 1.178 |
| 8.048 keV | 2.44E−05 | 6.982 | 0.400 |
| 17.480 keV | 5.61E−06 | 3.349 | 0.192 |
| 30.000 keV | 1.90E−06 | 1.949 | 0.112 |
| 50.000 keV | 6.80E−07 | 1.166 | 0.067 |
| Silver (Ag): ρ = 10.49 g/cm³ | | | |
| 2.835 keV | 1.97E−04 | 19.832 | 1.136 |
| 8.048 keV | 2.94E−05 | 7.666 | 0.439 |
| 17.480 keV | 6.09E−06 | 3.490 | 0.200 |
| 30.000 keV | 2.07E−06 | 2.035 | 0.117 |
| 50.000 keV | 7.61E−07 | 1.233 | 0.071 |
| Gold (Au): ρ = 19.30 g/cm³ | | | |
| 2.835 keV | 2.83E−04 | 23.800 | 1.364 |
| 8.048 keV | 4.60E−05 | 9.592 | 0.550 |
| 17.480 keV | 1.00E−05 | 4.480 | 0.257 |
| 30.000 keV | 3.47E−06 | 2.634 | 0.151 |
| 50.000 keV | 1.24E−06 | 1.573 | 0.090 | mechanical motion (such as rotating target anodes to distribute the heat deposition over a larger area) have been designed, but are still limited in the amount of brightness and therefore x-ray flux that can be achieved.

There is therefore a need for a XRF system with a compact, high-brightness x-ray source that can be focused to a small spot for XRF analysis from several hundred microns down to the scale of 1 micron or smaller.

BRIEF SUMMARY OF THE INVENTION

This disclosure presents systems for x-ray fluorescence having x-ray illumination systems that have the potential of having both x-ray flux and x-ray flux density up to several orders of magnitude higher than existing commercial x-ray technologies, and therefore useful for applications such as trace element detection or for micro-focus fluorescence.

The higher brightness is achieved in part through the use of novel configurations for x-ray targets used in generating x-rays from electron beam bombardment. These x-ray target configurations may comprise a number of microstructures of one or more selected x-ray generating materials fabricated in close thermal contact with (such as embedded in or buried in) a substrate with high thermal conductivity, such that the heat is more efficiently drawn out of the x-ray generating material. This in turn allows bombardment of the x-ray generating material with higher electron density and/or higher energy electrons, which leads to greater x-ray brightness and therefore greater x-ray flux.

A significant advantage to some embodiments is that the orientation of the microstructures allows the use of an on-axis collection angle, allowing the accumulation of x-rays from several microstructures to appear to originate at a single origin, and can be used for alignments at "zero-degree takeoff angle" x-ray generation. The linear accumulation of x-rays from the multiple points of origin leads to greater x-ray brightness.

Some embodiments of the invention additionally comprise x-ray optical elements that collect the x-rays from the source and focus them to spots down to 1 micron in diameter. The x-ray optical elements may comprise paraboloid optics, ellipsoidal optics, polycapillary optics, or various types of Wolter optics and systems comprising combinations thereof. The high collection and focusing efficiency achievable using these optical elements in grazing incidence geometries (where total external reflection occurs) helps achieve high flux density in tightly focused spots.

Figure 1:
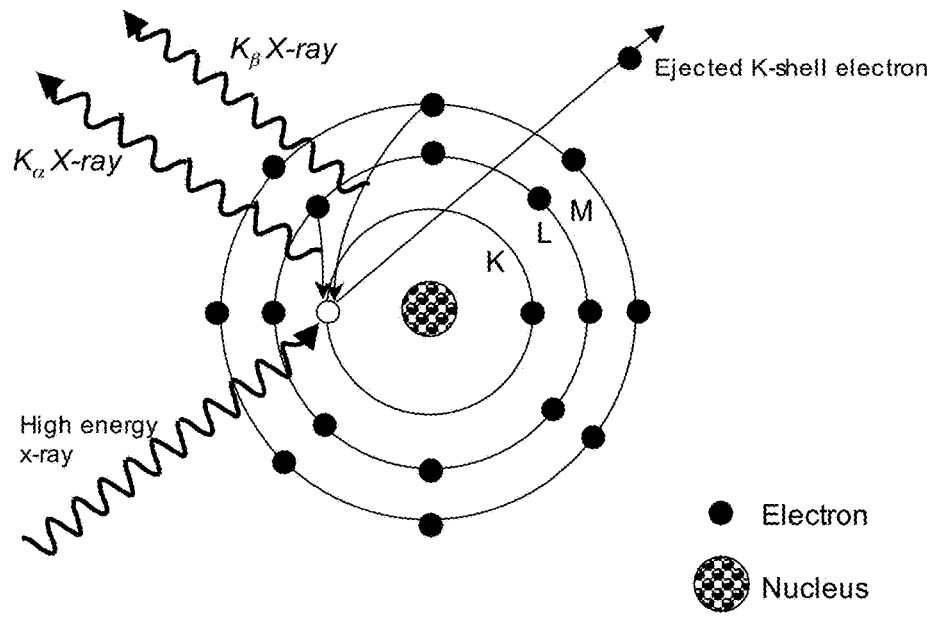
FIG. 1 illustrates the formation of x-ray fluorescence in an atom.

Note: Elements as shown in the drawings are meant to illustrate the functioning of embodiments of the invention, and should not be assumed to have been drawn in proportion or to scale.

DETAILED DESCRIPTIONS OF EMBODIMENTS OF THE INVENTION

1. A Basic Embodiment of the Invention

Figure 7:
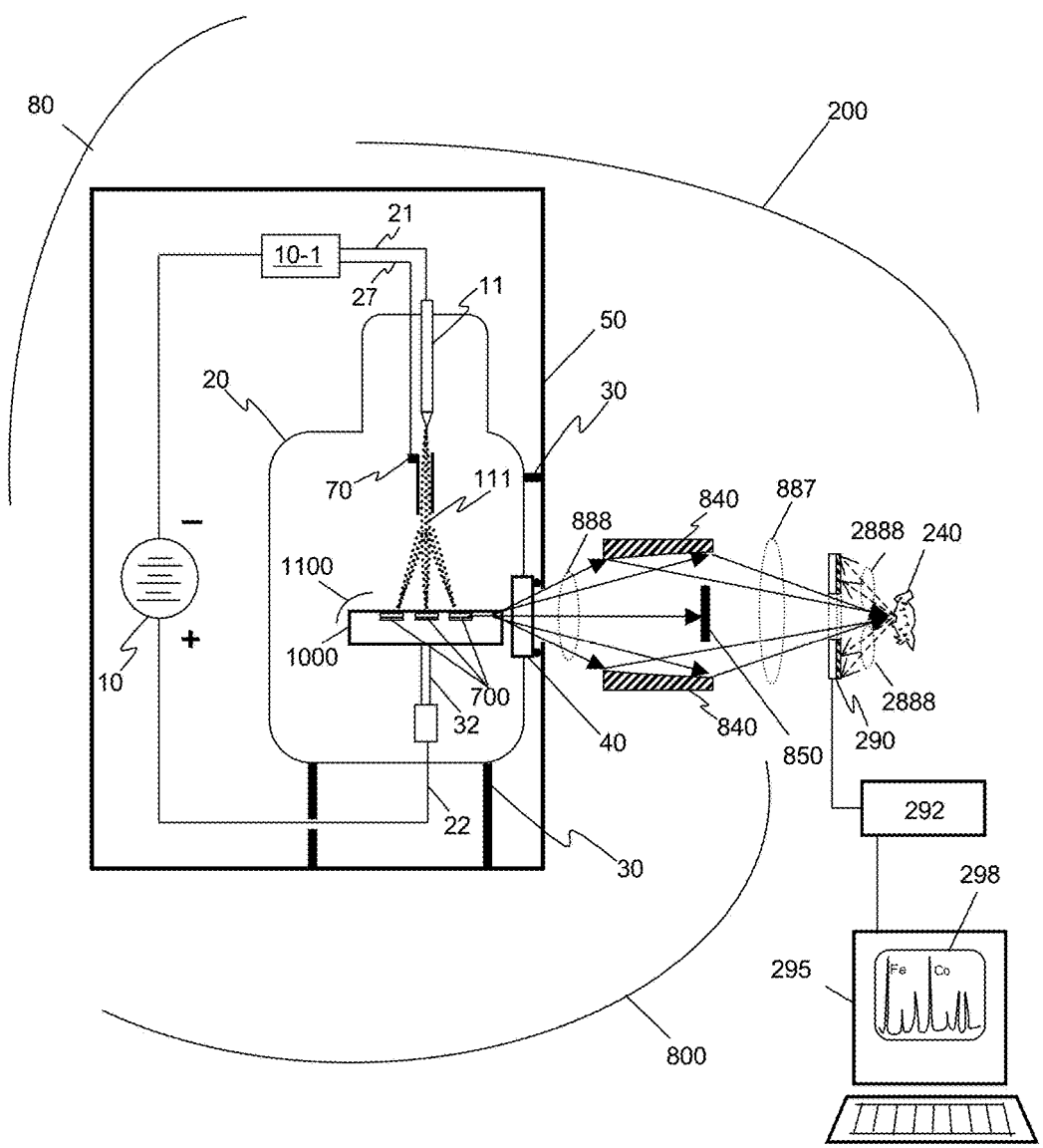
FIG. 7 illustrates a cross section view of a schematic illustration of an embodiment of the invention.

FIG. 7 illustrates an embodiment of an x-ray fluorescence system 200 comprising an illumination system according to the invention. The fluorescence system 200 comprises an illumination system 800 which comprises an x-ray source 80 and an x-ray optical train 840. The fluorescence system 200 additionally comprises a detector 290 with analysis electronics 295. The source 80 comprises a vacuum environment (typically $10^{-6}$ torr or better) commonly maintained by a sealed vacuum chamber 20 or active pumping, and manufactured with sealed electrical leads 21 and 22 that pass from the negative and positive terminals of a high voltage source 10 outside the tube to the various elements inside the vacuum chamber 20. The source 80 will typically comprise mounts 30 which secure the vacuum chamber 20 in a housing 50, and the housing 50 may additionally comprise shielding material, such as lead, to prevent x-rays from being radiated by the source 80 in unwanted directions.

Inside the vacuum chamber 20, an electron emitter 11 connected through the lead 21 to the negative terminal of a high voltage source 10, which serves as a cathode and generates a beam of electrons 111, often by running a current through a filament. Any number of prior art techniques for electron beam generation may be used for the embodiments of the invention disclosed herein. Additional known techniques used for electron beam generation include heating for thermionic emission, Schottky emission (a combination of heating and field emission), emitters comprising nanostructures such as carbon nanotubes), and by use of ferroelectric materials. [For more on electron emission options for electron beam generation, see Shigehiko Yamamoto, "Fundamental physics of vacuum electron sources", Reports on Progress in Physics vol. 69, pp. 181-232 (2006).]

A target 1100 comprising a target substrate 1000 and regions 700 of x-ray generating material is electrically connected to the opposite high voltage lead 22 and target support 32 to be at ground or a positive voltage relative to the electron emitter 11, thus serving as an anode. The electrons 111 accelerate towards the target 1100 and collide with it at high energy, with the energy of the electrons determined by the magnitude of the accelerating voltage. The collision of the electrons 111 into the target 1100 induces several effects, including the emission of x-rays 888, some of which exit the vacuum tube 20 and are transmitted through a window 40 that is transparent to x-rays.

In some embodiments of the invention, there may also be an electron control mechanism 70 such as an electrostatic lens system or other system of electron optics that is controlled and coordinated with the electron dose and voltage provided by the electron emitter 11 by a controller 10-1 through a lead 27. The electron beam 111 may therefore be scanned, focused, de-focused, or otherwise directed onto a target 1100 comprising one or more microstructures 700 fabricated to be in close thermal contact with a substrate 1000.

Once the x-rays 888 exit the source 80, a portion of the x-rays are collected by a set of x-ray optics, or optical train 840, typically comprising one or more optical elements having axial symmetry. The elements of this optical train 840 reflect x-rays at grazing angles to focus a portion 887 of the x-rays onto the object 240. X-rays that are not collected and focused may be blocked by a beam stop 850.

Once the focused portion of the x-rays 887 converge onto the object 240, x-ray fluorescence 2888 emitted from the illuminated region of the object 240 are collected by a detector 290. As in prior art systems, the detector 290 converts the detected counts to electronic signals, which may be further processed by signal processing electronics 292 and passed to an analysis system 295, which may comprise a display 298. The detector 290 commonly comprises sensors and electronics that serve as an x-ray spectrometer, analyzing both the number of x-ray fluorescence photons as well as their energy. Translation and rotation stages for the object 240 may also be provided, to allow different positions on the object 240 to be illuminated in a systematic scan or from several angles of incidence.

Figure 8:
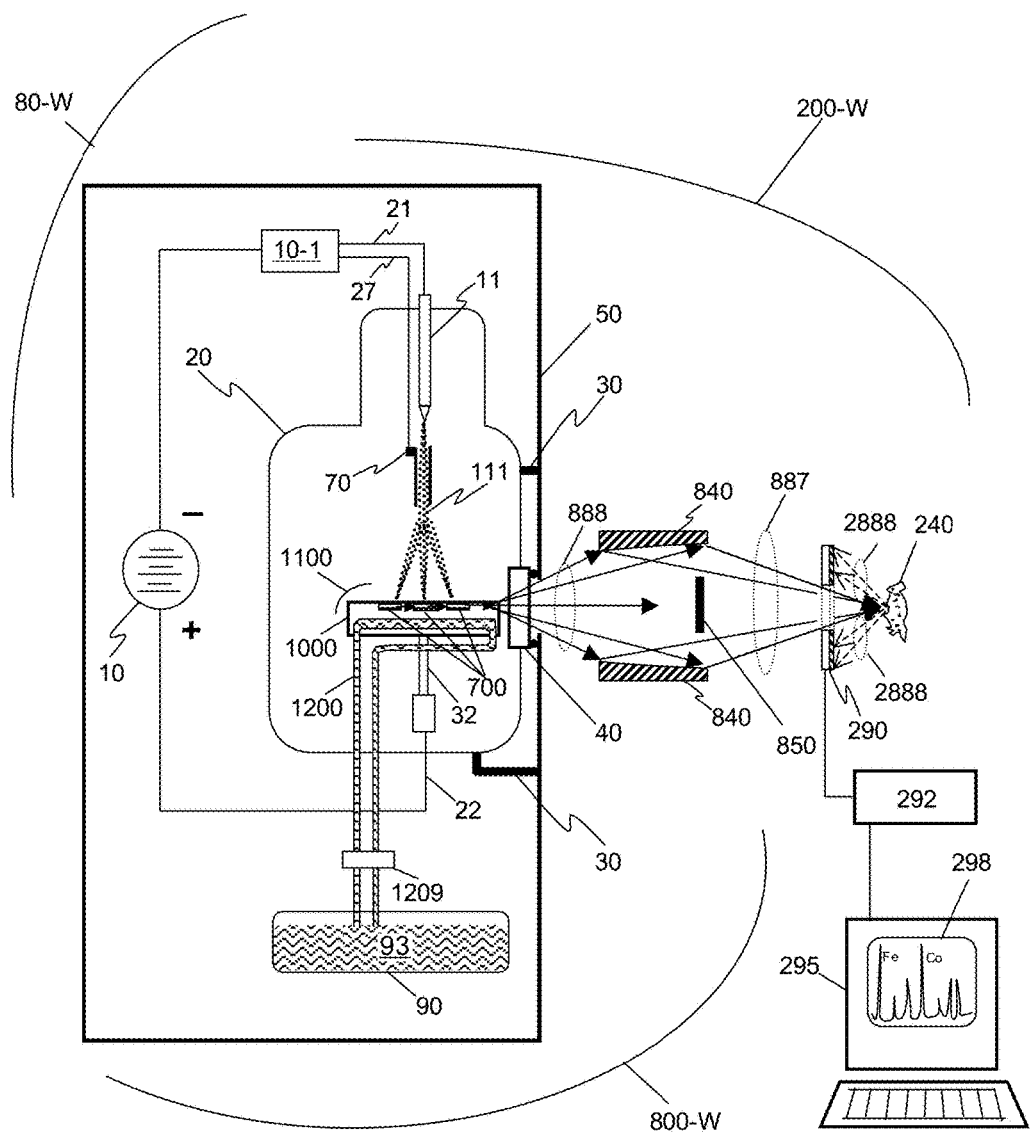
FIG. 8 illustrates a cross section view of a schematic illustration of an embodiment of the invention comprising a cooling system.

FIG. 8 illustrates an additional variation of this embodiment, in which the fluorescence system 200-W comprises an illumination system 800-W that additionally comprises source 80-W that additionally comprises a cooling system. The cooling system comprising a reservoir 90 filled with a cooling fluid 93, typically water, that is moved by means of a mechanism 1209 such as a pump through cooling channels 1200, including a cooling channel that passes through the substrate 1000 of the target 1100.

It should be noted that these illustrations are presented to aid in the understanding of the invention, and the various elements (microstructures, surface layers, cooling channels, etc.) are NOT drawn to scale in these figures.

2. Structured X-Ray Source

One objective of the invention is to provide a system for x-ray fluorescence measurements that is compact and has a high brightness x-ray source. One way to achieve this goal is to use x-ray targets in the system that comprise microstructured regions of x-ray generating material embedded into a thermally conductive substrate.

Microstructured targets such as those that may be used in embodiments of the invention disclosed herein have been described in detail in the US Patent Application entitled STRUCTURED TARGETS FOR X-RAY GENERATION (U.S. patent application Ser. No. 14/465,816, filed Aug. 21, 2014), which is hereby incorporated by reference in its entirety along with any provisional Applications to which this Patent Application claims benefit. Furthermore, sources using such structured targets are described more fully in the U.S. Patent Applications X-RAY SOURCES USING LINEAR ACCUMULATION (U.S. patent application Ser. No. 14/490,672 filed Sep. 19, 2014, now issued as U.S. Pat. No. 9,390,881), X-RAY SOURCES USING LINEAR ACCUMULATION (U.S. patent application Ser. No. 14/999,147, filed Apr. 1, 2016), and DIVERGING X-RAY SOURCES USING LINEAR ACCUMULATION (U.S. patent application Ser. No. 15/166,274 filed May 27, 2016), all of which are hereby incorporated by reference in their entirety, along with any provisional Applications to which these Patents and co-pending Patent Applications claim benefit. Any of the target and/or source designs and configurations disclosed in the above referenced Patents and Patent Applications may be considered for use as a component in any or all of the methods or systems disclosed herein.

As described herein and in the above cited pending Patent Applications, the target used in the source of x-rays may comprise a periodic array of sub-sources. Each sub-source may be comprised of a single or multiple microstructures of x-ray generating material in thermal contact with, or preferably embedded in, a substrate selected for its thermal conductivity. When the microstructures are in good thermal contact with a substrate having a high thermal conductivity, higher electron current densities may be used to generate x-rays, since the excess heat will be drawn away into the substrate. The higher current densities will give rise to higher x-ray flux, leading to a higher brightness source. As described in the above co-pending patent Applications, sources with microstructures of x-ray generating material may have a brightness more than 10 times larger than simpler constructions made from the same materials. Additional configurations in which multiple sub-sources are aligned to contribute x-rays on the same axis can multiply the brightness further through linear accumulation of the x-ray sub-sources.

It should also be noted here that, when the word "microstructure" is used herein, it is specifically referring to microstructures comprising x-ray generating material. Other structures, such as the cavities used to form the x-ray microstructures, have dimensions of the same order of magnitude, and might also be considered "microstructures". As used herein, however, other words, such as "structures", "cavities", "holes", "apertures", etc. may be used for these structures when they are formed in materials, such as the substrate, that are not selected for their x-ray generating properties. The word "microstructure" will be reserved for structures comprising materials selected for their x-ray generating properties.

Likewise, it should be noted that, although the word "microstructure" is used, x-ray generating structures with dimensions smaller than 1 micron, or even as small as nano-scale dimensions (i.e. greater than 10 nm) may also be described by the word "microstructures" as used herein as long as the properties are consistent with the geometric factors for sub-source size and grating pitches set forth in the various embodiments.

It should also be noted that here that, when the word "sub-source" is used it may refer to a single microstructure of x-ray generating material, or an ensemble of smaller microstructures that function similarly to a single structure.

The fabrication of these microstructured targets may follow well-known processing steps used for the creation of embedded structures in substrates. If the substrate is a material with high thermal conductivity such as diamond, conventional lithographic patterning using photoresists can produce micron sized structures, which may then be etched into the substrate using processes such as reactive ion etching (RIE). Deposition of the x-ray generating material into the etched structures formed in the substrate may then be carried out using standard deposition processes, such as electroplating, chemical vapor deposition (CVD), atomic layer deposition, or mechanical pressing.

The x-ray generating material used in the target should ideally have good thermal properties, such as a high melting point and high thermal conductivity, in order to allow higher electron power loading on the source to increase x-ray production. The x-ray generating material should additionally be selected for good x-ray production properties, which includes x-ray production efficiency (proportional to its atomic number) and in some cases, it may be desirable to produce a specific spectra of interest, such as a characteristic x-ray spectral line. For these reasons, targets are often fabricated using tungsten, with an atomic number Z=74.

Table II lists several materials that are commonly used for x-ray targets, several additional potential target materials (notably useful for specific characteristic lines of interest), and some materials that may be used as substrates for target materials. Melting points, and thermal and electrical conductivities are presented for values near 300° K (27° C.). Most values are cited from the *CRC Handbook of Chemistry and Physics*, 90$^{th}$ ed. (CRC Press, Boca Raton, Fla., 2009). Other values are cited from various sources found on the Internet. Note that, for some materials, such as sapphire for example, thermal conductivities an order of magnitude larger may be possible when cooled to temperatures below that of liquid nitrogen (77° K) [see, for example, Section 2.1.5, *Thermal Properties*, of E. R. Dobrovinskaya et al., *Sapphire: Material, Manufacturing, Applications*, Springer Science+Business Media, L L C, 2009]

Figure 9:
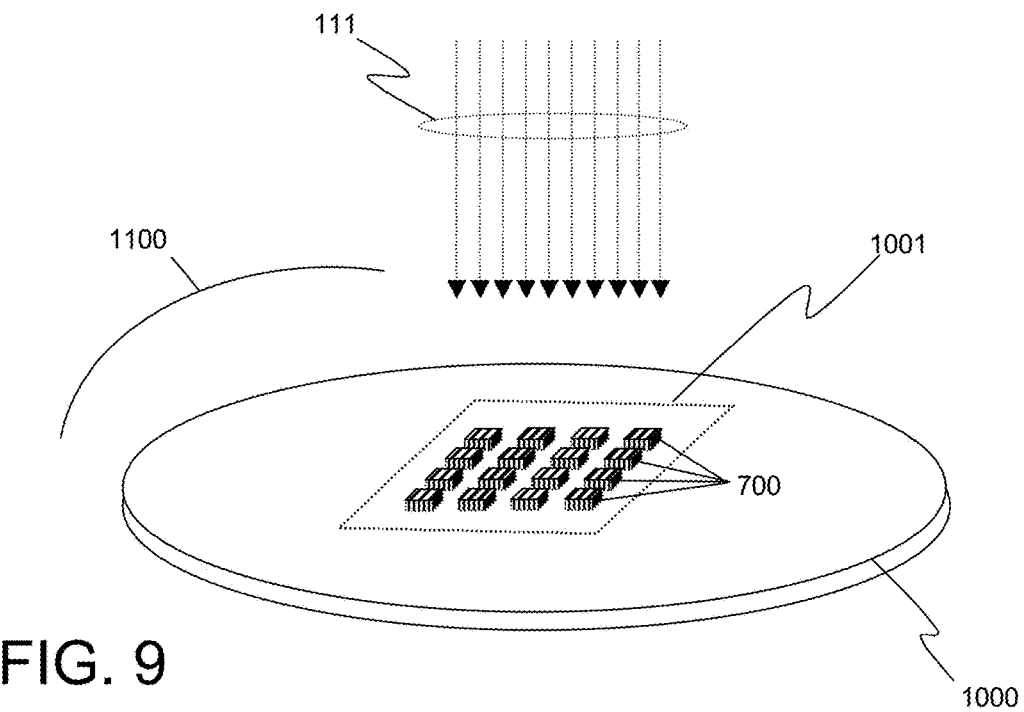
FIG. 9 illustrates a perspective view of a target comprising a grid of embedded rectangular target microstructures on a larger substrate that may be used in some embodiments of the invention.

FIG. 9 illustrates a target 1100 as may be used in some embodiments of the invention. In this figure, a substrate 1000 has a region 1001 that comprises an array of microstructures 700 comprising x-ray generating material (typically a metallic material) that are arranged in a regular array of right rectangular prisms. In a vacuum, electrons 111 bombard the target from above, and generate heat and x-rays in the microstructures 700. The material in the substrate 1000 is selected such that it has relatively low energy deposition rate for electrons in comparison to the x-ray generating microstructure material (typically by selecting a low Z material for the substrate), and therefore will not generate a significant amounts of heat and x-rays.

The material of the substrate 1000 may also be chosen to have a high thermal conductivity, typically larger than 100 W/(m ° C.) at room temperature, and the microstructures are typically embedded within the substrate, i.e. if the microstructures are

TABLE II

Various Target and Substrate Materials and Selected Properties.

| Material (Elemental Symbol) | Atomic Number Z | Melting Point ° C. (1 atm) | Thermal Conductivity (W/(m ° C.)) | Electrical Conductivity (MS/m) |
| --- | --- | --- | --- | --- |
| Common Target Materials: | | | | |
| Chromium (Cr) | 24 | 1907 | 93.7 | 7.9 |
| Iron (Fe) | 26 | 1538 | 80.2 | 10.0 |
| Cobalt (Co) | 27 | 1495 | 100 | 17.9 |
| Copper (Cu) | 29 | 1085 | 401 | 58.0 |
| Molybdenum (Mo) | 42 | 2623 | 138 | 18.1 |
| Silver (Ag) | 47 | 962 | 429 | 61.4 |
| Tungsten (W) | 74 | 3422 | 174 | 18.4 |
| Other Possible Target Materials: | | | | |
| Titanium (Ti) | 22 | 1668 | 21.9 | 2.6 |
| Gallium (Ga) | 35 | 30 | 40.6 | 7.4 |
| Rhodium (Rh) | 45 | 1964 | 150 | 23.3 |
| Indium (In) | 49 | 157 | 81.6 | 12.5 |
| Cesium (Cs) | 55 | 28 | 35.9 | 4.8 |
| Rhenium (Re) | 75 | 3185 | 47.9 | 5.8 |

TABLE II-continued

Various Target and Substrate Materials and Selected Properties.

| Material (Elemental Symbol) | Atomic Number Z | Melting Point ° C. (1 atm) | Thermal Conductivity (W/(m ° C.)) | Electrical Conductivity (MS/m) |
|---|---|---|---|---|
| Gold (Au) | 79 | 1064 | 317 | 44.0 |
| Lead (Pb) | 82 | 327 | 35.3 | 4.7 |
| Other Potential Substrate Materials with low atomic number: | | | | |
| Beryllium (Be) | 4 | 1287 | 200 | 26.6 |
| Carbon (C): Diamond | 6 | * | 2300 | $10^{-19}$ |
| Carbon (C): Graphite ∥ | 6 | * | 1950 | 0.25 |
| Carbon (C): Nanotube (SWNT) | 6 | * | 3180 | 100.0 |
| Carbon (C): Nanotube (bulk) | 6 | * | 200 | |
| Boron Nitride (BN) | B = 5 N = 7 | ** | 20 | $10^{-17}$ |
| Silicon (Si) | 14 | 1414 | 124 | $1.56 \times 10^{-9}$ |
| Silicon Carbide (β-SiC) | Si = 14 C = 6 | 2798 | 0.49 | $10^{-9}$ |
| Sapphire (Al$_2$O$_3$) ∥ C | Al = 13 O = 8 | 2053 | 32.5 | $10^{-20}$ |

*Carbon does not melt at 1 atm; it sublimes at ~3600° C.
**BN does not melt at 1 atm; it sublimes at ~2973° C.

shaped as rectangular prisms, it is preferred that at least five of the six sides are in close thermal contact with the substrate 1000, so that heat generated in the microstructures 700 is effectively conducted away into the substrate 1000. However, targets used in other embodiments may have fewer direct contact surfaces. In general, when the term "embedded" is used in this disclosure, at least half of the surface area of the microstructure will be in close thermal contact with the substrate.

Figure 10:
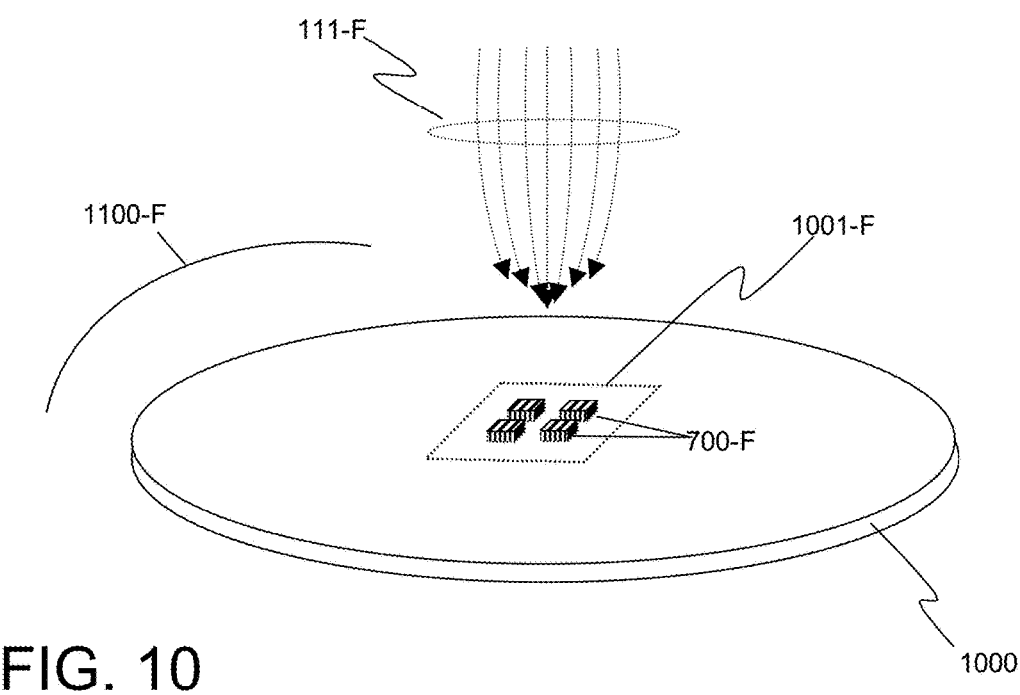
FIG. 10 illustrates a perspective view of a variation of a target comprising a grid of embedded rectangular target microstructures on a larger substrate for use with focused electron beam that may be used in some embodiments of the invention.

FIG. 10 illustrates another target 1100-F as may be used in some embodiments of the invention in which the electron beam 111-F is directed by electrostatic lenses to form a more concentrated, focused spot. For this situation, the target 1100-F will still comprise a region 1001-F comprising an array of microstructures 700-F comprising x-ray generating material, but the size and dimensions of this region 1001-F can be matched to regions where electron exposure will occur. In these targets, the "tuning" of the source geometry and the x-ray generating material can be controlled such that the designs mostly limit the amount of heat generated to the microstructured region 1001-F, while also reducing the design and manufacturing complexity. This may be especially useful when used with electron beams focused to form a micro-spot, or by more intricate systems that form a more complex electron exposure pattern.

Figure 11:
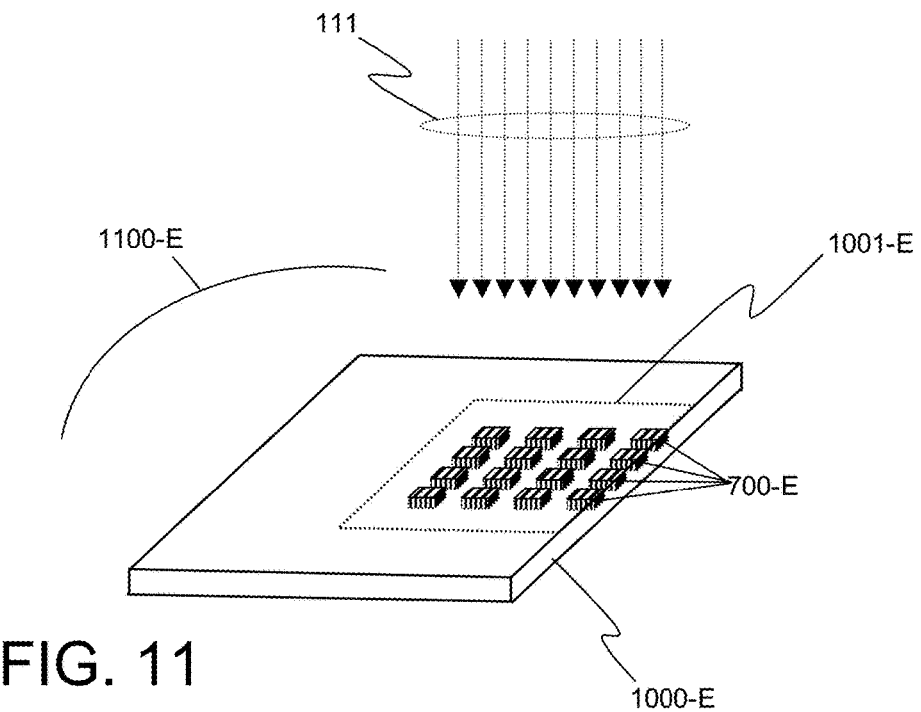
FIG. 11 illustrates a perspective view of a variation of a target comprising a grid of embedded rectangular target microstructures on a truncated substrate as may be used in some embodiments of the invention.

FIG. 11 illustrates another target 1100-E as may be used in some embodiments of the invention, in which the target 1100-E still has a region 1001-E with an array of microstructures 700-E comprising x-ray generating material that generates x-rays when exposed to electrons 111, but the region 1001-E is positioned flush with or near the edge of the substrate 1000-E. This configuration may be useful in targets where the substrate comprises a material that absorbs x-rays, and so emission at near-zero angles would be significantly attenuated in a configuration as was shown in FIG. 9.

A disadvantage of the target of FIG. 11, however, as compared to FIG. 9 is that a significant portion of the substrate on one side of the microstructures 700-E is gone. Heat therefore is not carried away from the microstructures symmetrically, and the local heating may increase, impairing heat flow.

Figure 12:
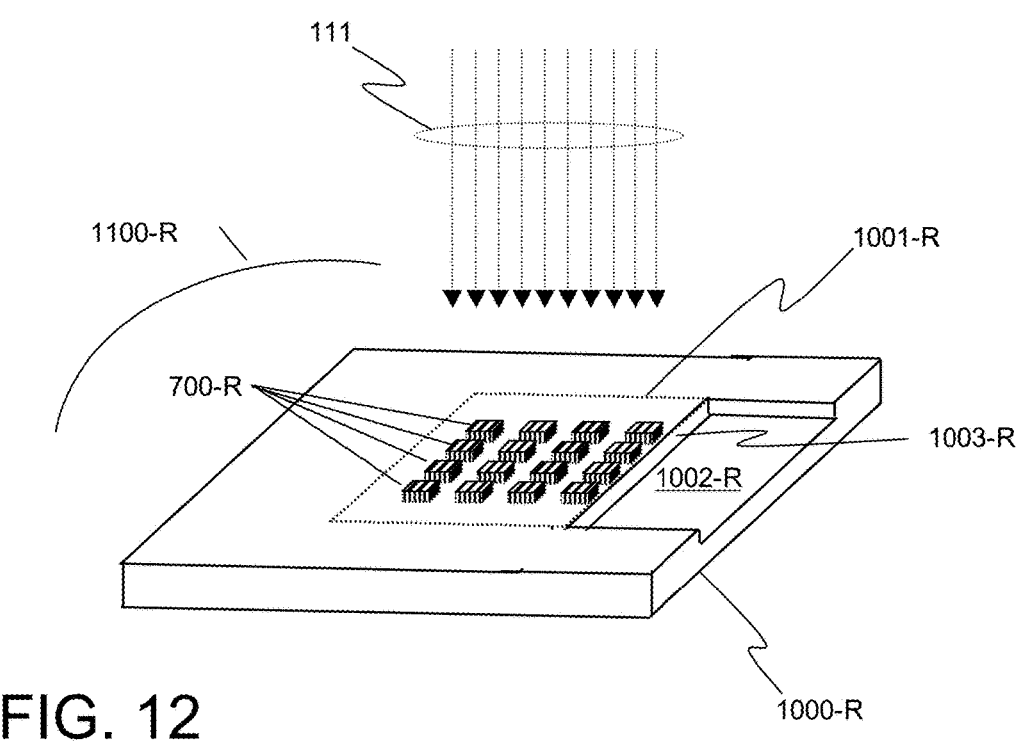
FIG. 12 illustrates a perspective view of a variation of a target comprising a grid of embedded rectangular target microstructures on a substrate with a recessed shelf that may be used in some embodiments of the invention.

To address this, some targets as may be used in some embodiments of the invention may use a configuration like that shown in FIG. 12. Here, the target 1100-R comprises a substrate 1000-R with a recessed shelf 1002-R. This allows the region 1001-R comprising an array of microstructures 700-R to be positioned flush with, or close to, a recessed edge 1003-R of the substrate, and generate x-rays at or near zero angle without being reabsorbed by the substrate 1000-R, yet provides a more symmetric heat sink for the heat generated when exposed to electrons 111.

The depth of penetration for electrons into the target can be estimated by Potts' Law [P. J. Potts, Electron Probe Microanalysis, Ch. 10 of *A Handbook of Silicate Rock Analysis*, Springer Netherlands, 1987, p. 336)]. Using this formula, Table III illustrates some of the estimated penetration depths for some common x-ray target materials.

TABLE III

Estimates of penetration depth for 60 keV electrons into some materials.

| Material | Z | Density (g/cm$^3$) | Penetration Depth (μm) |
|---|---|---|---|
| Diamond | 6 | 3.5 | 13.28 |
| Copper | 29 | 8.96 | 5.19 |
| Molybdenum | 42 | 10.28 | 4.52 |
| Tungsten | 74 | 19.25 | 2.41 |

As an example, if 60 keV electrons are used, and diamond (Z=6) is selected as the material for the substrate 1000 and copper (Z=29) is selected as the x-ray generating material for the microstructures 700, approximately ⅔ of the penetration depth in the substrate corresponds to a dimension of ~10 microns, and the depth D in the x-ray generating material, which, when set to be ⅔ (66%) of the electron penetration depth for copper, becomes D 3.5 μm.

The majority of characteristic Cu K x-rays are generated within depth D. The electron interactions below that depth typically generate few characteristic K-line x-rays but will contribute to the heat generation, thus resulting in a low thermal gradient along the depth direction. It is therefore preferable in some embodiments to set a maximum thickness for the microstructures in the target in order to limit electron interaction in the material and optimize local thermal gradients. One embodiment of the invention limits the depth of the microstructured x-ray generating material in the target to between one third and two thirds of the electron penetration depth at the incident electron energy. In this case, the lower mass density of the substrate leads to a lower energy deposition rate in the substrate material immediately below the x-ray generating material, which in turn leads to a lower temperature in the substrate material below. This results in a higher thermal gradient between the x-ray generating material and the substrate, enhancing heat transfer. The thermal gradient is further enhanced by the high thermal conductivity of the substrate material.

For similar reasons, selecting the depth D to be less than the electron penetration depth is also generally preferred for efficient generation of bremsstrahlung radiation, because the electrons below that depth have lower energy and thus lower x-ray production efficiency.

Note: Other choices for the dimensions of the x-ray generating material may also be used. In targets as used in some embodiments of the invention, the depth of the x-ray generating material may be selected to be 50% of the electron penetration depth. In other embodiments, the depth of the x-ray generating material may be selected to be 33% of the electron penetration depth. In other embodiments, the depth D for the microstructures may be selected related to the "continuous slowing down approximation" (CSDA) range for electrons in the material. Other depths may be specified depending on the x-ray spectrum desired and the properties of the selected x-ray generating material.

Note: In other targets as may be used in some embodiments of the invention, a particular ratio between the depth and the lateral dimensions (such as width W and length L) of the x-ray generating material may also be specified. For example, if the depth is selected to be a particular dimension D, then the lateral dimensions W and/or L may be selected to be no more than 5×D, giving a maximum ratio of 5. In other targets as may be used in some embodiments of the invention, the lateral dimensions W and/or L may be selected to be no more than 2×D. It should also be noted that the depth D and lateral dimensions W and L (for width and length of the x-ray generating microstructure) may be defined relative to the axis of electron propagation, or defined with respect to the orientation of the surface of the x-ray generating material. For normal incidence electrons, these will be the same dimensions. For electrons incident at an angle, care must be taken to make sure the appropriate projections are used.

Up to this point, targets that are arranged in planar configurations have been presented. These are generally easier to implement, since equipment and process recipes for deposition, etching and other planar processing steps are well known from processing devices for microelectromechanical systems (MEMS) applications using planar diamond, and from processing silicon wafers for the semiconductor industry.

However, in some embodiments, a target with a surface with additional properties in three dimensions (3-D) may be desired. As discussed previously, when the electron beam is larger than the electron penetration depth, the apparent x-ray source size and area is at minimum (and brightness maximized) when viewed parallel to surface, i.e. at a zero degree (0°) take-off angle. As a consequence, the apparent brightest of x-ray emission occurs when viewed at 0° take-off angle. The emission from within the x-ray generating material will accumulate as it propagates at 0° through the material.

With an extended target of substantially uniform material, the attenuation of x-rays between their points of origin inside the target as they propagate through the material to the surface increases with decreasing take-off angle, due to the longer distance traveled within the material, and often becomes largest at or near 0° take-off angle. Reabsorption may therefore counterbalance any increased brightness that viewing at near 0° achieves. The distance through which an x-ray beam will be reduced in intensity by 1/e is called the x-ray attenuation length, and therefore, a configuration in which the generated x-rays pass through as little additional material as possible, with the distance selected to be related to the x-ray attenuation length, may be desired.

Figure 13:
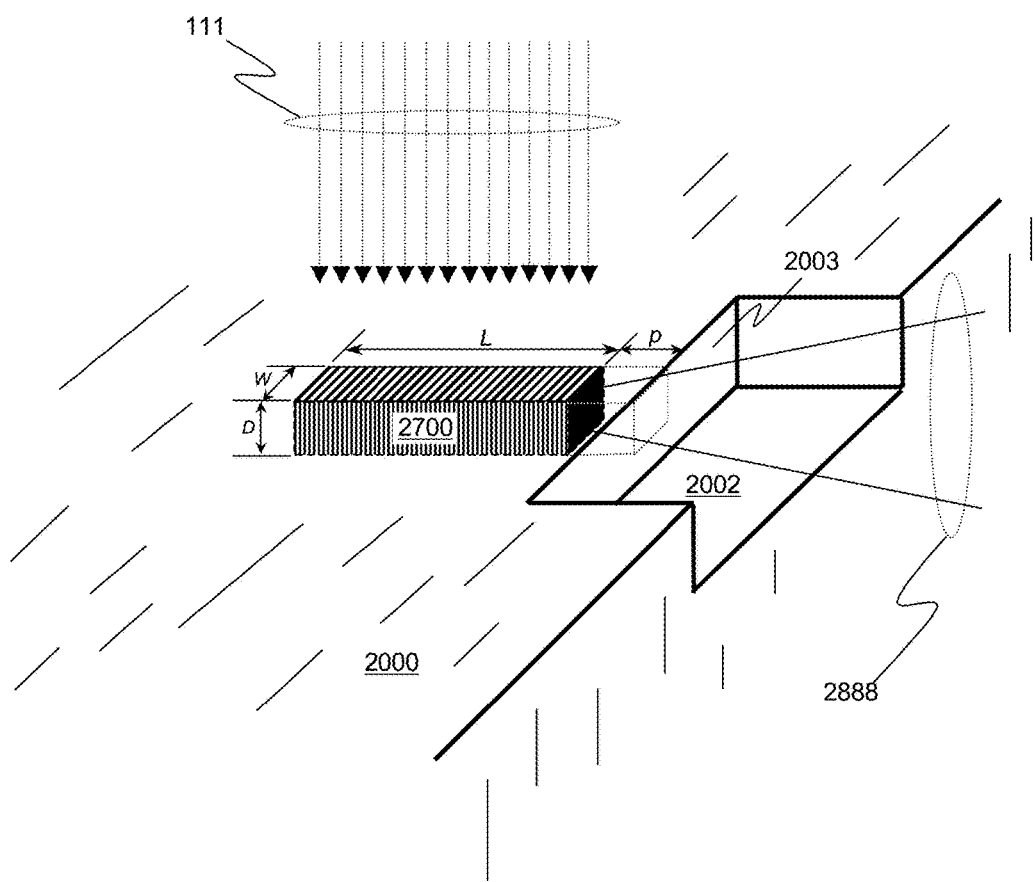
FIG. 13 illustrates a perspective view of a target comprising a single rectangular microstructure arranged on a substrate with a recessed region that may be used in some embodiments of the invention.

An illustration of a portion of a target as may be used in some embodiments of the invention is presented in FIG. 13, in which an x-ray generating region comprising a single microstructure 2700 is configured at or near a recessed edge 2003 of the substrate on a shelf 2002, similar to the situation illustrated in FIG. 12. The x-ray generating microstructure 2700 is in the shape of a rectangular bar of width W, length L, and depth or thickness D that is embedded in the substrate 2000 and generates x-rays 2888 when bombarded with electrons 111.

The thickness of the bar D (along the surface normal of the target) is selected to be between one third and two thirds of the electron penetration depth of the x-ray generating material at the incident electron energy for optimal thermal performance. It may also be selected to obtain a desired x-ray source size in the vertical direction. The width of the bar W is selected to obtain a desired source size in the corresponding direction. As illustrated, W≈1.5 D, but could be substantially smaller or larger, depending on the size of the source spot desired.

The length of the bar L as illustrated is L≈4 D, but may be any dimension, and may typically be determined to be between ¼ to 3 times the x-ray attenuation length for the selected x-ray generating material. The distance between the edge of the shelf and the edge of the x-ray generating material p as illustrated is p≈W, but may be selected to be any value, from flush with the edge 2003 (p=0) to as much as 1 mm, depending on the x-ray reabsorption properties of the substrate material, the relative thermal properties, and the amount of heat expected to be generated when bombarded with electrons.

Figure 14:
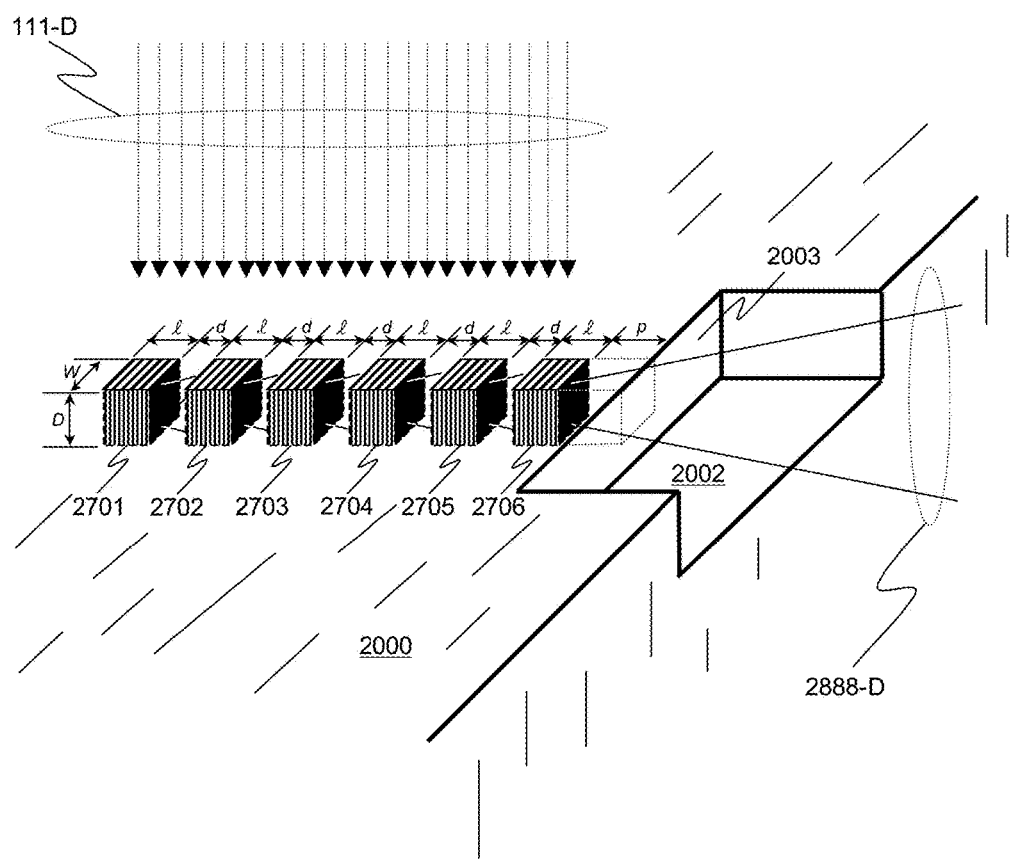
FIG. 14 illustrates a perspective view of a target comprising a multiple rectangular microstructure arranged in a line on a substrate with a recessed region that may be used in some embodiments of the invention.

An illustration of a portion of an alternative target as may be used in some embodiments of the invention is presented in FIG. 14. In this target, an x-ray generating region with six microstructures 2701, 2702, 2703, 2704, 2705, 2706 is configured at or near a recessed edge 2003 of the target substrate 2000 on a shelf 2002, similar to the situation illustrated in FIG. 12 and FIG. 13. As shown, the x-ray generating microstructures 2701, 2702, 2703, 2704, 2705, 2706 are arranged in a linear array of x-ray generating right rectangular prisms embedded in the substrate 2000, and generate x-rays 2888-D when bombarded with electrons 111.

In this target as may be used in some embodiments of the invention, the total volume of x-ray generating material is the same as in the previous illustration of FIG. 13. The thickness D of the microstructures 2701-2706 (along the surface normal of the target) is selected to be between one third and two thirds of the electron penetration depth of the x-ray generating material at the incident electron energy for optimal thermal performance, as in the case shown in FIG. 13. The width W of the microstructures 2701-2706 is selected to obtain a desired source size in the corresponding direction and as illustrated, W≈1.5 D, as in the case shown in FIG. 13. As discussed previously, it could also be substantially smaller or larger, depending on the size of the source spot desired.

However, as shown in FIG. 14, the single bar 2700 of length L as illustrated in FIG. 13 has been replaced with microstructures 2701, 2702, 2703, 2704, 2705, 2706 in the form of 6 sub-bars, each of length l=L/6. Although the volume of x-ray generation (when bombarded with the same electron density) will be the same, each sub-bar now has five faces transferring heat into the substrate, increasing the heat transfer away from the x-ray generating sub-bars 2701-2706 and into the substrate. As illustrated, the separation between the sub-bars is a distance d≈l, although larger or smaller dimensions may also be used, depending on the amount of x-rays absorbed by the substrate and the relative thermal gradients that may be achieved between the specific materials of the x-ray generating microstructures 2701-2706 and the substrate 2000.

Likewise, the distance between the edge of the shelf and the edge of the x-ray generating material p as illustrated is p≈W, but may be selected to be any value, from flush with the edge 2003 (p=0) to as much as 1 mm, depending on the x-ray reabsorption properties of the substrate material, the relative thermal properties, and the amount of heat expected to be generated when bombarded with electrons.

For a configuration such as shown in FIG. 14, the total length of the x-ray generating sub-bars will commonly be about twice the linear attenuation length for x-rays in the x-ray generating material, but can be selected from half to more than 3 times that distance. Likewise, the thickness D of the sub-bars (along the surface normal of the target) was selected to be equal to one-third to two-thirds of the electron penetration depth of the x-ray generating material at the incident electron energy for optimal thermal performance, but it can be substantially larger. It may also be selected to obtain a desired x-ray source size in that direction which is approximately equal.

The bars may be embedded in the substrate (as shown), but if the thermal load generated in the x-ray generating material is not too large, they may also be placed on top of the substrate.

Microstrutures may be embedded with some distance to the edges of the staircase, as illustrated in FIGS. 9 and 10, or flush with as edge (as was shown in FIG. 11). A determination of which configuration is appropriate for a specific application may depend on the exact properties of the x-ray generating material and substrate material, so that, for example, the additional brightness achieved with increased electron current enabled by the thermal transfer through five vs. four surfaces may be compared with the additional brightness achieved with free space emission vs. reabsorption through a section of substrate material. The additional costs associated with the alignment and overlay steps, as well as the multiple processing steps that may be needed to pattern multiple prisms on multiple layers, may need to be considered in comparison to the increased brightness achievable.

An alternative target as may be used in some embodiments of the invention may have several microstructures of right rectangular prisms simply deposited upon the surface of the substrate. In this case, only the bottom base of the prism would be in thermal contact with the substrate. For a structure comprising the microstructures embedded in the substrate with a side/cross-section view as shown in FIGS. 13 and 14 with depth D and lateral dimensions in the plane of the substrate of W and L (or l), the ratio of the total surface area in contact with the substrate for the embedded microstructures vs. deposited microstructures is $$\frac{A_{Embedded}}{A_{Deposited}} = 1 + 2D\frac{(W + L)}{(W \times L)} \quad [\text{Eqn. 9}]$$

With a small value for D relative to W and L, the ratio is essentially 1. For larger thicknesses, the ratio becomes larger, and for a cube (D=W=L) in which 5 equal sides are in thermal contact, the ratio is 5. If a cap layer of a material with similar properties as the substrate in terms of mass density and thermal conductivity is used, the ratio may be increased to 6.

The amount of heat transferred per unit time (ΔQ) conducted through a material of area A and thickness d given by:

$$\Delta Q = \frac{\kappa \cdot A \cdot \Delta T}{d} \quad [\text{Eqn. 10}]$$

where κ is the thermal conductivity in W/(m ° C.) and ΔT is the temperature difference across thickness d in ° C. Therefore, an increase in surface area A, a decrease in thickness d and an increase in ΔT all lead to a proportional increase in heat transfer.

Figure 15:
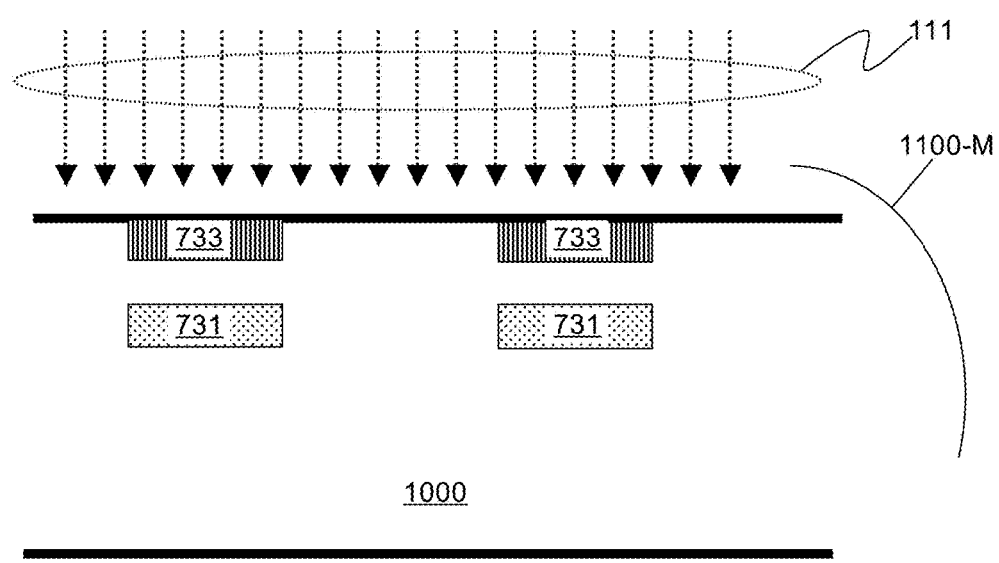
FIG. 15 illustrates a cross section schematic view of a target structure as used in some embodiments of the invention.

Other target configurations that may be used in embodiments of the invention, as has been described in the above cited U.S. patent application Ser. No. 14/465,816, are microstructures comprising multiple x-ray generating materials, microstructures comprising alloys of x-ray generating materials, microstructures deposited with an anti-diffusion layer or an adhesion layer, microstructures with a thermally conducting overcoat, microstructures with a thermally conducting and electrically conducting overcoat, microstructures buried within a substrate and the like. FIG. 15 illustrates a target 1100-M comprising a substrate 1000 and microstructures 731 buried within the substrate 1000, along with microstructures 733 embedded within the substrate 1000, with the entire target 1100-M being irradiated by an electron beam 111. Buried microstructures 731 and embedded microstructures 733 may in some embodiments comprise the same x-ray generating material, or, in other embodiments, different x-ray generating materials.

Other target configurations that may be used in embodiments of the invention, as has been described in the above cited U.S. patent application Ser. No. 14/465,816, are arrays of microstructures that may comprise any number of conventional x-ray target materials (such as copper (Cu) and molybdenum (Mo) and tungsten (W)) that are patterned as features of micron scale dimensions on (or embedded in) a thermally conducting substrate, such as diamond or sapphire. In some embodiments, the microstructures may alternatively comprise unconventional x-ray target materials, such as tin (Sn), sulfur (S), titanium (Ti), antimony (Sb), etc. that have thus far been limited in their use due to poor thermal properties.

Other target configurations that may be used in embodiments of the invention, as has been described in the above cited U.S. patent application Ser. No. 14/465,816, are arrays of microstructures that take any number of geometric shapes, such as cubes, rectangular blocks, regular prisms, right rectangular prisms, trapezoidal prisms, spheres, ovoids, barrel shaped objects, cylinders, triangular prisms, pyramids, tetrahedra, or other particularly designed shapes, including those with surface textures or structures that enhance surface area, to best generate x-rays of high brightness and that also efficiently disperse heat.

Other target configurations that may be used in embodiments of the invention, as has been described in the above cited U.S. patent application Ser. No. 14/465,816, are arrays of microstructures comprising various materials as the x-ray generating materials, including aluminum, titanium, vanadium, chromium, manganese, iron, cobalt, nickel, copper, gallium, zinc, yttrium, zirconium, molybdenum, niobium, ruthenium, rhenium, rhodium, palladium, silver, tin, iridium, tantalum, tungsten, indium, cesium, barium, gold, platinum, lead and combinations and alloys thereof The embodiments described so far include a variety of x-ray target configurations that comprise a plurality of microstructures comprising x-ray generating material that can be used as targets in x-ray sources to generate x-rays with increased brightness. These target configurations have been described as being bombarded with electrons and generating x-rays, but may be used as the static x-ray target in an otherwise conventional source.

It is also possible that the targets described above may be embodied in a moving x-ray target, replacing, for example, the target in a rotating anode x-ray source with a microstructured target as described above and in the cited co-pending patent applications to create a source with a moving microstrucutred target in accord with other embodiments of the invention.

3. X-Ray Optical System

Once x-rays are generated by a high-brightness x-ray source, a portion of the x-rays can be collected by an optical system, to be subsequently collimated and/or focused onto the object to generate fluorescence.

Figure 16A:
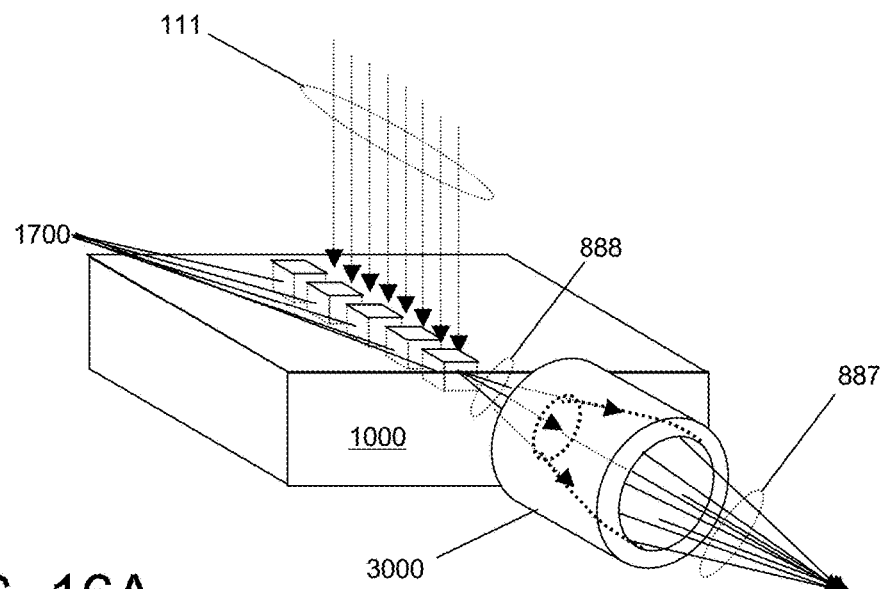
FIG. 16A illustrates a conceptual perspective view of an embodiment of the invention.
Figure 16B:
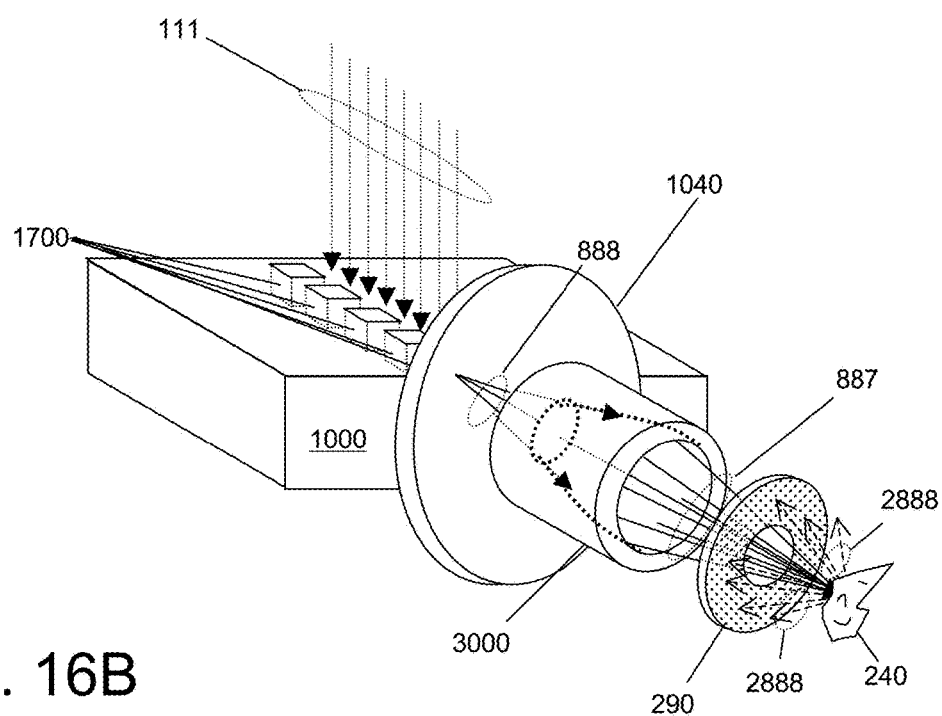
FIG. 16B illustrates a conceptual perspective view of the embodiment of the invention of FIG. 15A with additional details shown.

FIGS. 16A and 16B illustrates an x-ray source comprising a number of microstructures 1700 of x-ray generating material embedded in a substrate 1000 that are bombarded by electrons 111. The microstructures 1700 are aligned so that the x-rays generated by the microstructures accumulate along the axis of orientation. In the illustration, only 5 microstructures 1700 are shown embedded in the substrate, but an actual x-ray source may comprise any number of microstructures to allow more x-rays to be generated and accumulated.

The generated x-rays 888 will be diverging from the source, and after passing from the source through an x-ray transparent window 1040 to exit the vacuum chamber (not shown in FIG. 16A), a set of one or more x-ray optical elements will intersect a portion of the x-rays and redirect their path of propagation. In FIGS. 16A and 16B, a single x-ray reflecting optical element 3000 with the topology of a hollow tube is illustrated. This optical element 3000 can be mounted along the axis of brightest illumination so that a portion of the diverging x-rays 888 will reflect off the inner surface of the optical element 3000. The curvature of the inner surface may take a number of geometric forms, but a very useful set of geometric forms for a number of optical elements are found among the quadric surfaces, and in particular, spheroids, ellipsoids, paraboloids, hyperboloids, elliptic cylinders, circular cylinders, elliptic cones, and circular cones.

These optical elements 3000 will typically be mounted such that a portion of the x-rays experience total external reflection from the inner surface, as was described above. The reflected x-rays 887 may be focused to a point (as illustrated), or collimated, or some other diverging or converging configuration.

Figure 2:
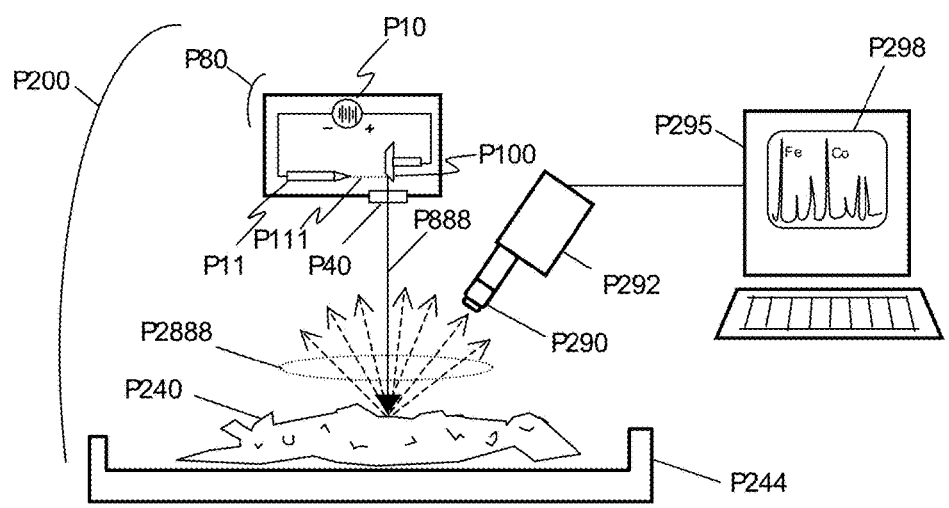
FIG. 2 illustrates the elements of a prior art x-ray fluorescence system.
Figure 3A:
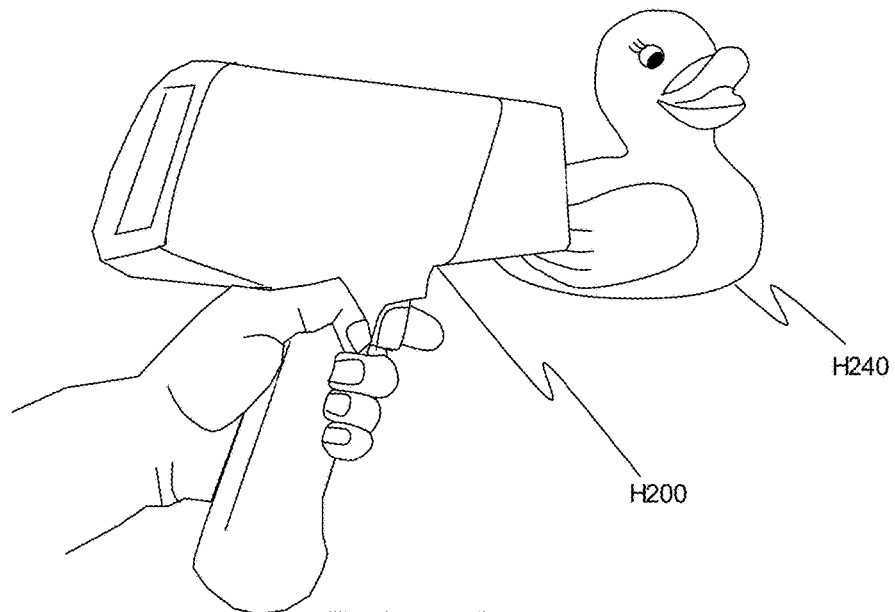
FIG. 3A illustrates a handheld prior art x-ray fluorescence system.
Figure 3B:
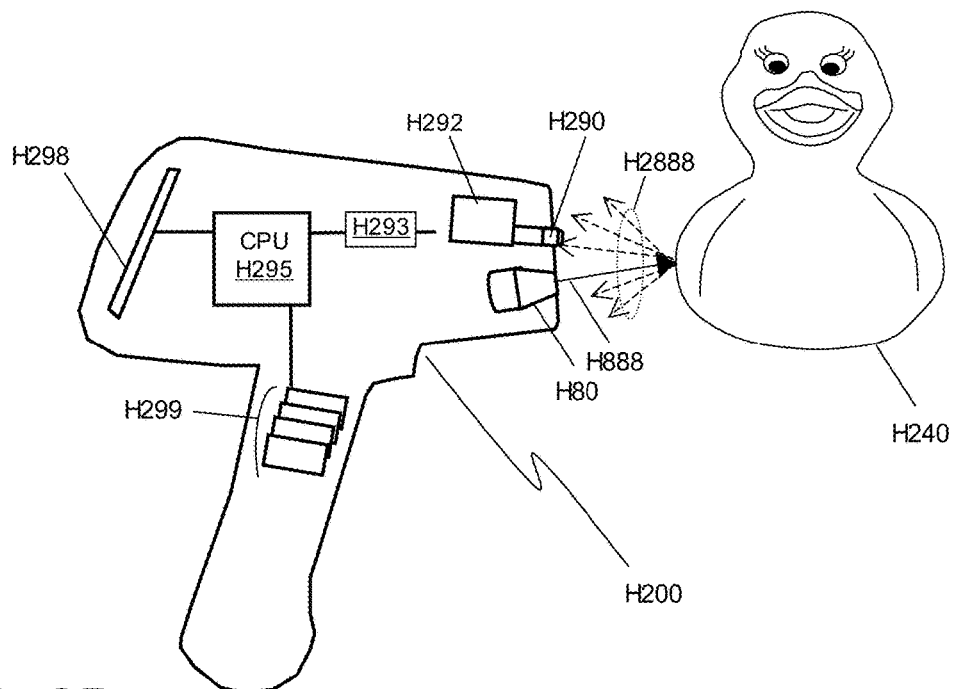
FIG. 3B illustrates a schematic view of a handheld prior art x-ray fluorescence system.
Figure 4:
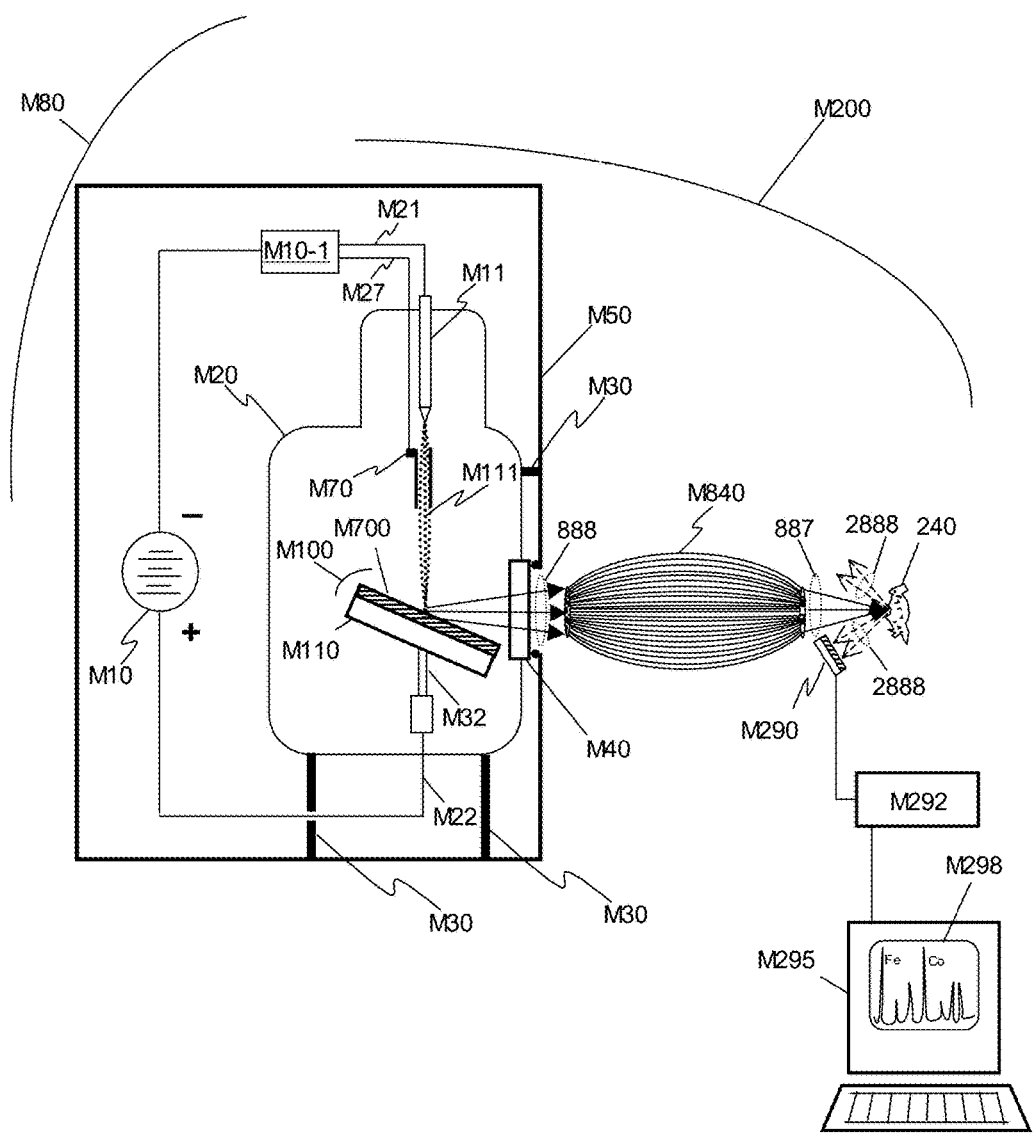
FIG. 4 illustrates a cross section view of a prior art x-ray fluorescence system.
Figure 5:
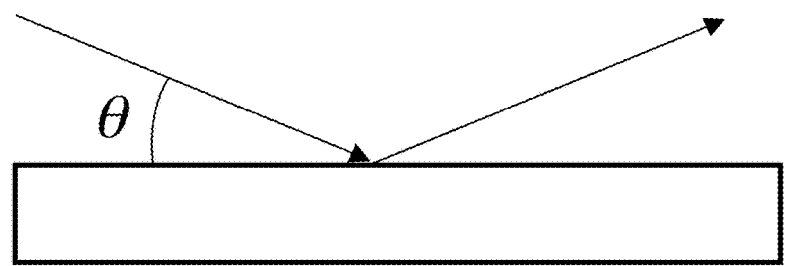
FIG. 5 illustrates x-ray reflection from a surface.
Figure 6:
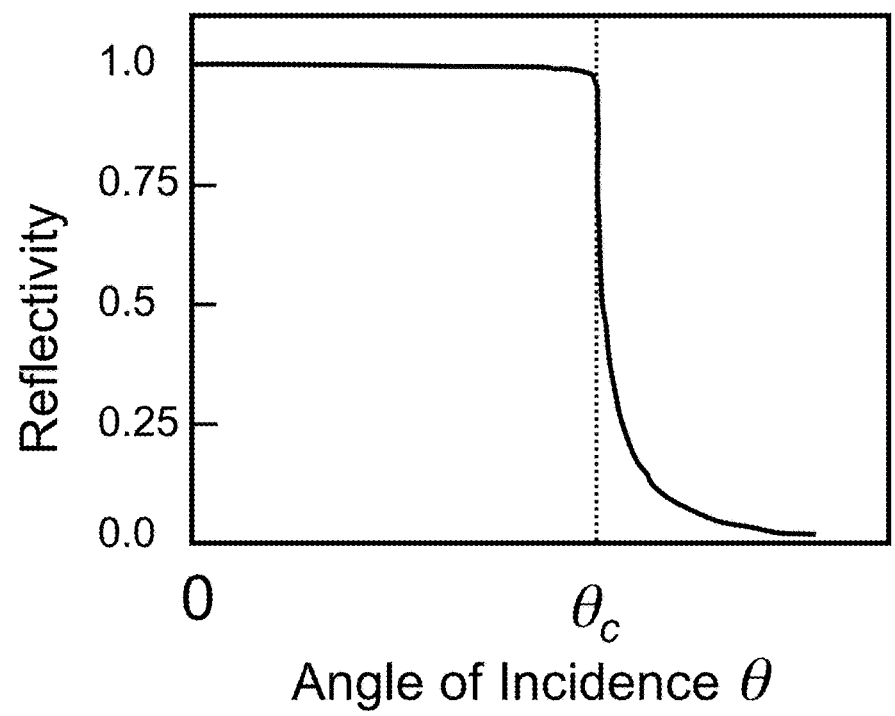
FIG. 6 illustrates a plot of the reflectivity of an x-ray material at angles near the critical angle.

By placing an object 240 to be examined where it will be illuminated by the reflected x-rays 887, x-ray fluorescence 2888 is generated. A suitable detector 290 (not shown in FIG. 16A) may be placed to collect the emitted fluorescence. As illustrated, a detector with an annular geometry is shown, which may collect fluorescence over a larger solid angle than the prior art configuration illustrated in FIGS. 2 and 4.

Note that these figures are not drawn to scale, but drawn to illustrate the principle more clearly—such detectors often have much larger dimensions than the x-ray optics, but such a scale drawing would have obscured the source and optical elements in this three-dimensional illustration.

3.1. Ellipsoidal Optics.

Figure 17:
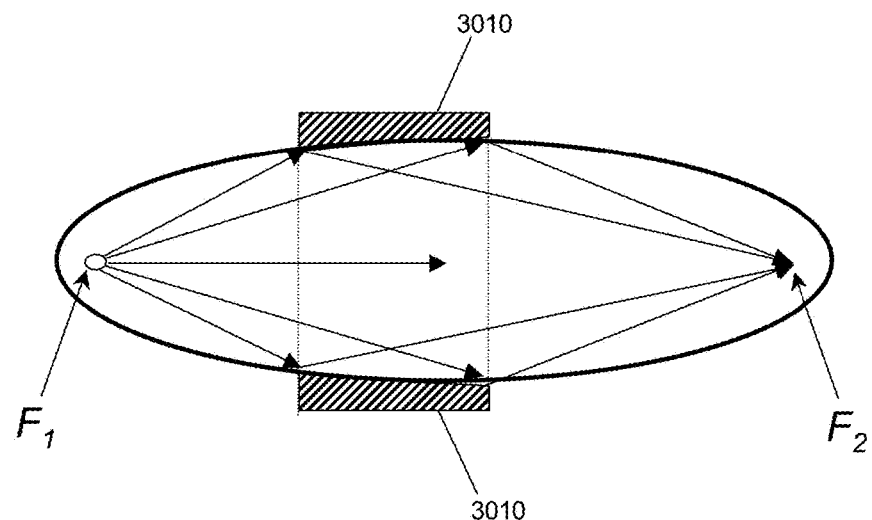
FIG. 17 illustrates a cross section of ellipsoidal optics.

FIG. 17 illustrates one possible optical configuration for the optical element using the form of an ellipse. An ellipse has two foci $F_1$ and $F_2$ such that any photons radiating from one of the foci will be reflected and converge onto the other. By configuring the inner surface of a tube-shaped optical element 3010 to have an elliptical surface, and choosing the coating for the reflecting portion of the tube such that the angle of incidence for the x-rays is smaller than the critical angle, total external reflection is achieved. Then, at least a portion of the x-rays generated by a source placed at one of the foci will be focused to the other focus.

Figure 18:
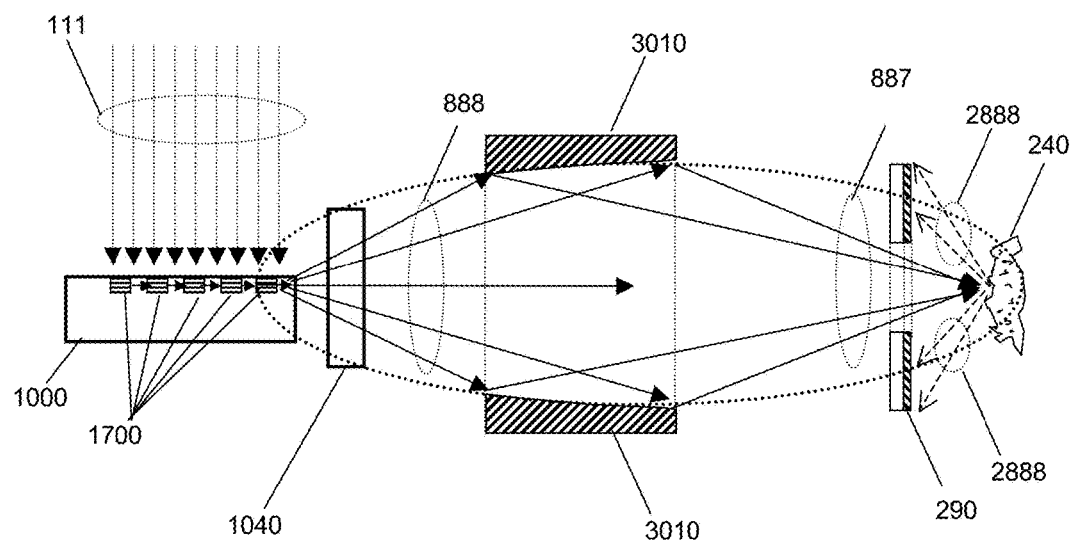
FIG. 18 illustrates a cross section schematic view of an embodiment of the invention using an ellipsoidal optical element.

FIG. 18 illustrates a portion of an embodiment of the invention utilizing an elliptical reflector 3010. An x-ray source comprising x-ray generating microstructures 1700 embedded in a substrate 1000 generate x-rays 888 by linear accumulation when bombarded by electrons 111 in a vacuum. They pass through a window 1040 as a diverging source of x-rays. A portion of the x-rays experience total external reflection from the inner elliptical surface of a tube-like optical element 3010, and become focused x-rays 887 that converge onto the object 240 to be examined. The object 240 emits x-ray fluorescence 2888 when exposed to the focused x-rays, which are in part detected by a detector 290. As illustrated, the detector is in the shape of an annulus, allowing the x-ray excitation to travel through the hole in the center and impinge upon the object, and x-ray fluorescence 2888 is detected using the outer annular ring.

Figure 19:
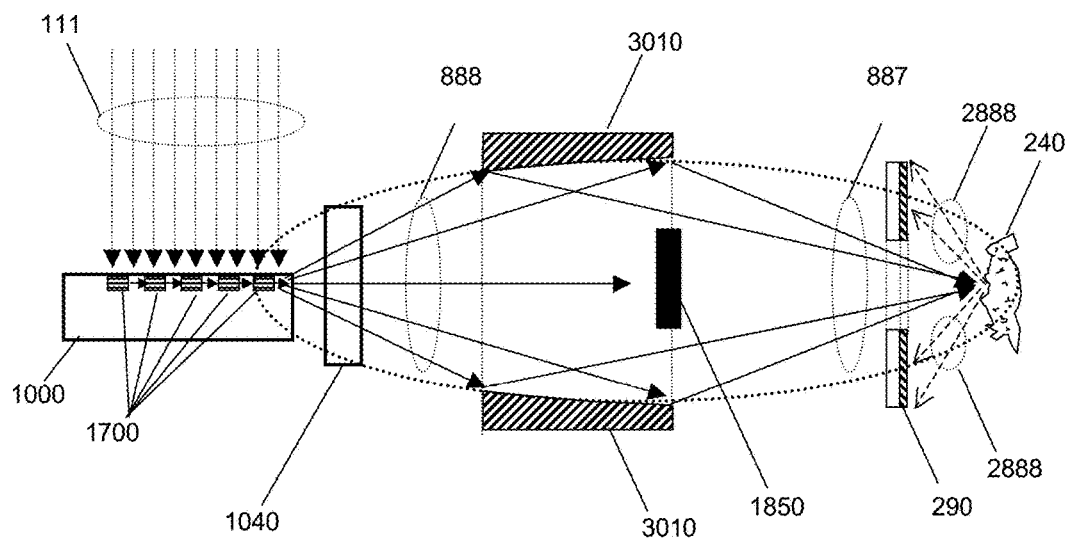
FIG. 19 illustrates a cross section schematic view of an embodiment of the invention using an ellipsoidal optical element.
Figure 20:
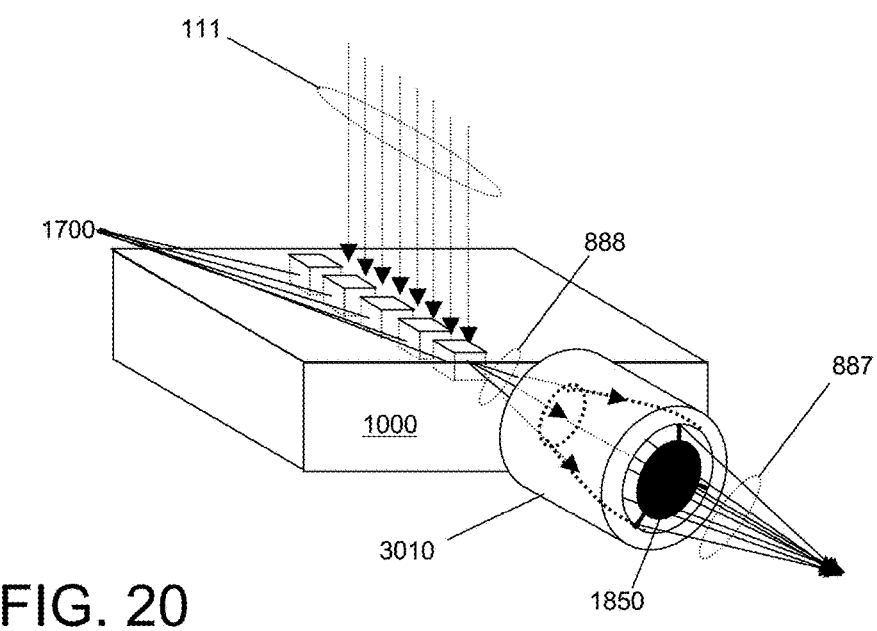
FIG. 20 illustrates a conceptual perspective view of the embodiment of the invention shown in FIG. 18.

In some embodiments, as illustrated in FIG. 19 and the corresponding perspective view of FIG. 20, the on-axis x-rays may be blocked with a beam stop 1850.

3.2. Paraboloidal Optics.

Figure 21:
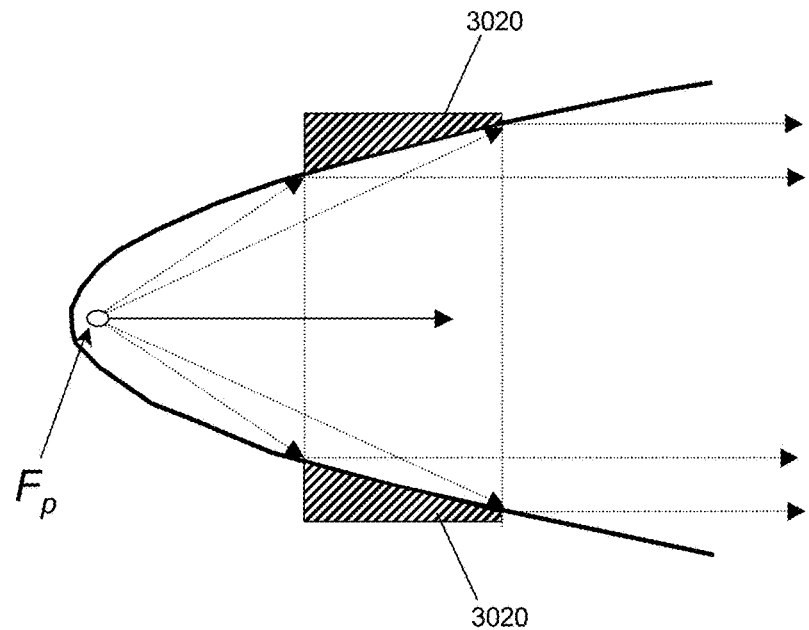
FIG. 21 illustrates a cross section of paraboloid optics.

FIG. 21 illustrates another possible optical configuration using the form of a parabola. A parabola has single focus foci $F_p$ such that any photons radiated from the focus will be reflected emerge as a parallel (collimated) beam. By configuring the inner surface of a tube-shaped optical element 3020 to have a paraboloid surface, and choosing the coating for the reflecting portion of the tube such that the angle of incidence for the x-rays is smaller than the critical angle, total external reflection is achieved. Then, at least a portion of the x-rays generated by a source placed at the focus will emerge as a collimated beam of x-rays.

Figure 22:
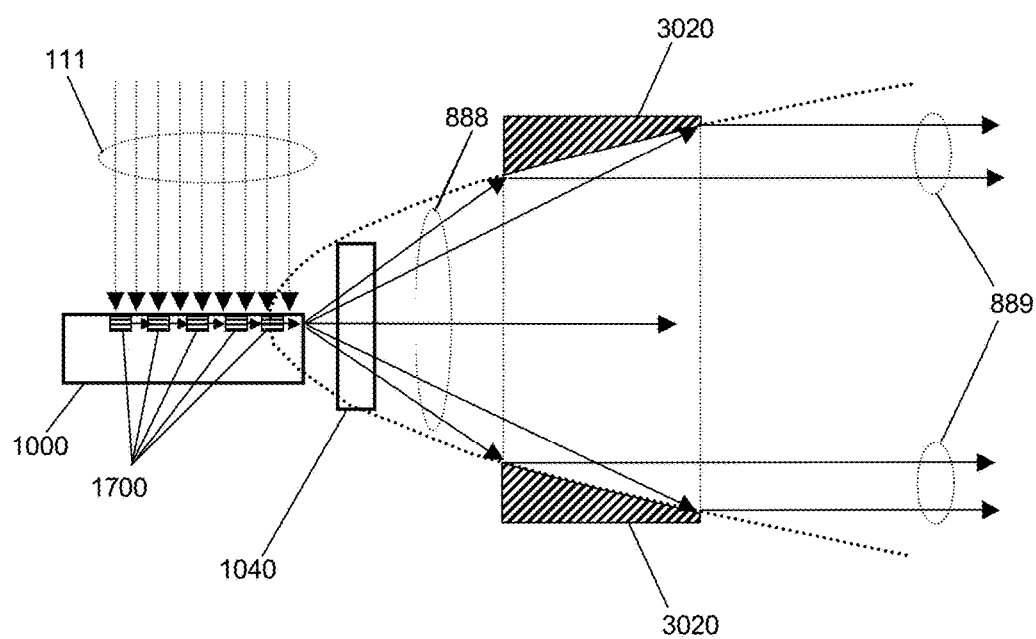
FIG. 22 illustrates a cross section schematic view of an embodiment of the invention using a paraboloid optical element.

FIG. 22 illustrates a portion of an embodiment of the invention utilizing a paraboloidal reflector 3020. An x-ray source comprising x-ray generating microstructures 1700 embedded in a substrate 1000 generate x-rays 888 by linear accumulation when bombarded by electrons 111 in a vacuum. They pass through a window 1040 as a diverging source of x-rays. A portion of the x-rays experience total external reflection from the inner paraboloidal surface of a tube-like optical element 3020, and become collimated x-rays 889.

Figure 23:
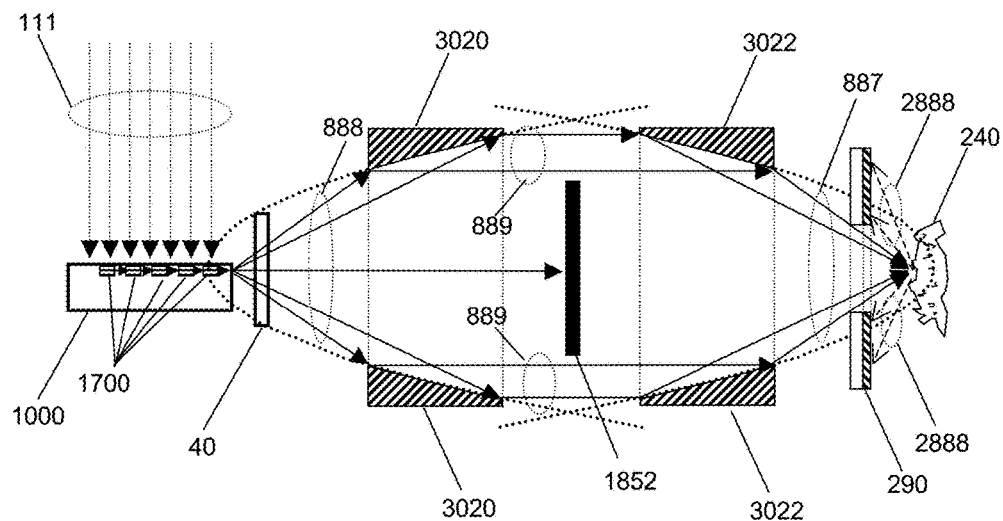
FIG. 23 illustrates a cross section schematic view of an embodiment of the invention using a paraboloid optical element.
Figure 24:
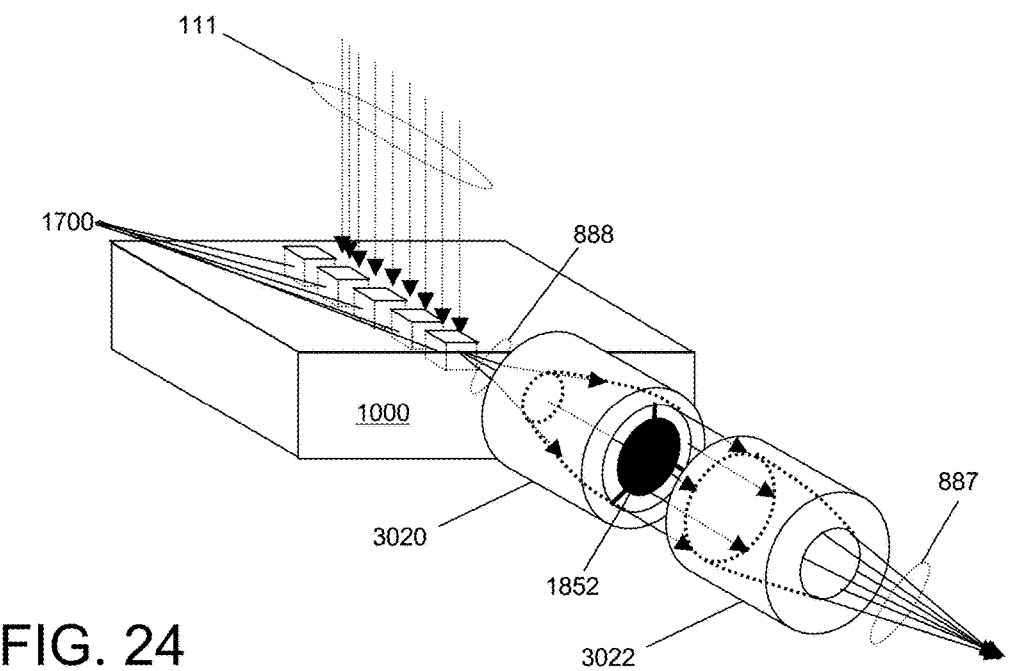
FIG. 24 illustrates a conceptual perspective view of the embodiment of the invention shown in FIG. 22.

Once collimated, a second optical element 3022 with a tube-shaped topology and paraboloidal inner surface, as shown in FIGS. 23 and 24 may be aligned with the optical axis of the first optical element 3020 so that the collimated x-rays 889 are incident on the inner surface of the second optical element 3022 at angles smaller than the critical angle for the surface. The reflected x-rays form a bundle of converging x-rays 887. Placing an object 240 to be examined at this focus allows x-ray fluorescence 2888 to be generated, which is then collected on a detector 290.

Although the illustration shows a second paraboloidal optical element 3022 of the same size and shape as the initial paraboloidal optical element 3020, these need not be the same dimensions, but may have paraboloid surfaces with different curvature and relative focus positions.

In some embodiments, as illustrated in FIG. 23 and the corresponding perspective view of FIG. 24, the on-axis x-rays may be blocked with a beam stop 1852.

Using structured targets for x-ray generation allows the use of multiple materials for x-ray generation, and the characteristic lines of several different materials may be generated by the source in some embodiments of the invention. These multi-material targets have been discussed in more detail in the co-pending Patent Applications mentioned above.

Figure 25:
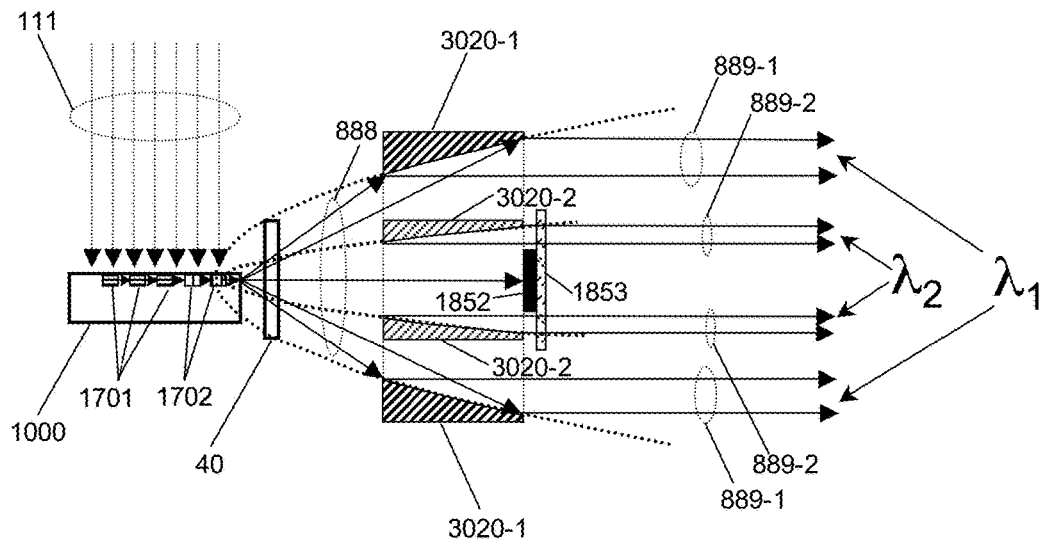
FIG. 25 illustrates a cross section schematic view of a portion of a dual wavelength embodiment of the invention using a set of nested paraboloid optical elements.
Figure 26:
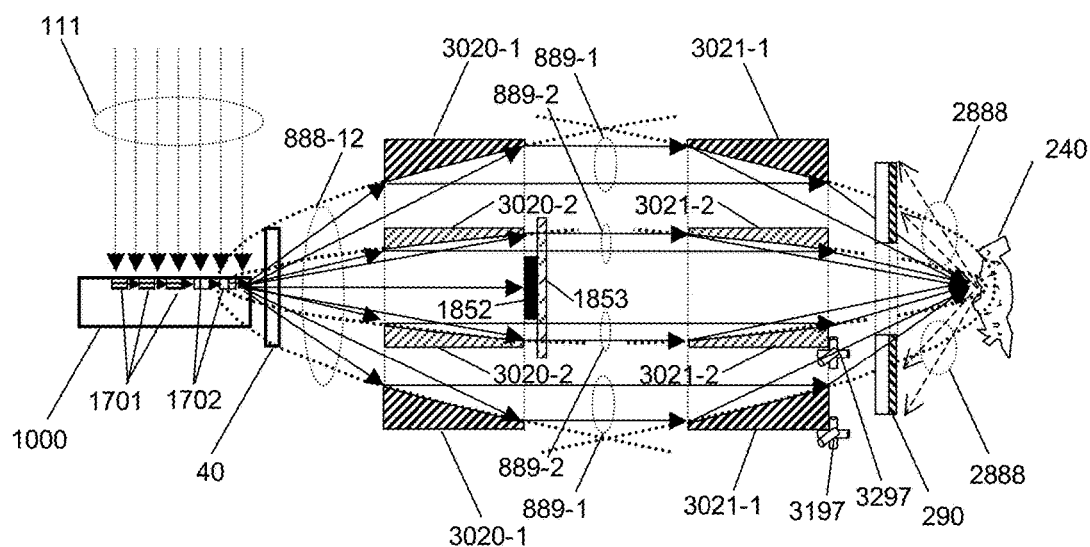
FIG. 26 illustrates a cross section schematic view of a dual wavelength embodiment of the invention using sets of nested paraboloid optical elements.

FIGS. 25 and 26 illustrate the use of such a target in which two types of microstructures 1701 and 1702 have been embedded in the substrate 1000, and, when bombarded by electrons, will generate two wavelengths (or spectral bands) of x-rays. For example, if the first set of microstructures 1701 comprise copper (Cu, Z=28, $K_{\alpha 1}$=8.048 keV) and the second set 1702 comprise rhodium (Rh, Z=45, $K_{\alpha 1}$=20.216 keV), both higher energy and lower energy x-rays will be generated by the target.

As illustrated in FIG. 25, two sets of co-axial optical elements can be aligned to provide two collimated beams of x-rays, each having different energies. As illustrated, the outer set of optics is a set of paraboloidal collimating optics 3020-1 designed collect x-rays at a larger angle, and will therefore provide total external reflection only for the lower energy x-rays (e.g. the Cu x-rays at 8.048 keV), producing a collimated beam of the lower energy x-rays 889-1. The inner set of optics is also a set of paraboloidal collimating optics 3020-2 designed collect x-rays at a smaller angle, and will therefore provide total external reflection for both the low and high energy x-rays.

As in the previously described embodiments, a beam stop 1852 may be used to block the on-axis un-collimated x-rays. As shown in FIGS. 25 and 26, however, this may be combined with a filter that 1853 that blocks the lower energy x-rays for the inner set of optics, allowing only the collimated beam of higher energy x-rays 889-2 reflected from the second set of optics 3020-2 to be transmitted. This segregated spectral purity may be appropriate for many uses, depending on the downstream focusing optics that are used and the relative brightness of the different x-ray wavelengths generated.

As illustrated in FIG. 26, once collimated, a second set of dual-wavelength optics 3021-1 and 3021-2 may also be provided in some embodiments of the invention to focus the two collimated x-ray wavelengths onto a object 240 for XRF analysis. Because two wavelengths are present with two sets of focusing optics, a means for making translation and rotation adjustment 3197 and 3297 for the sets of optical elements (such as adjustable mounts) may be provided in some embodiments to allow the focused spots of the two imaging optical elements to made to overlap on the object 240. In some embodiments, an additional scanning system for the optics, the object 240, or both may be provided to allow systematic study of various positions on the object 240.

It should also be noted that this dual-wavelength optical system may be used even if the target comprises microstructures of a single x-ray generating material. Rhodium (Rh, Z=45) has two characteristic lines ($L_{\beta 1}$=2.835 keV and $K_{\alpha 1}$=20.216 keV) that may be used to excite fluorescence from different elements. Bombarding rhodium targets with electrons having energy great enough to generate x-rays at both these lines would produce a polychromatic x-ray spectrum, and a dual wavelength optical system such as that illustrated in FIGS. 25 and 26 may be used.

It should also be noted that assembly of embodiments with such dual wavelength optical systems may entail mounting the optical elements in mounts that allow the fine adjustment of position and rotation, so that the sets of optical elements for the different wavelengths can be made to be coaxial with each other and also with the x-rays generated, especially if an x-ray target is used that features one-dimensional linear accumulation of x-rays.

3.3. Wolter Optics.

Figure 27:
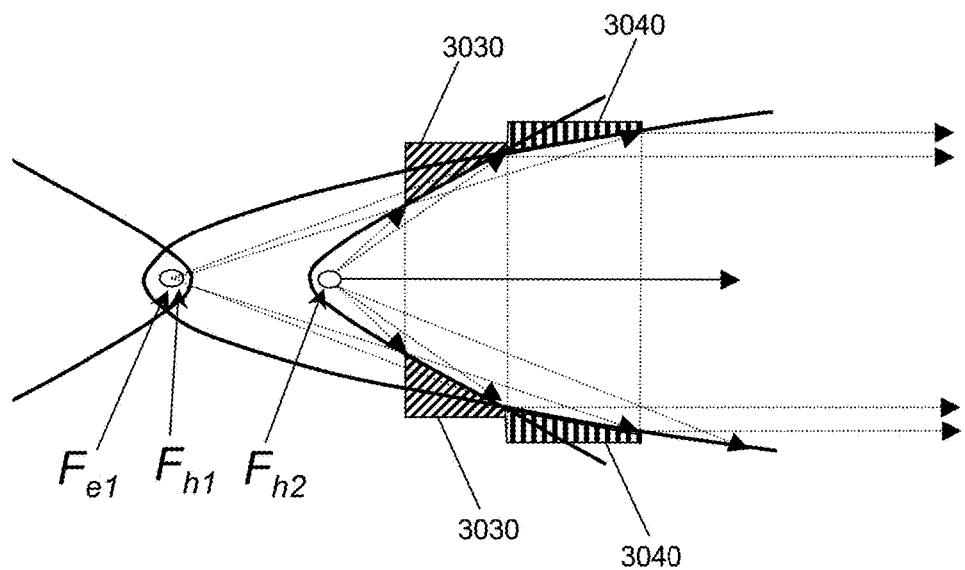
FIG. 27 illustrates a cross section of Wolter Type I optics.

FIG. 27 illustrates another possible optical configuration using the form of an ellipse combined with a hyperbola. The two geometric forms are aligned so one of the foci of the ellipse $F_{e1}$ corresponds to one of the foci of the hyperbola $F_{h1}$. X-rays generated at the other focus of the hyperbola $F_{h2}$ will reflect off a first optical element 3030 corresponding to a hyperbola; the x-ray beam path for the initially reflected x-rays will then reflect from a second optical element 3040 corresponding to the surface of the ellipse, collimating the beam. This also produces a collimated beam. Such optics can often be designed to have a shorter distance between the source and the optical elements, potentially collecting more of the generated x-rays.

By configuring the inner surfaces of two tube-shaped optical elements 3030 and 3040 to have a hyperboloidal and ellipsoidal surfaces, and designing the optical system so that the angle of incidence for the x-rays is smaller than the critical angle (critical angles may be made larger through use of a coating for the reflecting portions; see Table I), total external reflection is achieved. Then, at least a portion of the x-rays generated by a source placed at the focus $F_{h1}$. will emerge as a collimated beam of x-rays. A two-component x-ray optical system of this kind is known as Wolter Type I optics [see H. Wolter, Spiegelsysteme streifenden Einfalls als abbildende Optiken für Röntgenstrahlen, Annalen der Physik vol. 10 (1952), pp. 94-114].

Figure 28:
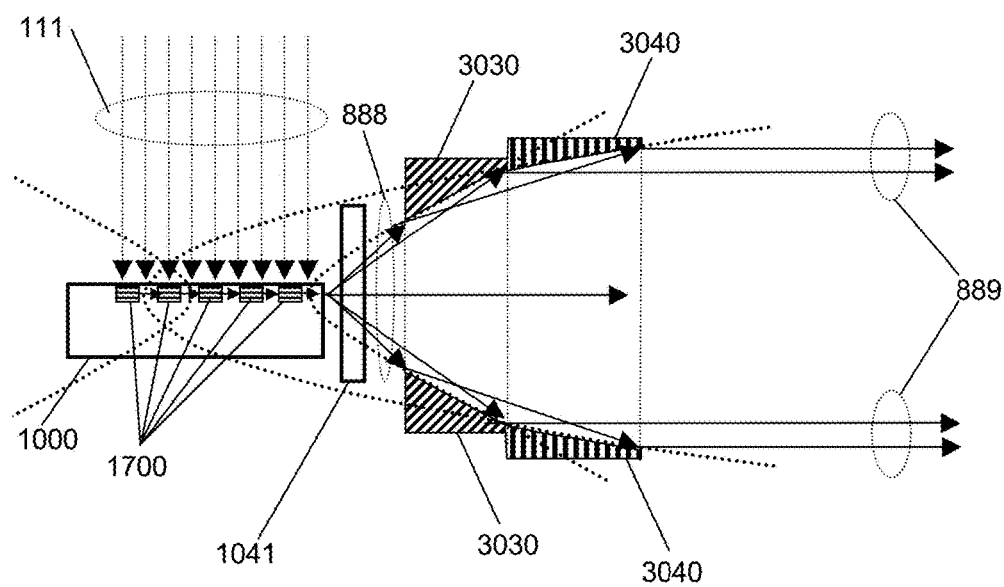
FIG. 28 illustrates a cross section schematic view of an embodiment of the invention using Wolter Type I optics.

FIG. 28 illustrates a portion of an embodiment of the invention utilizing a Wolter Type I optical design. An x-ray source comprising x-ray generating microstructures 1700 embedded in a substrate 1000 generate x-rays 888 by linear accumulation when bombarded by electrons 111 in a vacuum. They pass through a window 1041 as a diverging source of x-rays. A portion of the x-rays experience total external reflection from the inner hyperboloidal surface of a tube-like optical element 3030, and subsequently experience total external reflection from the inner elliptical surface of a tube-like optical element 3040, and become collimated x-rays 889.

Figure 29:
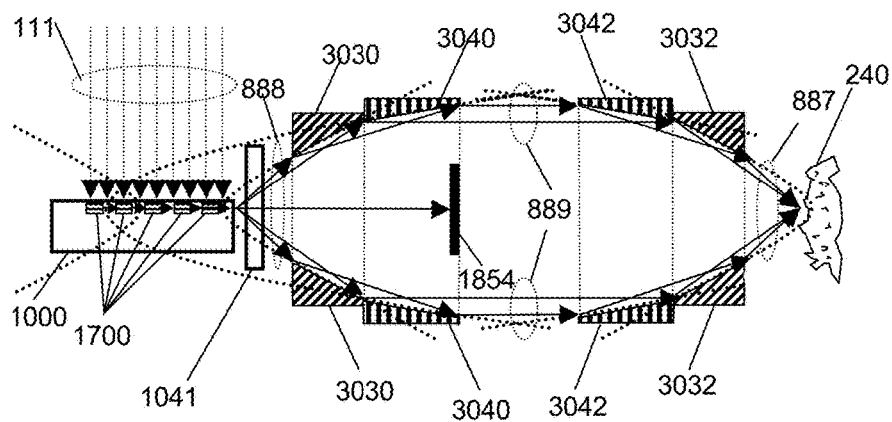
FIG. 29 illustrates a cross section schematic view of an embodiment of the invention using Wolter Type I optics.
Figure 30:
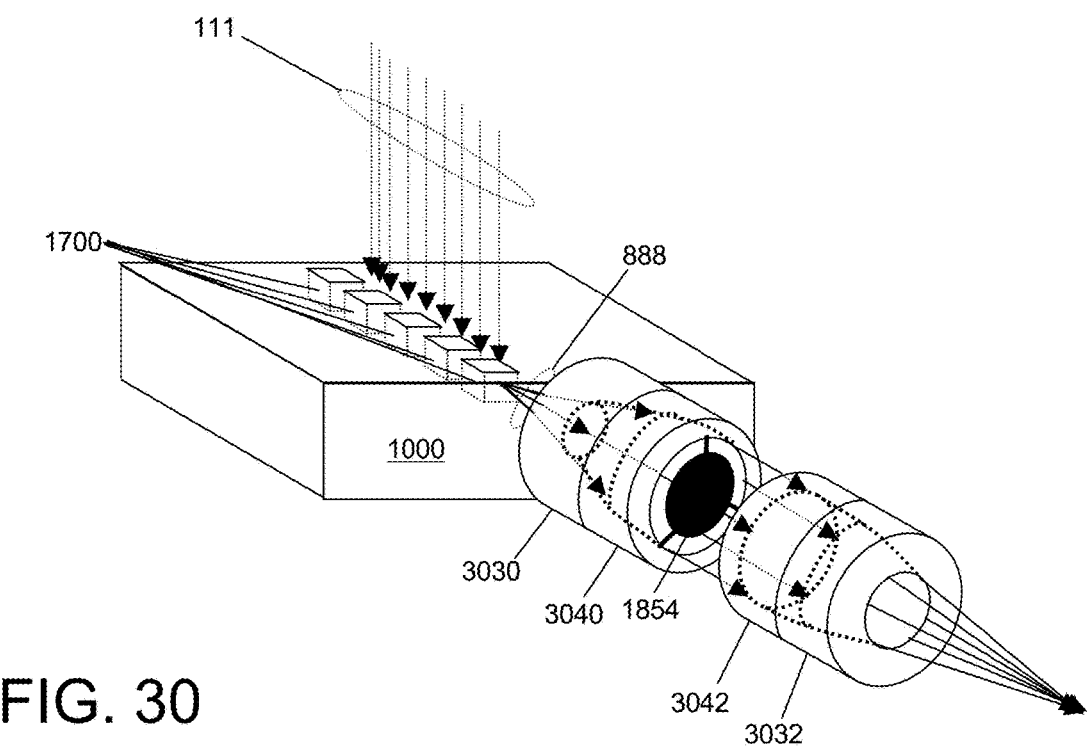
FIG. 30 illustrates a conceptual perspective view of the embodiment of the invention shown in FIG. 29.

Once collimated, a second set of optical elements 3042 and 3032 with a tube-shaped topology and hyperboloidal and ellipsoidal inner surfaces, as shown in FIGS. 29 and 30, may be aligned with the optical axis of the first optical elements 3030 and 3040 so that the collimated x-rays 889 are incident on the inner surface of the second set of optical elements 3042 and 3032 at angles smaller than the critical angle for the surface. The reflected x-rays form a set of converging x-rays 887. Placing an object 240 to be examined at this focus allows x-ray fluorescence (not shown) to be generated, which is then collected on a detector (not shown).

Although the illustrations of FIGS. 29 and 30 show a second set of Wolter Type I optical elements 3042 and 3032 of the same size and shape as the initial set of Wolter optical elements 3030 and 3040 but in a reversed orientation, being used to focus the x-rays, these need not be the same dimensions or even the same type of optics. For example, an optic with a paraboloidal inner surface as was illustrated in FIG. 23 may be provided to focus the collimated x-rays 889, providing a larger working distance to the object 240. Other designs and combinations for x-ray optical elements will be known and may be applied to various embodiments by those skilled in the art.

In some embodiments, as illustrated in FIG. 29 and the corresponding perspective view of FIG. 30, the on-axis x-rays may be blocked with a beam stop 1854.

It should be noted that, although the variation of Wolter optics as shown in FIGS. 27-31 show the second ellipsoidal optical element being used to collimate the x-rays, Wolter designs also exist in which the second ellipsoidal optical element focuses the x-rays, and may be used in some embodiments of the invention. Other configurations of Wolter optical elements may be known to those skilled in the art.

Figure 31:
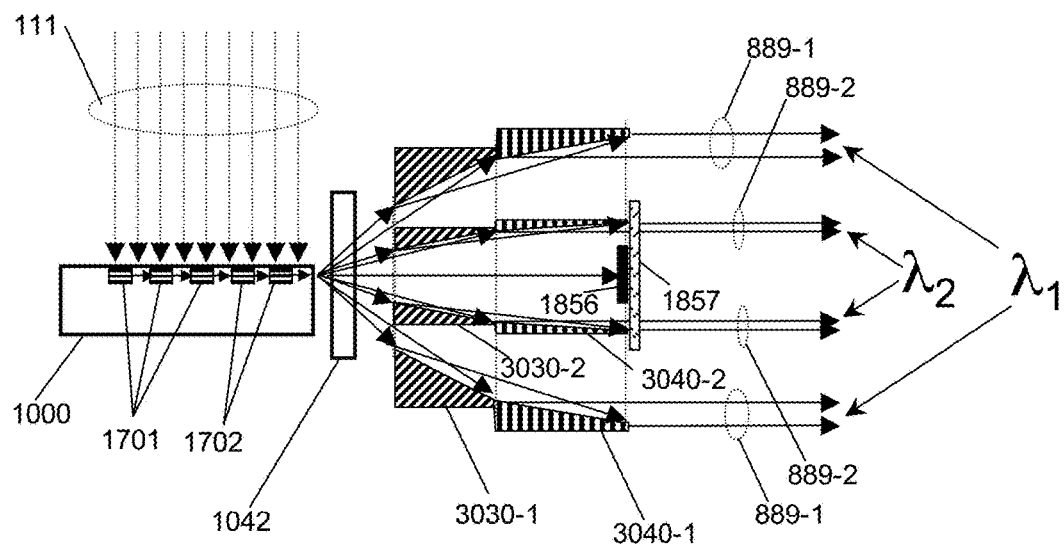
FIG. 31 illustrates a cross section schematic view of a portion of a dual wavelength embodiment of the invention using a set of Wolter Type I optics.

It should also be noted that a dual wavelength source as was illustrated in FIGS. 25 and 26 may also be used with Wolter Type I optical elements, as illustrated in FIG. 31. Again, two types of microstructures 1701 and 1702 are present, and, when bombarded by electrons, will generate two wavelengths (or spectral bands) of x-rays. These will be collected by two sets of nested Wolter Type I optical elements, with one set 3030-1 and 3040-1 being hyperboloidal and ellipsoidal reflectors to collimate the low energy x-rays, and the other set 3030-2 and 3040-2 being hyperboloidal and ellipsoidal reflectors having a smaller diameter to collimate both the high energy and low energy x-rays. As in the dual wavelength paraboloidal embodiment, a beam stop 1856 and a filter 1857 to provide spectral purity for the inner set of optics 3030-2 and 3040-2 may also be provided in some embodiments of the invention.

As in the paraboloidal system previously illustrated in FIG. 26, a second set of Wolter Type I optics may be provided in a "mirror image" of the collimating set as shown in FIG. 31 to focus the collimated beams to a small spot. As in the previously described dual-wavelength paraboloidal system, such an embodiment will typically comprise a means for making translation and rotation adjustment and for the sets of optical elements (such as adjustable mounts) to allow the focused spots of the two imaging optical elements to made to overlap on the object under examination. In some embodiments, an additional scanning system for the optics, the object under examination, or both may be provided to allow systematic study of various positions on the object under examination.

3.4. Polycapillary Optics.

Figure 32:
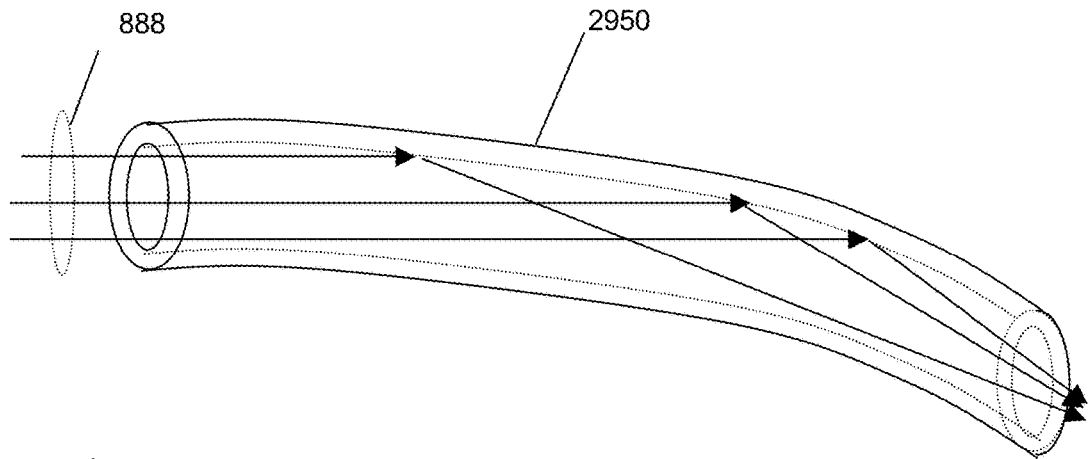
FIG. 32 illustrates a prior art capillary optical element.

Another prior art x-ray optical element is illustrated in FIG. 32. In this illustration, some of the x-rays that enter a hollow tube 2950 experience total external reflection from the inner wall of the tube. If the tube 2950 is curved, the x-rays experiencing multiple internal reflections may be directed to a different exit position, essentially guiding the x-rays. These optical elements are often long and thin, with lateral dimensions on the order of millimeters and several centimeters in length, and are constructed of glass filled with air. These structures may be viewed as similar to light guides made of fiber optics for visible and near-visible light, except that the light guides are solid, utilizing total internal reflection between a core and cladding, and not external reflection from air and a glass wall. [See M. A. Kumakhov and V. A. Sharov, "Multiple reflection from surface X-ray optics", Physics Reports vol. 191(5), (1990) pp 289-350, and H. Chen et al., "Guiding and focusing neutron beams using capillary optics", Nature 357, (4 Jun. 1992), pp. 391-393.]

A larger scale optical element may be fabricated by combining many of these capillary tubes into a bundle that collects x-rays and then redirects them to a point, effectively focusing the x-rays. Such bundled capillary tubes may comprise hundreds or even thousands of glass tubes, and are called polycapillary optics. Polycapillary optics may be used as optical elements in various embodiments of the invention.

Figure 33:
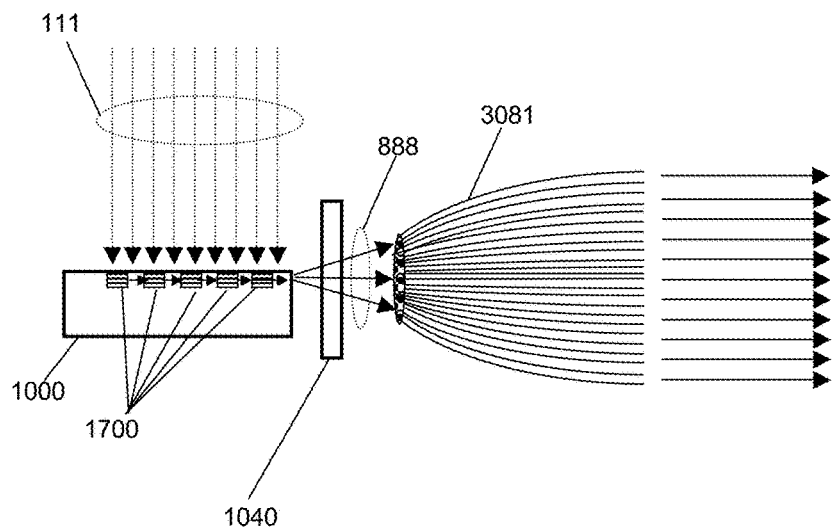
FIG. 33 illustrates a cross section schematic view of an embodiment of the invention using polycapillary optics to collimate x-rays.

FIG. 33 represents a portion of an embodiment of the invention in which a bundle of polycapillary elements have been arranged into a combined optical element 3081 that collects the x-rays 888 and has the exit apertures arranged such that the source is a quasi-collimated source. This may be combined with other optical elements that take the collimated x-rays, such as a paraboloidal reflector, and later focus them into a smaller spot.

Figure 34:
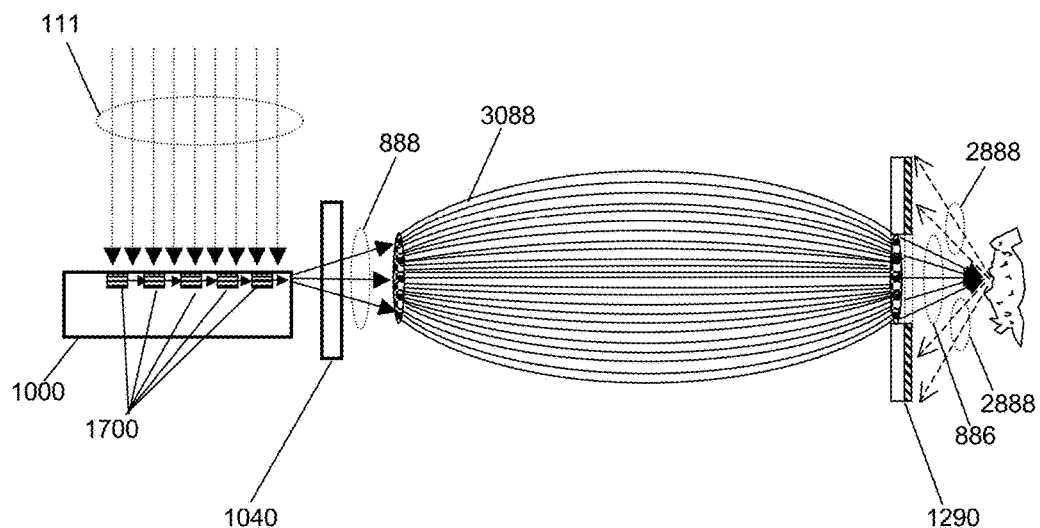
FIG. 34 illustrates a cross section schematic view of an embodiment of the invention using polycapillary optics to focus x-rays.

FIG. 34 illustrates a portion of an embodiment of the invention in which a bundle of polycapillary elements have been arranged into a combined optical element 3088 that collects the x-rays 888 generated from microstructures 1700 embedded in a substrate 1000, and has the exit apertures arranged such that the x-rays converge in a quasi-focused pattern. The converging x-rays 886 from configuration may be used to illuminate a object 240 for examination, which emits x-ray fluorescence 288 when illuminated. These fluorescent x-rays are then detected by a detector 290.

3.5. Other X-Ray Optics.

Figure 35A:
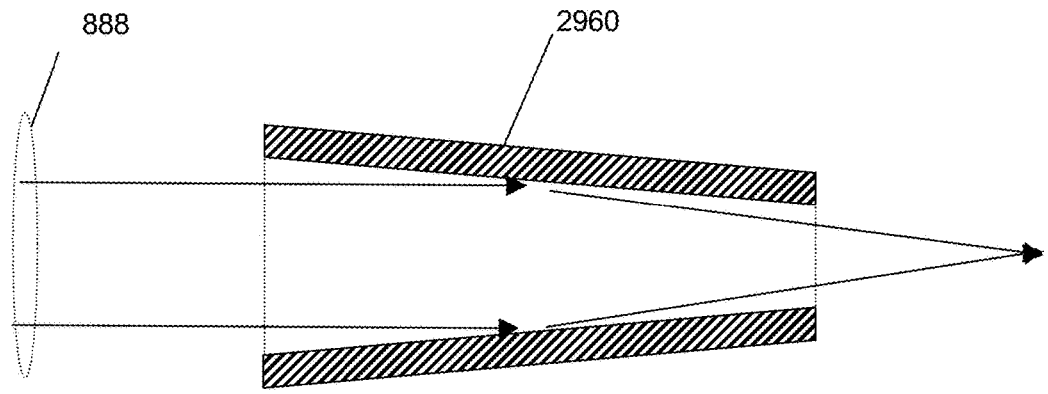
FIG. 35A illustrates a cross section of a prior art tapered cone x-ray optical element.
Figure 35B:
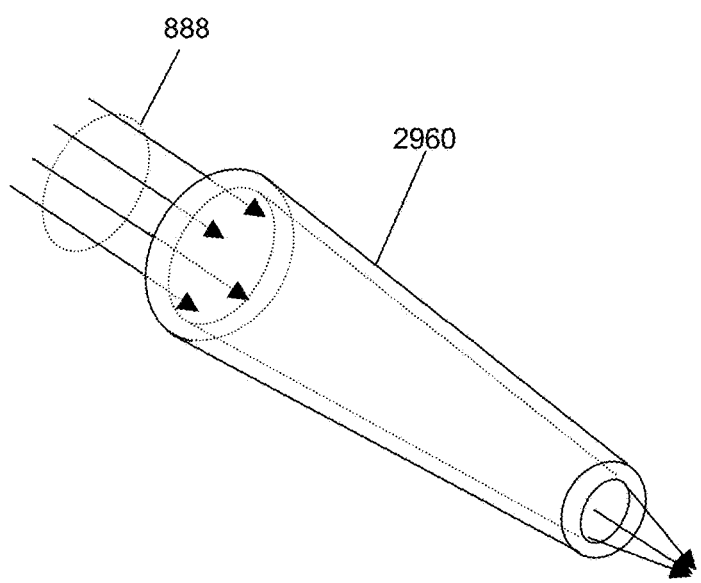
FIG. 35B illustrates a perspective view of the prior art tapered cone x-ray optical element of FIG. 35A.

Another prior art x-ray optical element is illustrated in FIG. 35A and FIG. 35B. In these illustrations, some of the x-rays that enter a tapered hollow tube 2960 experience total external reflection from the inner wall of the tube. If the tube 2960 is a cone-shape, the x-rays experiencing some concentration of x-rays at the output may occur. Such an x-ray guide tube has been described by Yoshio Suzuki et al., in "Hard X-ray Imaging Microscopy using X-ray Guide Tube as Beam Condenser for Field Illumination", Journal of Physics: Conference Series vol. 463 (2013): 012028.

Figure 36:
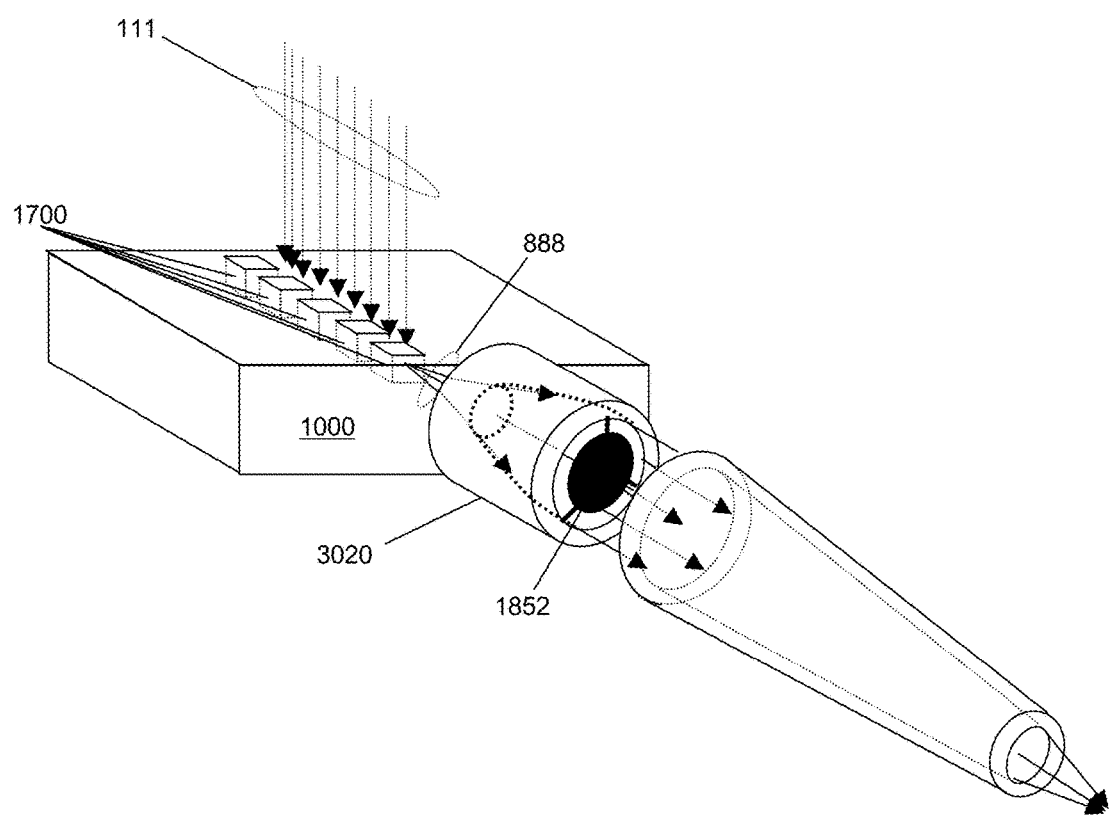
FIG. 36 illustrates a perspective view of an embodiment of the invention incorporating a tapered cone x-ray optical element.

As with the capillary tubes described above, these conical optical elements are often long and thin, with lateral dimensions on the order of millimeters or smaller and length on the order of several centimeters, and are constructed of glass filled with air. They are also typically designed to accept collimated beams as input, with the smaller output aperture of the tube causing convergence of the x-rays. These may therefore be used in embodiments of the invention as illustrated in FIG. 36 in combination with collimating optical elements, such as those described earlier, to provide a concentration of x-rays.

The optical elements described above may be fabricated of any number of optical materials, including glass, silica, quartz, BK7, silicon (Si), Ultra-low expansion glass (ULE™), Zerodur™ or other elemental materials.

The reflective coatings used for the various optical elements used in embodiments of the invention as described above may be a single elemental material, to take advantage of the total external reflection for angles of incidence smaller than the critical angle, and preferably may be coated with a layer of higher mass density material (greater than 2.5 g/cm$^3$) at least 25 nm thick. Or, the reflective coatings may be multilayer coatings, with alternating periodic layers of two or more materials, that provide constructive interference in reflection for certain wavelengths. The reflection efficiency depends on the wavelength and angle of incidence of the x-rays, and the thickness of the alternating layers, so this has limited use as a broad band reflector, but may be used if specific wavelengths are desired. Combinations that may be used for multilayer reflectors may be tungsten/carbon (W/C), tungsten/tungsten silicide (W/WSi$_2$), molybdenum/silicon (Mo/Si), nickel/carbon (Ni/C), chromium/scandium (Cr/Sc), and lanthanum/boron carbide (La/B$_4$C), and tantalum/silicon (Ta/Si), among others. The surface may also be a compound coating comprising an alloy or mixture of several materials.

Figure 37A:
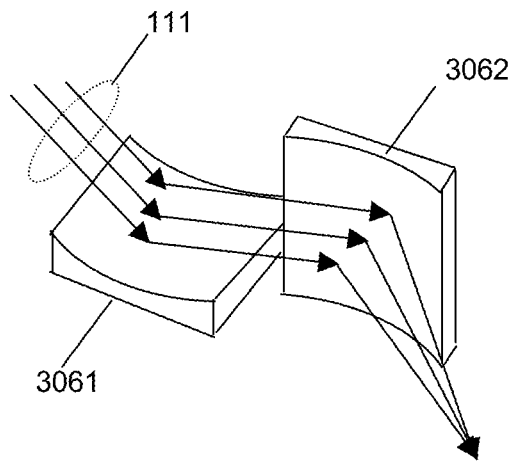
FIG. 37A illustrates a perspective view of prior art Kirkpatrick-Baez optical elements.
Figure 37B:
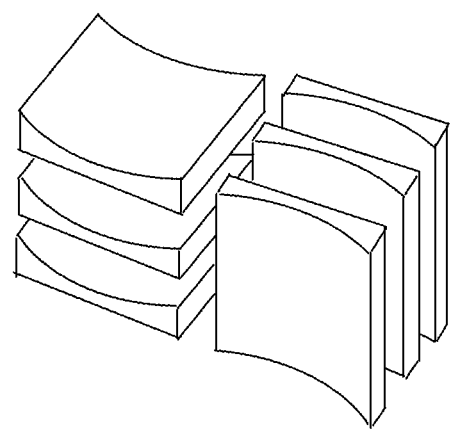
FIG. 37B illustrates a perspective view of multiple prior art Kirkpatrick-Baez optical elements.

Kirkpatrick-Baez optics may also be used in some embodiments of the invention. These are illustrated in FIGS. 37A and 37B. Incident x-rays 111 first reflect off a first cylindrical optical element 3061 oriented to focus the x-rays in one dimension (e.g. the x-axis), and the reflected x-rays then reflect off a second cylindrical optical element 3062 oriented to focus the x-rays in the orthogonal dimension (e.g. the y-axis), with the curvature of each element designed to produce coincident points of focus in x and y.

Embodiments with multiple sets of such optical elements stacked to collect additional x-rays, as illustrated in FIG. 37B, may be designed for some embodiments of the invention.

Other optical elements, such as Fresnel Zone Plates, cylindrical Wolter optics, Wolter Type II optics, Wolter Type III optics, Schwarzschild optics, Montel optics, diffraction gratings, crystal mirrors using Bragg diffraction, hole-array lenses, multi-prism or "alligator" lenses, rolled x-ray prism lenses, "lobster eye" optics, micro channel plate optics, or other x-ray optical elements may be used or combined with those already described to form compound optical systems for embodiments of the invention that direct x-rays in specific ways that will be known to those skilled in the art.

3.6. X-Ray Optics with Monochromators.

For applications in which the spectral purity of the x-rays is important, embodiments of the invention that comprise an optical system that provides spectral purity by the incorporation of a monochromators may be used.

Figure 38:
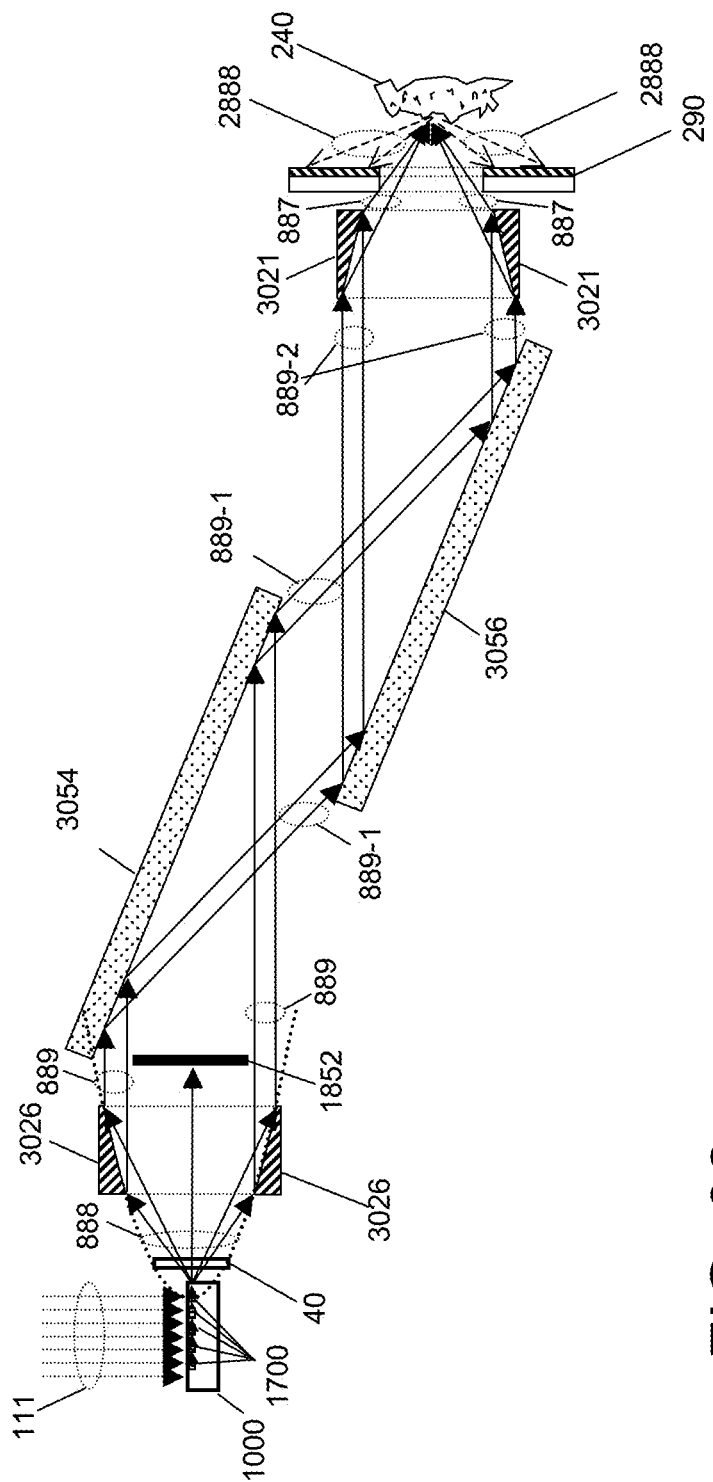
FIG. 38 illustrates a cross section schematic view of an embodiment of the invention comprising a monochromator.

Such a system is illustrated in FIG. 38. In the system as illustrated, the x-rays are generated by a set of microstructures 1700 embedded in a substrate 1000 under bombardment by electrons 111. Although x-rays at monochromatic characteristic lines may be generated, some materials generate x-rays at more than one characteristic line, and furthermore, wide spectrum bremsstrahlung will also be present.

The optical system in the embodiment shown in FIG. 38 begins with a paraboloidal reflector 3026 oriented to collimate the x-rays 888 generated by the microstructures 1700. The collimated x-rays 889 then propagate to a crystal diffraction element 3054 that is designed to reflect a single wavelength at high efficiency. The angle of incidence on the first crystal will depend on the wavelength to be reflected and the crystal lattice spacing, but angles of around 2°-60° are typical.

The once-reflected x-rays 889-1 then propagate to a second crystal diffraction element 3056 that is designed to again reflect efficiently the same wavelength as the first crystal diffraction element 3054. The twice-reflected x-rays with a narrowed spectral bandwidth 889-2 then propagate as a collimated beam towards the object 240. Before reaching the object, however, another paraboloidal optical element 3021 is encountered that takes the collimated x-rays and creates a converging beam of x-rays 887. The x-rays focus to a spot on the object 240 that emits x-ray fluorescence 2888 detected by a detector 290.

The mount for the first crystal diffraction element 3054 may be an adjustable mount that allows translation and rotation, to maximize the reflective efficiency of the crystal, or may be fixed at a predetermined angle relative to the paraboloidal optical element 3026. Likewise, the mount for the second crystal diffraction element 3056 may be an adjustable mount that allows translation and rotation, to maximize the reflective efficiency of the crystal, or may be fixed at a predetermined angle relative to the first crystal 3054 and the paraboloidal optical element 3026. The crystal diffraction Miller index is selected to obtain the energy resolution required. In some embodiments, the x-ray energy bandwidth may be as small as 10 eV. The double crystal monochromator will typically comprise one or more rotary stages with rotation axis that is parallel to the crystal diffraction plane and perpendicular to the x-ray beam propagation direction.

Some typical crystals used for these diffractive monochromators are quartz ($SiO_2$), lithium fluoride (LiF), sapphire ($Al_2O_3$), calcite ($CaCO_3$), topaz ($Al_2(F,OH)_2SiO_4$), aluminum (Al), silicon (Si), germanium (Ge), and indium antimonide (InSb), among others. Crystal reflection efficiencies as large as 90% or higher may be achieved.

As shown, two optical elements are used to provide spectral purity, but embodiments that use only one diffractive element in reflection may also be designed. Likewise, other embodiments employing multiple elements to enhance spectral purity may be designed.

Reflectors that comprise ordered multilayers of materials, such as Mo/Si, as previously described above, can also provide wavelength selective reflection. The configuration used may be similar to that illustrated in FIG. 38, and embodiments using one, two, or even more reflective multilayer elements may be designed. Depending on the material and angle of incidence, multilayer reflectivity as high as 60%-70% may be achieved.

For more on crystal or multilayer reflectors, see James H. Underwood, "Multilayers and Crystals", Section 4.1 of the X-ray Data Booklet, which may be downloaded at: xdb.lbl.gov/Section4/Sec_4-1.pdf.

4. Detectors

Several detectors may be used to detect the fluorescence generated by a object under examination in embodiments of the invention, and many of these prior art detectors are well known to those skilled in the art.

Fluorescence tends to be emitted uniformly, and therefore a larger detector collecting emitted fluorescence x-rays over a larger collection angle will produce a better signal-to-noise ratio. Such a configuration was illustrated in the general illustration of FIG. 16B, in which the detector 290 shown is an annular shape facing the object 240 under examination.

There are three types of x-ray detectors having energy resolution (also known as spectrometers) that may be used to detect the fluorescent x-rays generated by a object under examination.

The first type, known as energy dispersive x-ray spectrometer (EDS), uses a semiconductor device to measure the energy of the detected x-ray photons. When an x-ray is absorbed by the detector, it creates a number of electron-hole pairs, with the number of electrons liberated depending on the energy of the x-ray photon. The electrons are drawn to the anode, and become a pulse of current exiting the detector. The measurement of the transient current from each pulse by a charge sensitive pre-amplifier and pulse processing electronics allows an estimation of the individual x-ray photon energy. "Counts" of electron bursts at different energies allow the quantitative determination of the spectrum of fluorescence x-rays. The silicon PIN photodiode (Si-PIN) is a simple and low cost class of EDS spectrometer that typically has the lowest performance in terms of energy resolution.

The lithium drifted silicon (Si(Li)) or germanium (Ge(Li)) spectrometer is another class of EDS with significant better energy resolution than Si-PIN, but has a count rate limited typically to less 30,000 counts per second and requires deep cooling down to liquid nitrogen temperature. A silicon drift detector (SDD) offers significant higher count rate (>10×) than Si(Li) or Ge(Li) DES and requires modest cooling. Typically, an EDS can simultaneously measure x-ray spectra over a wide energy range, i.e., parallel detection. An EDS is generally preferred for fast measurement of fluorescence x-rays over a wide energy range.

The second type, known as wavelength-dispersive x-ray spectrometer (WDS), uses a wavelength-dispersive component with x-ray wavelength selection property such as a crystal or multilayer optic and an x-ray counter that receives and counts the x-rays selected by the wavelength dispersive component. Typically, a WDS has an energy resolution better than an EDS but requires sequential (serial) measurement of x-ray spectra over a wide wavelength (energy) range. A WDS is generally preferred to measure a single x-ray fluorescence line with high sensitivity and high speed or measure trace elements.

The third type, known as an x-ray microcalorimeter spectrometer (XMS), uses typically a superconductor circuit to measure change of the electric response from absorption of an x-ray photon. An XMS can provide energy resolution comparable to that of WDS and simultaneous measurement over a wide energy range, but its count rate is typically limited, requires cooling of the superconductor down to liquid helium temperature, and has a higher cost than EDS and WDS.

Additional configurations may involve additional filters (e.g. thin foils containing the appropriate element(s)) along the beam path before the detector to preferentially attenuate some unwanted x-rays from arriving at the spectrometer to reduce the background due to the detection of the x-rays scattered from the object or reduce total x-ray flux entering by the spectrometer to avoid saturation. Multiple spectrometers of the same type or combination of two or more types can be used simultaneously or interchangeable to utilize their respective strength individually or collectively. In a Si(Li) or SDD spectrometer, often multiple detector elements are packaged together as a single detector unit to increase the solid angle of collection, to increase the overall count rate, of a combination thereof.

Figure 39:
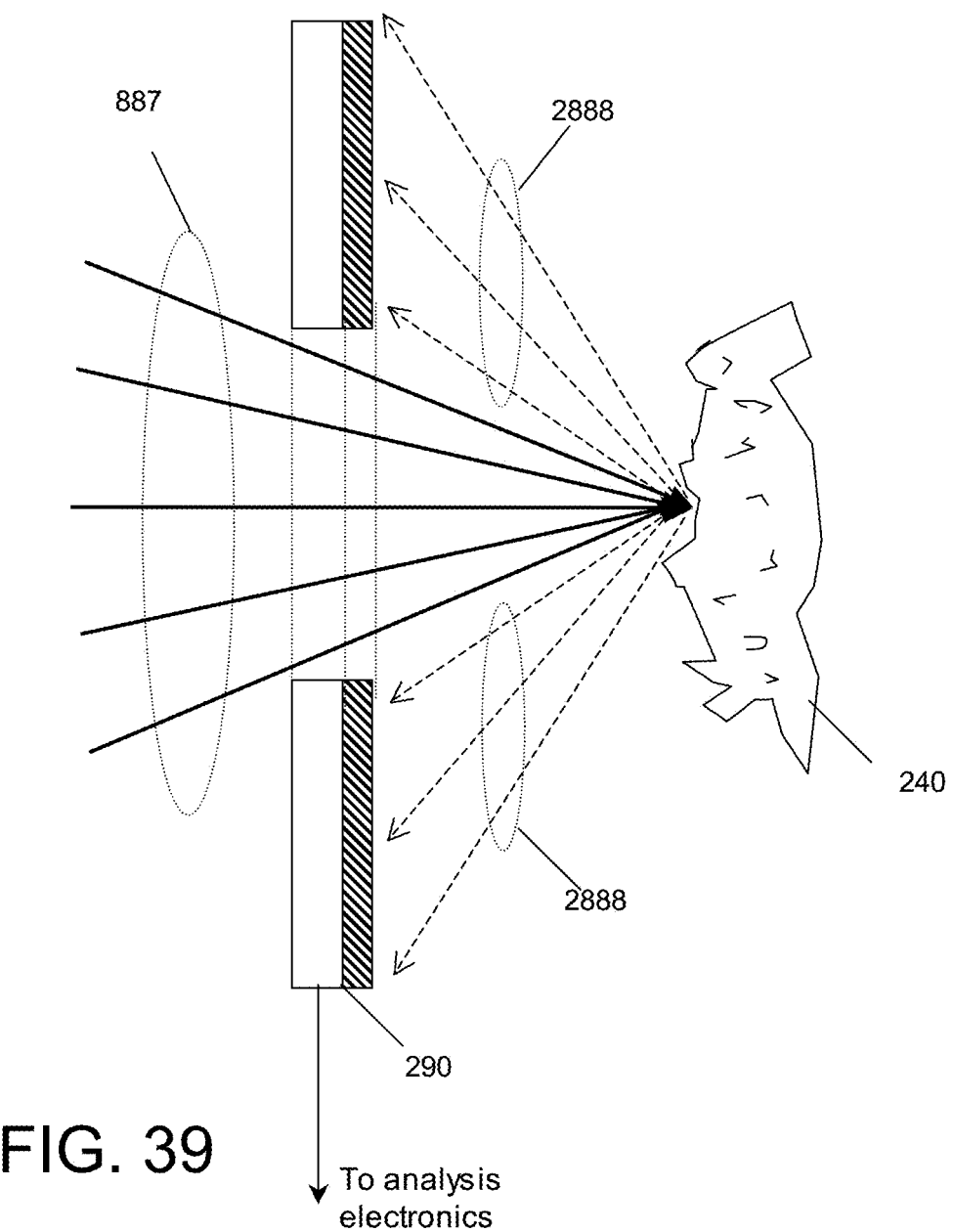
FIG. 39 illustrates a cross section schematic view of the detail of the fluorescence detector according to an embodiment of the invention.

Fluorescent x-rays tend to be emitted isotropically. For some applications, a spectrometer collecting emitted fluorescence x-rays over a larger collection angle will produce a better signal-to-noise ratio is preferred. Such a configuration is illustrated in the general illustration of FIG. 16B, in which the detector 290 shown is an annular shape facing the object 240 under examination. Note that this detector is illustrated as a circular detector with an annulus, but may be of any geometry (rectangular, square, hexagonal, honeycomb) with a through-hole, such as the Rococo 2 (PNDetector GmbH; Munich, Germany). The detection of fluorescent x-rays is illustrated in more detail in FIG. 39, where the converging x-rays 887 are incident onto the object 240 that emits fluorescence 2888, some of which falls on the detector 290.

Figure 40:
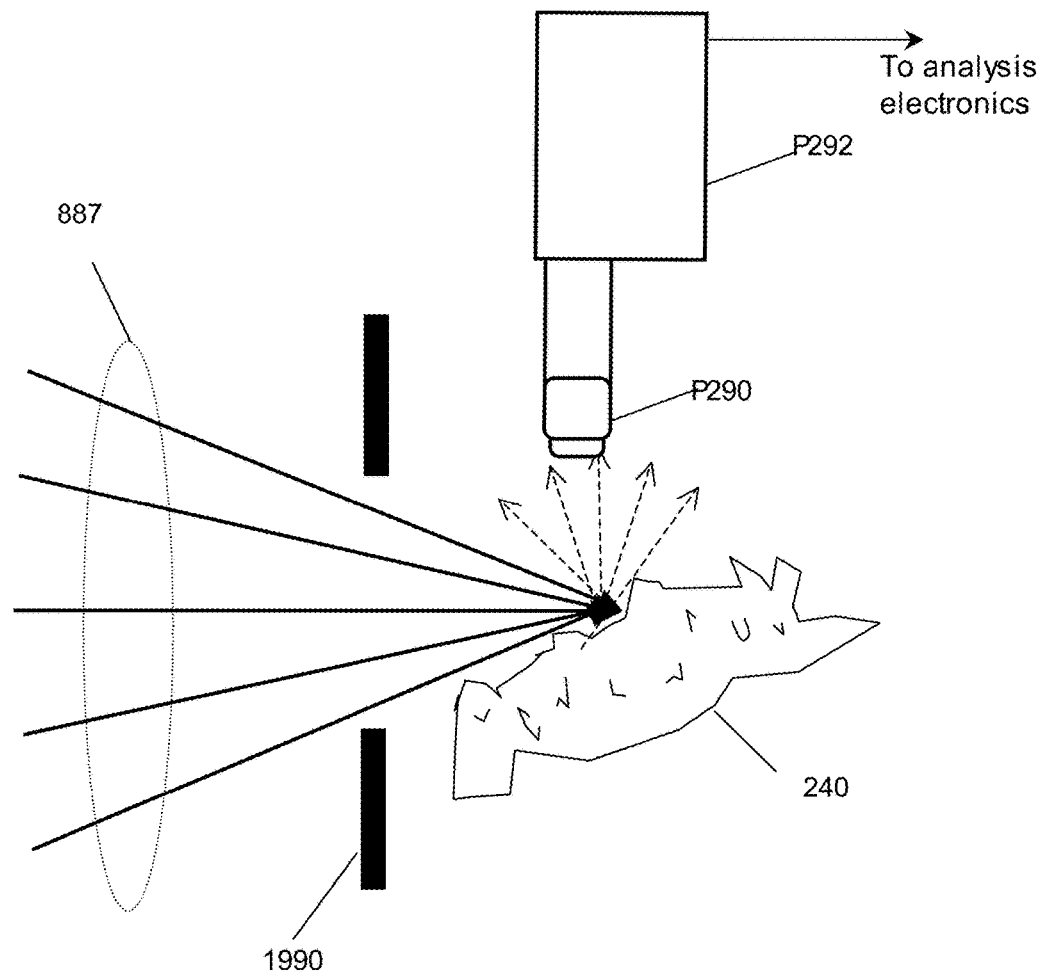
FIG. 40 illustrates a cross section schematic view of an alternative fluorescence detector according to an embodiment of the invention.

If the working distance between the last optical element and the object under examination is too small to conveniently place a detector between them, a more conventional configuration such as that illustrated in FIG. 40 may be used in some embodiments of the invention. Here, instead of passing through an aperture in a detector, the incident x-rays 887 may pass through an aperture in a simple screen 1990 and converge on the object 240 to be examined. A prior art x-ray fluorescence detector P290 with associated electronics P292 may be placed above the object 240 to detect a portion of the emitted fluorescence.

Figure 41:
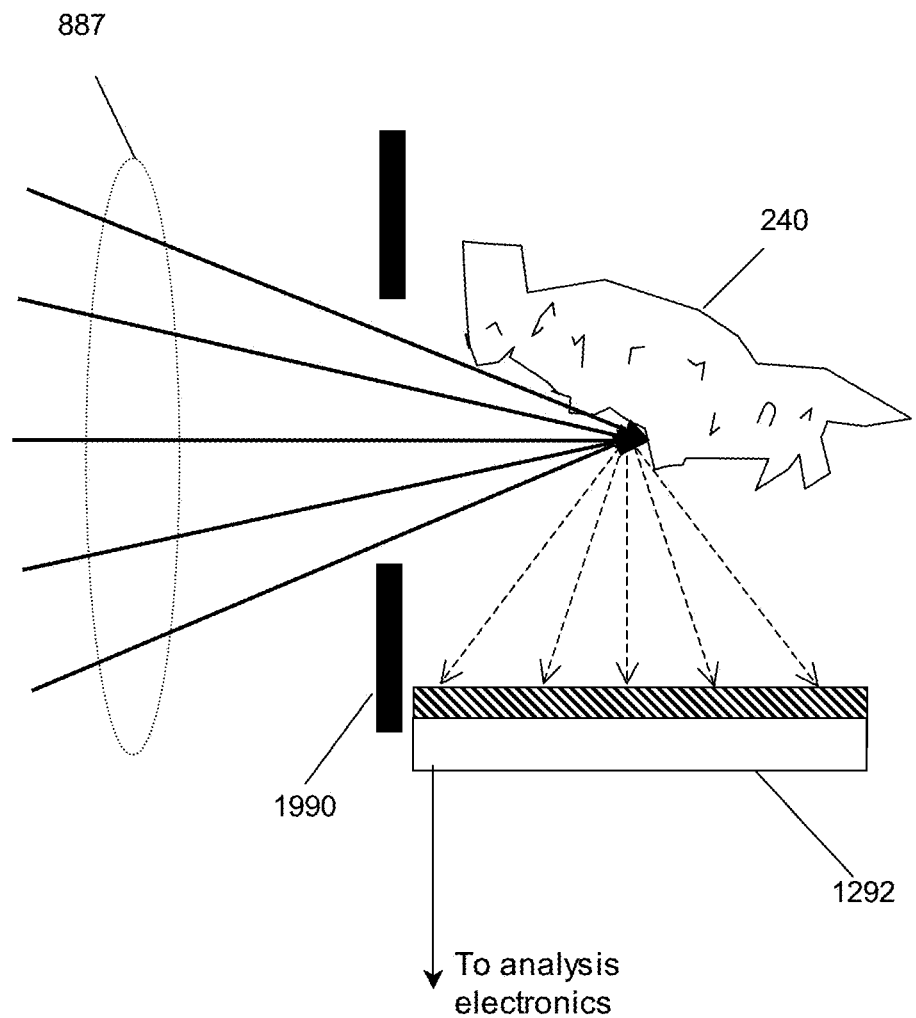
FIG. 41 illustrates a cross section schematic view of another alternative fluorescence detector according to an embodiment of the invention.

In some other configurations, such as illustrated in FIG. 41, a planar detector 1292 may be placed below the object 240, which may allow both collection over a large solid angle and no obstruction of the converging x-rays 887.

Other detector geometries and arrangements for x-ray fluorescence may be known to those skilled in the art. For more on x-ray detectors, see Albert C. Thompson, "X-Ray Detectors", Section 4.5 of the X-ray Data Booklet, which may be downloaded at: xdb.lbl.gov/Section4/Sec_4-5.pdf.

5. Other Source Configurations

A source for use in embodiments of the invention with the optical elements as described above is not limited to a target with microstructures embedded in one surface of the substrate. A target with may be coated on two sides, with electron beams bombarding both sides, as has been described in more detail in the above mentioned co-pending Patent Applications. The x-rays generated from both spots may be aligned to produce linear accumulation of x-rays propagating towards the optical system, increasing brightness and flux.

Figure 42:
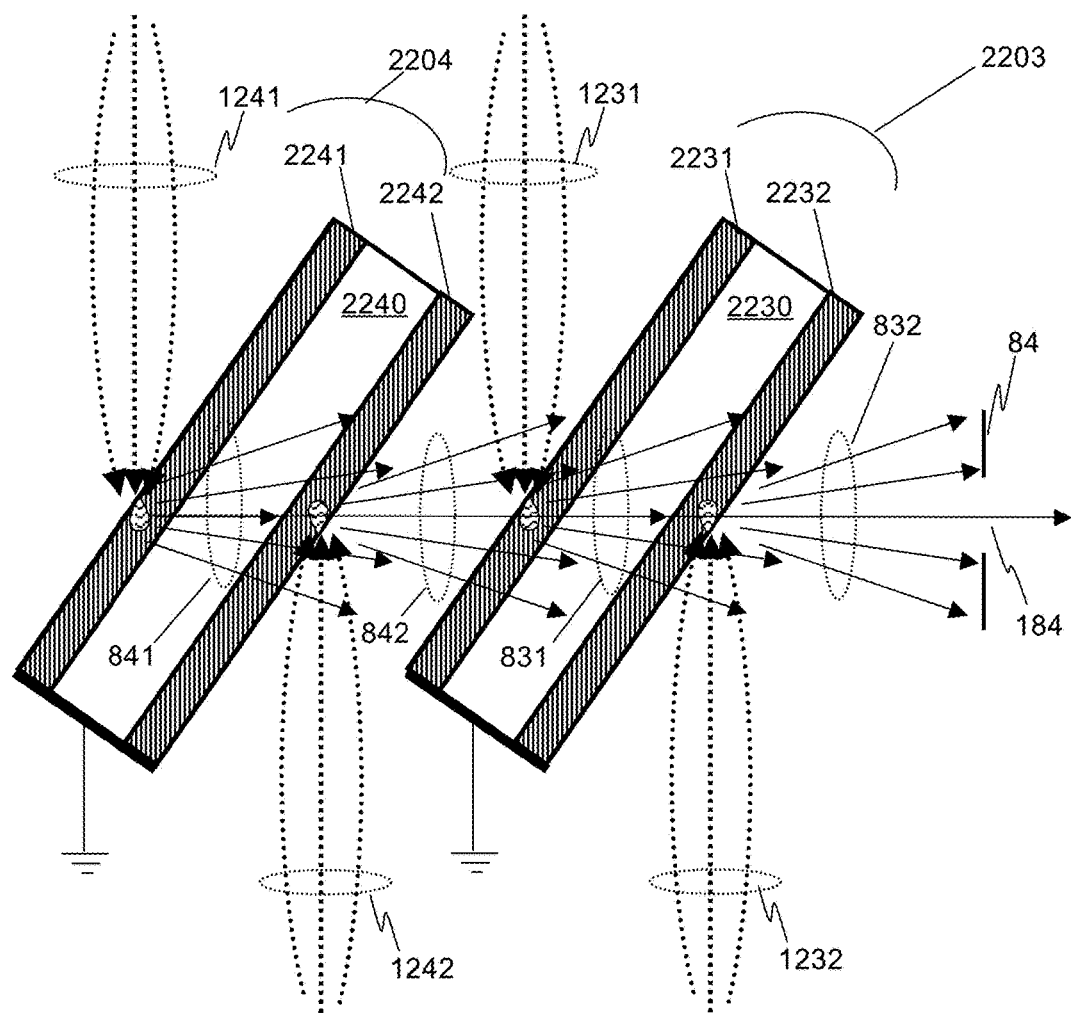
FIG. 42 illustrates a cross section schematic view of a portion of an x-ray source for use in embodiments of the invention that uses linear accumulation from multiple two-sided x-ray targets.

Multiple targets may also be aligned within the source to increase linear accumulation of x-rays. Shown in FIG. 42 is a pair of targets 2203, 2204, each with two coatings 2231 and 2232, and 2241 and 2242 respectively of x-ray generating material on a substrate 2230 and 2240, respectively. In this embodiment, the source will have four electron beams 1231, 1232, 1241, 1242 that are controlled to bombard the respective coatings on two targets 2203, 2204 and generate x-rays 831 and 832, and 841 and 842 respectively.

In this embodiment, the four x-ray generating spots are aligned with an aperture 184 in a screen 84 to appear to originate from a single point of origin. An alignment procedure as discussed above for the case of a two-sided target, except that now the four electron beams 1231, 1232, 1241, and 1242 are adjusted to maximize the total x-ray intensity at a detector placed beyond the aperture 184.

As discussed above, the targets 2203 and 2204 may be rigidly mounted to structures within the vacuum chamber, or may be mounted such that their position may be varied. In some embodiments, the targets 2203 and 2204 may be mounted as rotating anodes, to further dissipate heating. The rotation of the targets 2203 and 2204 may be synchronized or independently controlled.

The thickness of the coatings 2231, 2232 and 2241, 2242 can be selected based on the anticipated electron energy and the penetration depth or the CSDA estimate for the material. If the bombardment occurs at an angle to the surface normal, as illustrated, the angle of incidence can also affect the selection of the coating thickness. Although the tilt of the targets 2203 and 2204 relative to the electron beams 1231, 1232 and 1222 is shown as ~45°, any angle from 0° to 90° that allows x-rays to be generated may be used.

Although only two targets with four x-ray generating surfaces are illustrated in FIG. 42, embodiments with any number of targets comprising surfaces coated with x-ray generating material may be used in the same manner, each target being bombarded on one or both sides with an independently controlled electron beam. Furthermore, the coatings for the various targets may be selected to be different x-ray generating materials. For example, the upstream coatings 2241 and 2242 may be selected to be a material such as silver (Ag) or palladium (Pd) while the downstream coatings 2231 and 2232 may be selected to be rhodium (Rh), which has a higher transmission for the characteristic x-rays generated by the upstream targets. This may provide a blended x-ray spectrum, comprising multiple characteristic lines from multiple elements. Furthermore, but adjusting the various electron beam currents and densities, a tunable blend of x-rays may be achieved.

Likewise, the coatings themselves need not be uniform materials, but may be alloys of various x-ray generating substances, designed to produce a blend of characteristic x-rays. These may be used in embodiments that comprise the dual-wavelength optical systems described above.

Figure 43:
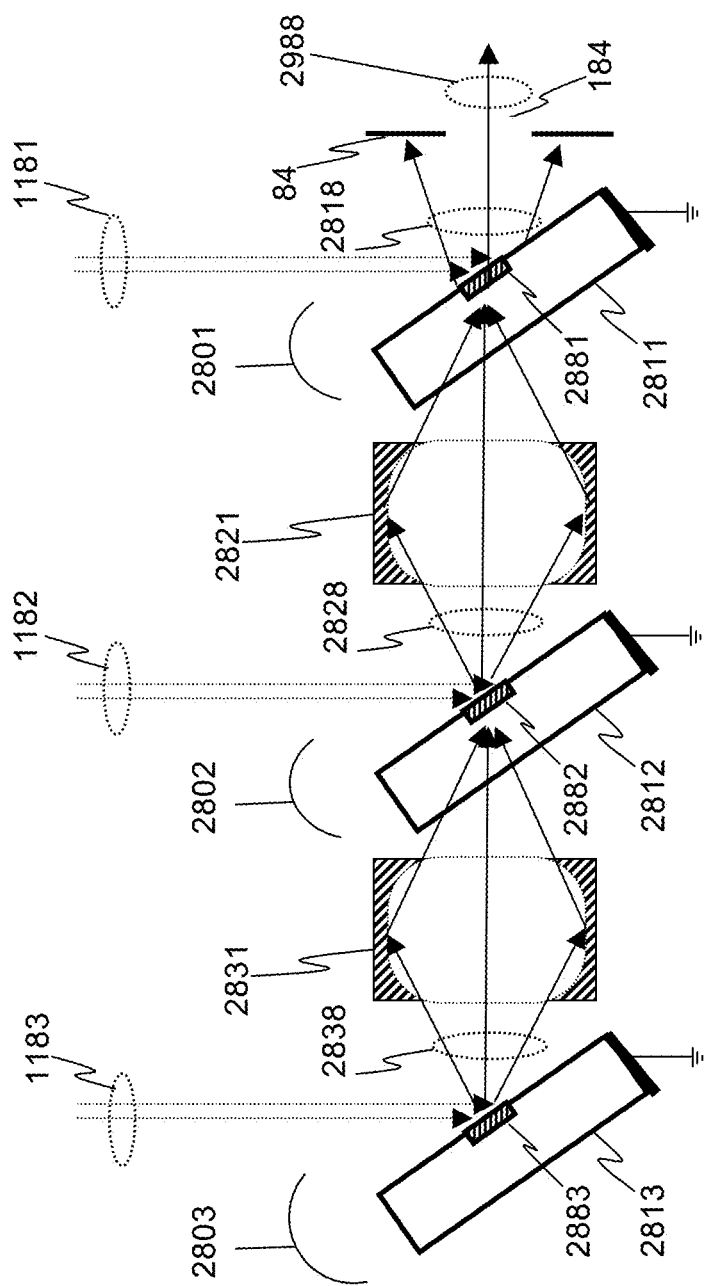
FIG. 43 illustrates a cross section schematic view of a portion of an x-ray source for use in embodiments of the invention that uses linear accumulation from multiple x-ray targets.

FIG. 43 illustrates another embodiment using three aligned targets 2801, 2802, 2803 each comprising a microstructure 2881, 2882, 2883 of x-ray generating material embedded in a substrate 2811, 2812, 2813. Each of the targets is bombarded by an electron beam 1181, 1182, 1183 respectively to generate x-rays 2818, 2828, 2838 respectively.

Between each of the x-ray generating targets, x-ray imaging mirror optics 2821 and 2831 are positioned to collect x-rays generated at wider angles and redirect them to a focus at a position corresponding to the x-ray generating spot another x-ray target. These optical elements 2821 and 2831 may comprise single reflectors, or multiple reflectors comprising quartic surfaces as described in the embodiments above. As illustrated, the focus is set to be the x-ray generating spot in the adjacent target, but in some embodiments, all the x-ray mirrors may be designed to focus x-rays to the same point, for example, at the final x-ray generating spot in the final (rightmost) x-ray target.

These imaging mirror optics 2821, 2822, 2831, 2832 may be any conventional x-ray imaging optical element, such as an ellipsoidal mirror with a reflecting surface typically fabricated from glass, or surface coated with a high mass density material, or an x-ray multilayer coated reflector (typically fabricated using layers of molybdenum (Mo) and silicon (Si)) or a crystal optic, or a combination thereof. The selection of the material and structure for an x-ray optic and its coatings may be different, depending on the spectrum of the x-rays to be collected and refocused. Although illustrated as cross sections, the entire x-ray optic or a portion thereof may have cylindrical symmetry.

6. Limitations and Extensions

Other uses for the high flux and high flux density illuminators described here for use in an x-ray fluorescence system may be known to those skilled in the art. For example, the sources as described according to the invention and the optical systems that collimate x-rays may be used for x-ray diffraction, crystallography, spectroscopy and small-angle scattering applications.

Figure 44:
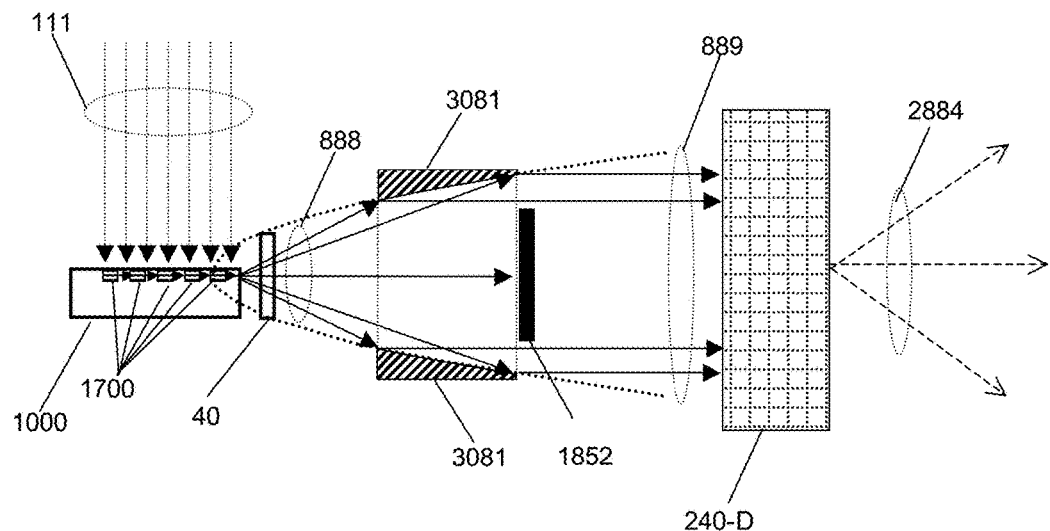
FIG. 44 illustrates a cross section schematic view of an embodiment of the invention applied to x-ray diffraction.

Illustrated in FIG. 44 is an example of an x-ray source comprising microstructures 1700 embedded in a substrate 1000 according to the invention and a paraboloid optical element 3081, as was shown in FIG. 22. The collimated x-rays 889 that emerge from the optical element 3081 may be used to illuminate a crystal 240-D, which diffracts x-rays 2884 in accordance with its crystal structure. Detection of the angles and intensities of these diffracted x-rays can be used to infer crystal structures, often for very complex molecules.

With this application, several embodiments of the invention, including the best mode contemplated by the inventors, have been disclosed. It will be recognized that, while specific embodiments may be presented, elements discussed in detail only for some embodiments may also be applied to others. Also, details and various elements described as being in the prior art may also be applied to various embodiments of the invention.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

We claim:
1. An x-ray fluorescence system comprising:
an x-ray illumination system comprising an x-ray source;
a mount to hold an object to be examined;
a means for moving the mount; and
an x-ray detector;
in which the x-ray source additionally comprises:
a vacuum chamber;
a window transparent to x-rays attached to the wall of the vacuum chamber;
and, within the vacuum chamber:
at least one electron beam emitter, and
an anode target comprising:
   a substrate comprising a first selected material, and
   a planar first surface, from which thickness is measured in a direction perpendicular to the first planar surface, and
     two orthogonal lateral dimensions are measured parallel to the first planar surface; and
   a plurality of discrete structures embedded into the first planar surface of the substrate such that each of the plurality of discrete structures is in thermal contact with the substrate,
the plurality of discrete structures comprising:
   one or more materials selected for its x-ray generation properties;
in which at least two of the plurality of discrete structures are arranged on an axis; in which the axis is parallel to the first planar surface of the substrate;
in which the axis passes through the first window;
   in which each of the discrete structures has a thickness of less than 20 microns, and
   in which each of the plurality of discrete structures has a lateral dimension in the direction of the axis of less than 50 microns; and
a means of directing electrons emitted by the at least one electron beam emitter onto the at least two arranged discrete structures such that x-rays are generated from each of the at least two arranged discrete structures;
in which at least a portion of the generated x-rays propagating on the axis from each of the two arranged discrete structures is transmitted through the window; and said system further comprising:
an optical train having an optical axis positioned to correspond to the axis on which the at least two discrete structures are arranged;
in which the optical train is further positioned to collect x-rays generated by the anode target and produce an x-ray beam with predetermined beam properties; and
in which the x-ray optical train comprises reflective elements positioned to reflect x-rays generated by the x-ray source and focus a portion of the reflected x-rays to a predetermined location; and
in which the means of moving the mount comprises translation and rotation controls so that the position of the object to be examined can be adjusted to coincide with the predetermined location where the portion of the x-rays are focused; and
in which the detector is positioned to collect fluorescence emitted by the object when illuminated by the focused x-rays and generate corresponding electronic signals.
2. The x-ray fluorescence system of claim 1, in which the detector comprises a PIN photodiode.

3. The x-ray fluorescence system of claim 1, in which the detector comprises a silicon drift detector.

4. The x-ray fluorescence system of claim 3, in which the silicon drift detector has a hole through its center such that the incident beam of x-rays travels through the hole to impinge on the object to be examined.

5. The x-ray fluorescence system of claim 1, in which the detector is selected from the group consisting of:
   a lithium drifted silicon detector and a lithium drifted germanium detector.

6. The x-ray fluorescence system of claim 1, in which the detector comprises a instrument selected from the group consisting of:
   an energy dispersive x-ray spectrometer,
   an x-ray microcalorimeter spectrometer, and
   a wavelength-dispersive x-ray spectrometer comprising at least one monochromator and an x-ray detector selected from the group consisting of:
      an ionization chamber, and a proportional counter.

7. The x-ray fluorescence system of claim 1, in which the plurality of discrete structures are arranged in a linear array along said axis; and
   the optical train is also aligned along said axis.

8. The x-ray fluorescence system of claim 1, in which the plurality of discrete structures are arranged such that x-rays generated by a predetermined number of the plurality of discrete structures when exposed to an electron beam from the electron beam emitter are transmitted through a predetermined one of the discrete structures selected from the plurality of discrete structures.

9. The x-ray fluorescence system of claim 1, in which the plurality of discrete structures comprises three or more structures.

10. The x-ray fluorescence system of claim 1, in which the optical train comprises one or more x-ray optical components that are axially symmetric.

11. The x-ray fluorescence system of claim 1, in which the first selected material is selected from the group consisting of:
   beryllium, diamond, graphite, silicon, boron nitride, silicon carbide, sapphire, and diamond-like carbon.

12. The x-ray fluorescence system of claim 1, in which the one or more materials selected for its x-ray generation properties is selected from the group consisting of:
   aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead, and combinations and alloys thereof.

13. The x-ray fluorescence system of claim 1, in which the optical train comprises an x-ray reflector with a surface corresponding to a quadric surface.

14. The x-ray fluorescence system of claim 13, in which the quadric surface is selected from the group consisting of:
   a spheroid, an ellipsoid, a paraboloid, a hyperboloid, an elliptic cylinder, a circular cylinder, an elliptic cone, and a circular cone.

15. The x-ray fluorescence system of claim 1, in which the optical train comprises a Wolter x-ray optic.

16. The x-ray fluorescence system of claim 1, additionally comprising:
   a monochromator to select x-rays of a predetermined energy and bandwidth from the x-ray beam,
   said monochromator additionally having the capability of scanning the selected x-rays over a predetermined energy range.

17. The x-ray fluorescence system of claim 16, in which the x-rays emerging from the monochromator have a predetermined energy bandwidth that is less than 10 eV.

18. The x-ray fluorescence system of claim 16, in which the monochromator comprises a channel cut crystal comprising a material selected from the group consisting of:
   silicon, germanium, lithium fluoride, and indium antimonide.

19. The x-ray fluorescence system of claim 16, in which the monochromator comprises a double crystal monochromator.

20. The x-ray fluorescence system of claim 16, additionally comprising:
   an x-ray focusing optical element positioned between the monochromator and the mount.

* * * * *